(12) United States Patent
Gdynia et al.

(10) Patent No.: US 11,274,132 B2
(45) Date of Patent: Mar. 15, 2022

(54) COMBINED PREPARATIONS OF PKM2 MODULATORS AND HMGB1

(71) Applicant: Ruprecht-Karls-Universität Heidelberg, Heidelberg (DE)

(72) Inventors: Georg Gdynia, Heidelberg (DE); Wilfried Roth, Schwetzingen (DE)

(73) Assignee: Ruprecht-Karls-Universität Heidelberg, Heidelberg (DE)

( * ) Notice: Subject to any disclaimer, the term of this patent is extended or adjusted under 35 U.S.C. 154(b) by 664 days.

(21) Appl. No.: 16/061,300

(22) PCT Filed: Dec. 12, 2016

(86) PCT No.: PCT/EP2016/080671
§ 371 (c)(1),
(2) Date: Jun. 11, 2018

(87) PCT Pub. No.: WO2017/098051
PCT Pub. Date: Jun. 15, 2017

(65) Prior Publication Data
US 2020/0289560 A1 Sep. 17, 2020

(30) Foreign Application Priority Data

Dec. 11, 2015 (EP) .................................. 15199555
Dec. 21, 2015 (EP) .................................. 15201752

(51) Int. Cl.
*A61P 35/00* (2006.01)
*A61K 38/10* (2006.01)
(Continued)

(52) U.S. Cl.
CPC .............. *C07K 14/52* (2013.01); *A61K 35/17* (2013.01); *A61K 38/10* (2013.01);
(Continued)

(58) Field of Classification Search
CPC ......... C07K 14/52; A61P 35/00; A61K 35/17; A61K 38/10; A61K 38/1709; A61K 38/19; A61K 38/00; C12N 15/11
See application file for complete search history.

(56) References Cited

U.S. PATENT DOCUMENTS 6,468,533 B1  10/2002  Tracey et al.
8,552,050 B2  10/2013  Cantley et al.
(Continued)

FOREIGN PATENT DOCUMENTS

CA   2505682 A1   6/2004
CA   2792506 A1   9/2011
(Continued)

OTHER PUBLICATIONS

G. Gdynia, M. Enders, S. Sauer, J. Kopitz, and W. Roth, "HMGB1 controls Warburg metabolism in colon cancer cells" Der Pathologe, Supplement 1, 2013; p. 12, Abstract DO-019 (Year: 2013).*
(Continued)

*Primary Examiner* — Kevin K Hill
*Assistant Examiner* — Anjeanette Roberts
(74) *Attorney, Agent, or Firm* — Taft Stettinius & Hollister LLP

(57) ABSTRACT

The present invention relates to a combined preparation comprising (i) a modulator of pyruvate kinase M2 (PKM2) activity, and (ii) an agent providing high mobility group box 1 (HMGB1) polypeptide or a derivative thereof. The present invention also relates to the aforesaid combined preparation for use as a medicament and for use in the treatment of inappropriate cellular proliferation, preferably in the treatment of cancer. Moreover, the present invention relates to a method for determining whether a subject suffering from inappropriate cellular proliferation is amenable to a treatment comprising administration of a modulator of PKM2
(Continued)

Figure 1:
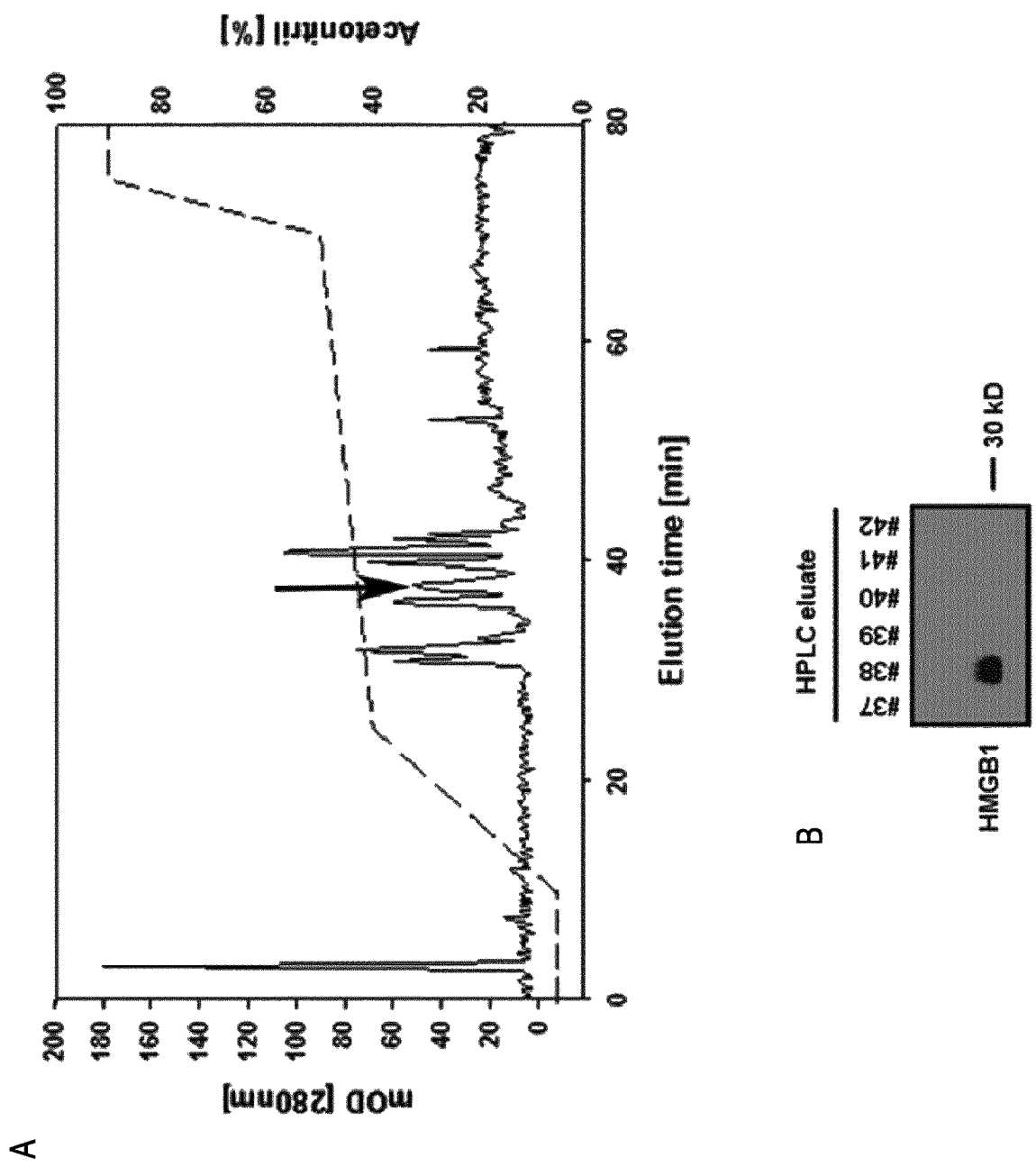
Figure 1:
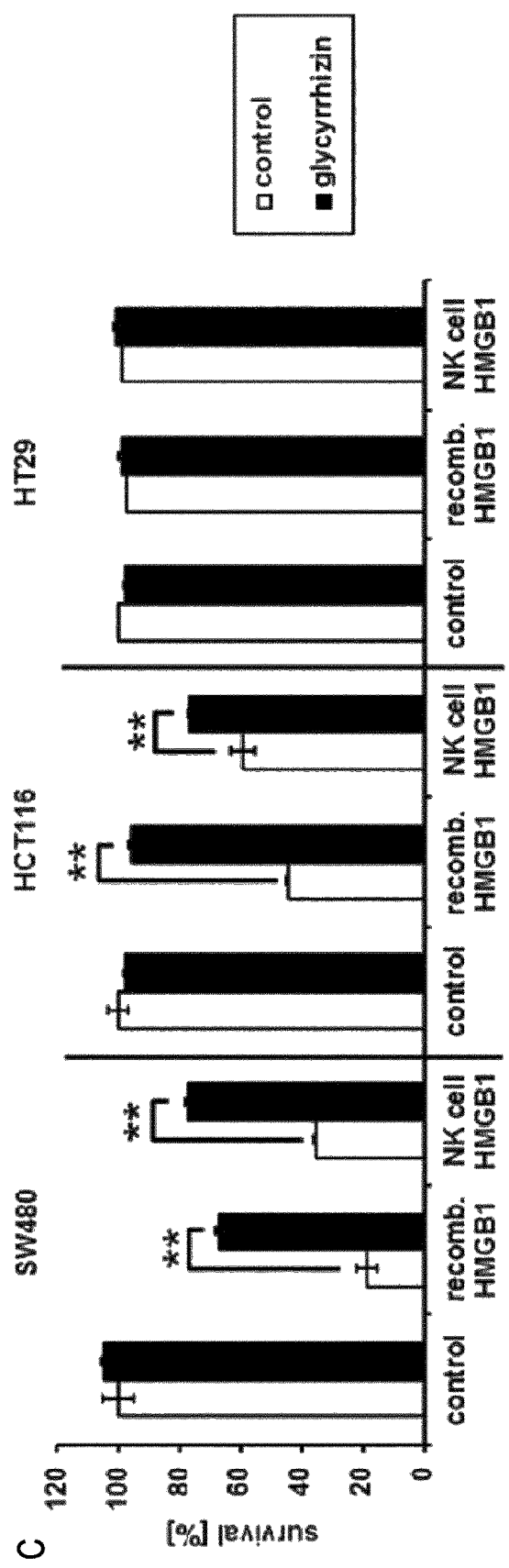
Figure 1:
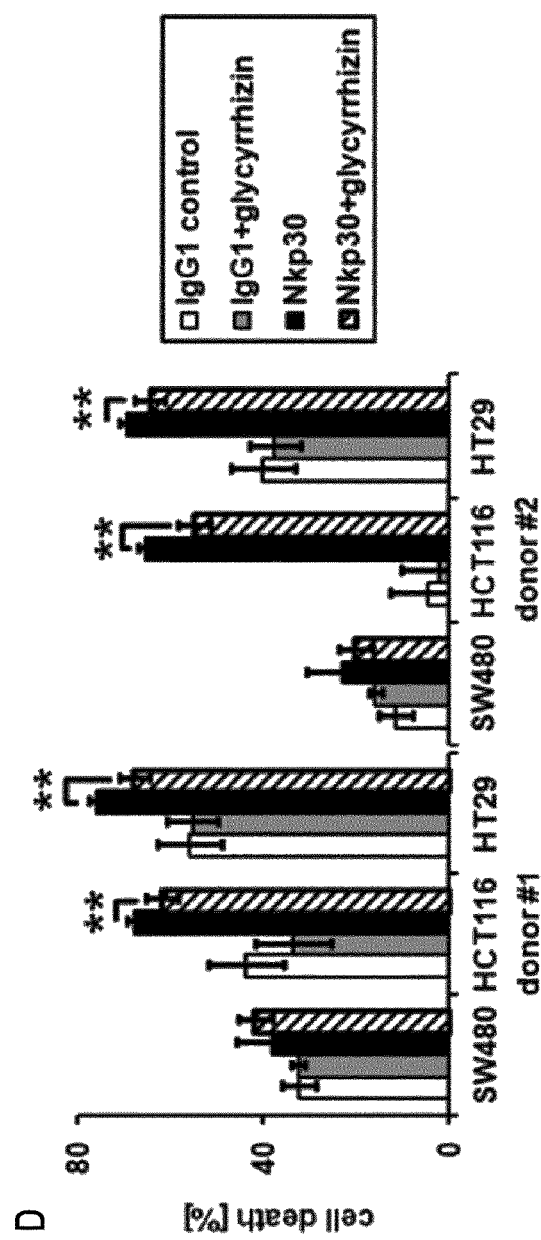
Figure 1:
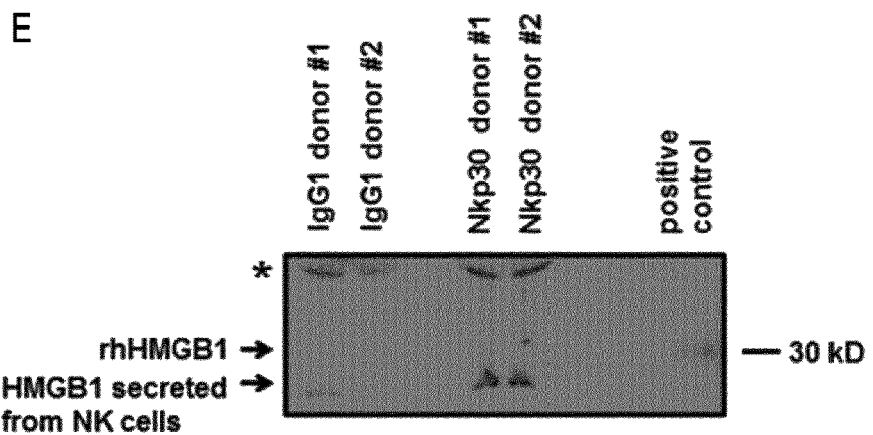
Figure 1:
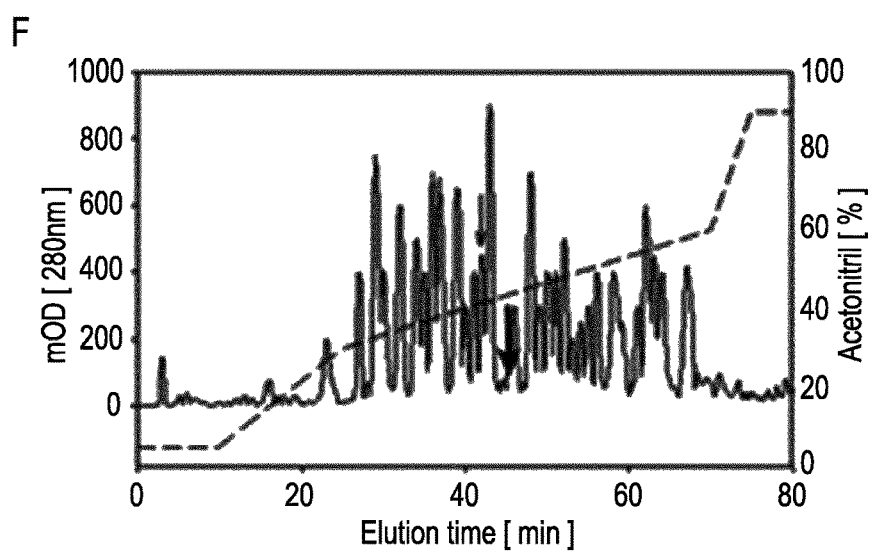
Figure 1:
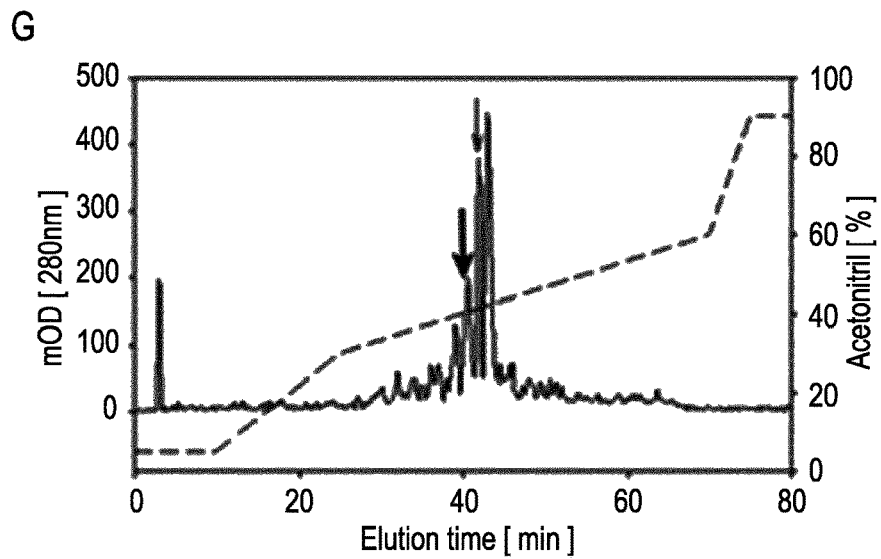
Figure 1:
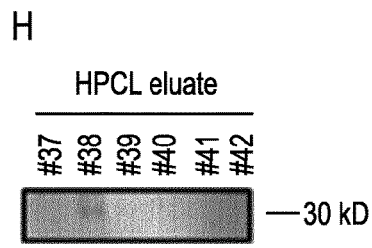
Figure 1:
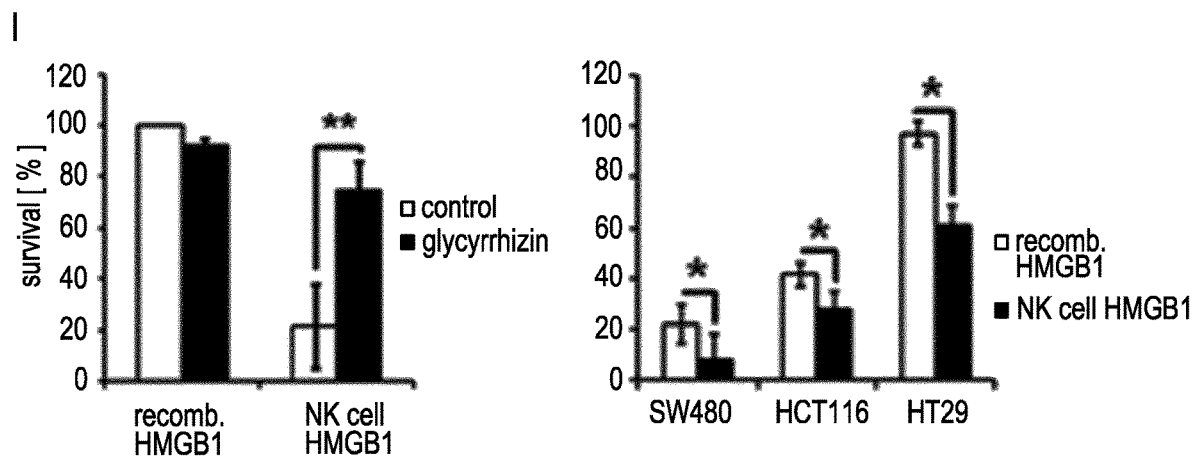
Figure 1:
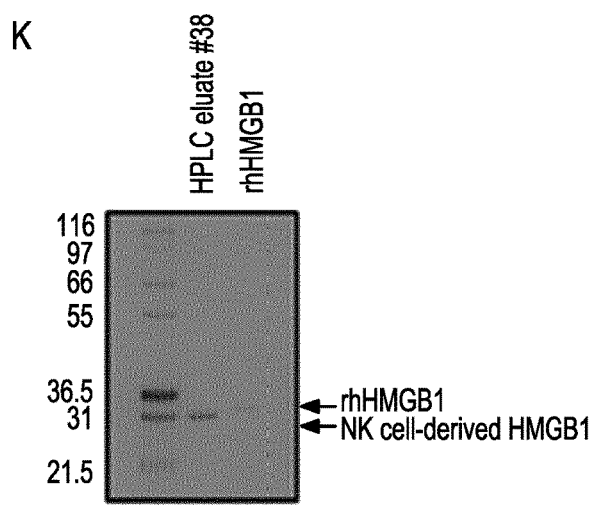
Figure 1:
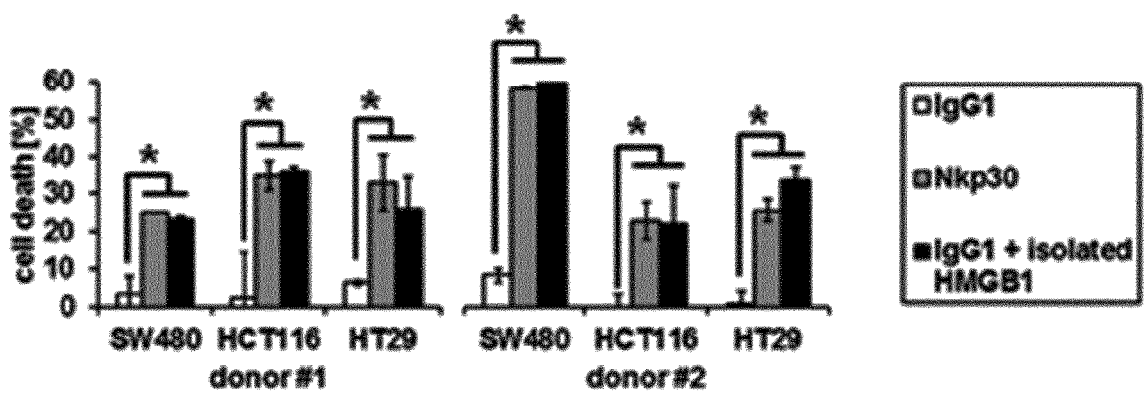
Figure 1:
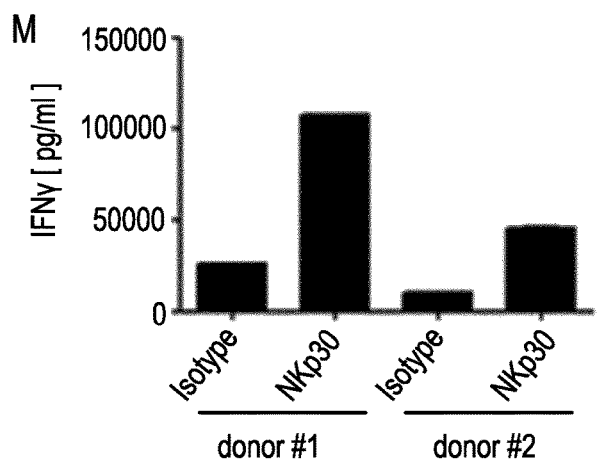

activity as the only PKM2 inhibitor and to treatment methods related thereto.

4 Claims, 19 Drawing Sheets

Specification includes a Sequence Listing.

(51) Int. Cl.
| | |
|---|---|
| *A61P 37/02* | (2006.01) |
| *A61K 38/00* | (2006.01) |
| *C07K 14/52* | (2006.01) |
| *A61K 35/17* | (2015.01) |
| *A61K 38/17* | (2006.01) |
| *A61K 38/19* | (2006.01) |
| *C12N 15/11* | (2006.01) |

(52) U.S. Cl.
CPC .......... *A61K 38/1709* (2013.01); *A61K 38/19* (2013.01); *A61P 35/00* (2018.01); *A61P 37/02* (2018.01); *C12N 15/11* (2013.01); *A61K 38/00* (2013.01)

(56) References Cited

U.S. PATENT DOCUMENTS

| | | | |
|---|---|---|---|
| 8,742,119 B2* | 6/2014 | Salituro | C07D 401/04 546/268.4 |
| 2003/0144201 A1 | 7/2003 | Tracey et al. | |
| 2008/0103086 A1 | 5/2008 | Shin et al. | |
| 2011/0123483 A1* | 5/2011 | Roth | A61K 45/06 424/85.1 |
| 2011/0218176 A1* | 9/2011 | Jennings-Spring | A61K 31/357 514/102 |

FOREIGN PATENT DOCUMENTS

| | | | |
|---|---|---|---|
| JP | 2006506441 A | 2/2006 | |
| JP | 2018538300 A | 12/2018 | |
| KR | 1020080011011 | 1/2008 | |
| RU | 2005102593 A | 10/2005 | |
| WO | 02/074337 | 9/2002 | |
| WO | 2004004763 A2 | 1/2004 | |
| WO | 2004046338 A2 | 6/2004 | |
| WO | 2006024547 | 3/2006 | |
| WO | 2008031612 | 3/2008 | |
| WO | WO-2009025781 A1 * | 2/2009 | ............ A61K 45/06 |
| WO | 2017098051 A2 | 6/2017 | |

OTHER PUBLICATIONS

Chen J, Xie J, Jiang Z, Wang B, Wang Y, Hu X. Shikonin and its analogs inhibit cancer cell glycolysis by targeting tumor pyruvate kinase-M2. Oncogene. Oct. 20, 2011;30(42):4297-306. Epub Apr. 25, 2011. (Year: 2011).*
Tennant, D. A., Durán, R. V., & Gottlieb, E. (2010). Targeting metabolic transformation for cancer therapy. Nature reviews cancer, 10(4), 267-277. (Year: 2010).*
Qian, Y., Wang, X., & Chen, X. (2014). Inhibitors of glucose transport and glycolysis as novel anticancer therapeutics. World J. Transl. Med, 3, 37-57. (Year: 2014).*
Wong, N., Ojo, D., Yan, J., & Tang, D. (2015). PKM2 contributes to cancer metabolism. Cancer letters, 356(2), 184-191. (Year: 2015).*
Granja S, Pinheiro C, Reis RM, et al. Glucose Addiction in Cancer Therapy: Advances and Drawbacks. Curr Drug Metab. 2015; 16(3):221-42. Publ: Aug. 12, 2015 (Year: 2015).*
Iqbal MA, Siddiqui FA, Gupta V, et al. Insulin enhances metabolic capacities of cancer cells by dual regulation of glycolytic enzyme pyruvate kinase M2. Mol Cancer. Jul. 9, 2013;12:72. (Year: 2013).*

Bailón-Moscoso N, Romero-Benavides JC, Ostrosky-Wegman P. Development of anticancer drugs based on the hallmarks of tumor cells. Tumour Biol. May 2014;35(5):3981-95. Epub Jan. 29, 2014 (Year: 2014).*
G. Gdynia, M. Enders, S. Sauer, J. Kopitz, and W. Roth, "HMGB1 controls Warburg metabolism in colon cancer cells" Der Pathologe, Supplement 1,2013; pi2, Abstract DO-019 (Year: 2013).*
Taddia, L., DArca, D., Ferrari, S., Marraccini, C., Severi, L., Ponterini, G., . . . & Costi, M. P. (2015). Inside the biochemical pathways of thymidylate synthase perturbed by anticancer drugs: Novel strategies to overcome cancer chemoresistance. Drug Resistance Updates, 23, 20-54. (Year: 2015).*
Li W, Liu J, Jackson K, Shi R, Zhao Y. Sensitizing the therapeutic efficacy of taxol with shikonin in human breast cancer cells. PloS one. Apr. 7, 2014;9(4):e94079. (Year: 2014).*
Gdynia, G., Keith, M., Kopitz, J., Bergmann, M., Fassl, A., Weber, A. N., et al. (2010). Danger signaling protein HMGB1 induces a distinct form of cell death accompanied by formation of giant mitochondria. Cancer research, 70(21), 8558-8568. (Year: 2010).*
Tyanova S, Cox J, Olsen J, Mann M, Frishman D. Phosphorylation variation during the cell cycle scales with structural propensities of proteins. PLoS Comput Biol. Jan. 10, 2013;9(1):e1002842. (Year: 2013).*
Anastasiou D, Yu Y, Israelsen WJ, et al. Pyruvate kinase M2 activators promote tetramer formation and suppress tumorigenesis. Nature chemical biology. Oct. 2012;8(10):839-47. Cited in IDS filed on Dec. 14, 2018 (Year: 2012).*
Trachootham D, Alexandre J, Huang P. Targeting cancer cells by ROS-mediated mechanisms: a radical therapeutic approach?. Nature reviews Drug discovery. Jul. 2009;8(7):579-91. (Year: 2009).*
G. Gdynia, M. Enders, S. Sauer, J. Kopitz, and W. Roth, "HMGB1 controls Warburg metabolism in colon cancer cells" Der Pathologe, Supplement 1,2013; pi2, Abstract DO-019. Cited in IDS filed on Dec. 14, 2018. (Year: 2013).*
Gdynia, G., Keith, M., Kopitz, J., Bergmann, M., Fassl, A., Weber, A. N., et al. (2010). Danger signaling protein HMGB1 induces a distinct form of cell death accompanied by formation of giant mitochondria. Cancer research, 70(21), 8558-8568. Cited in IDS filed on Dec. 14, 2018. (Year: 2010).*
Dong WW, Liu YJ, Lv Z, Mao YF, Wang YW, Zhu XY, Jiang L. Lung endothelial barrier protection by resveratrol involves inhibition of HMGB1 release and HMGB1-induced mitochondrial oxidative damage via an Nrf2-dependent mechanism. Free Radical Biology and Medicine. Nov. 1, 2015;88:404-16. (Year: 2015).*
Tang D, Kang R, Zeh III HJ, Lotze MT. High-mobility group box 1, oxidative stress, and disease. Antioxidants & redox signaling. Apr. 1, 2011;14(7):1315-35. (Year: 2011).*
Elf SE, Chen J. Targeting glucose metabolism in patients with cancer. Cancer. Mar. 15, 2014;120(6):774-80. (Year: 2014).*
Anahid Jewett et al.; Differential Secretion of TNF-α and IFN-γ by Human Peripheral Blood-Derived NK Subsets and Association with Functional Maturation; Journal of Clinical Immunology; 1996; 9 pages; vol. 16, No. 1.
Daniel W. Lee et al.; Current Concepts in the Diagnosis and Management of Cytokine Release Syndrome; Blood; 2014; 15 pages; vol. 124, No. 2.
Higgins et al.; Pubmed_result.txt; CABIOS; 1989; 1 page.
Saul B. Needlman et al.; A General Method Applicable to the Search for Similarities in the Amino Acid Sequence of Two Proteins; J. Mol. Biol.; 1970; 11 pages; vol. 48.
Temple F. Smith et al.; Comparison of Biosequences; Advances in Applied Mathematics; 1981; 8 pages; vol. 2.
Loren D. Walensky et al.; Activation of Apoptosis in Vivo by a Hydrocarbon-Stapled BH3 Helix; Science; 2004; 6 pages; vol. 305.
Eric L. Snyder et al.; Cell Penetrating Peptides in Drug Delivery; Pharmaceutical Research; Mar. 2004; 5 pages; vol. 21, No. 3.
Siok-Keen Tey; Adoptive T-Cell Therapy: Adverse Events and Safety Switches; Clinical & Translational Immunology; 2014; 7 pages; vol. 3, No. e17.
Da-Fei Feng et al.; Progressive Sequence Alignment as a Prerequisite to Correct Phylogenetic Trees; Journal of Molecular Evolution; 1987; 10 pages; vol. 25.

(56) References Cited

OTHER PUBLICATIONS

International Preliminary Report on Patentability; The International Bureau of WIPO; International Application No. PCT/EP2016/080671; dated Jun. 12, 2018; 14 pages.

Hyun Ju Kang et al.; Non-Histone Nuclear Factor HMGB1 is Phosphorylated and Secreted in Colon Cancers; Laboratory Investigation; 2009; 12 pages; vol. 89.

Anastasiou et al., "Pyruvate kinase M2 activators promote tetramer formation and suppress tumorigenesis," Nat Chem Biol., Oct. 2012, pp. 839-847, vol. 8(10).

Anthis et al., "β Integrin Tyrosine Phosphorylation Is a Conserved Mechanism for Regulating Talin-induced Integrin Activation," Journal of Biological Chemistry, Dec. 25, 2009, pp. 36700-36710,vol. 284, No. 52.

Apetoh et al., "Toll-like receptor 4-dependent contribution of the immune system to anticancer chemotherapy and radiotherapy," Nature Medicine, Sep. 2007, pp. 1050-1059, vol. 13, No. 9.

Bhat et al., "NK-cell-dependent killing of colon carcinoma cells is mediated by natural cytotoxicity receptors (NCRs) and stimulated by parvovirus infection of target cells," BMC Cancer, 2013, pp. 1-9, vol. 13.

Calogero et al., "The lack of chromosomal protein Hmg1 does not disrupt cell growth but causes lethal hypoglycaemia in newborn mice," Nature Genetics, Jul. 1999, pp. 276-280, vol. 22.

Christofk et al., "Pyruvate kinase M2 is a phosphotyrosine-binding protein," Nature, Mar. 2008, pp. 181-186, vol. 452.

Erlandsson Harris et al., "Mini-review: The nuclear protein HMGB1 as a proinflammatory mediator," Eur. J. Immunol., 2004, pp. 1503-1512, vol. 34.

Gdynia et al., "Danger Signaling Protein HMGB1 Induces a Distinct Form of Cell Death Accompanied by Formation of Giant Mitochondria," Cancer Res., Nov. 1, 2010, pp. 8558-8568, vol. 70(21).

Gdynia et al., "HMGB1 controls Warburg metabolism in colon cancer cells," Der Pathologe, Suppl 1, 2013, p. 12.

Gdynia et al., "The HMGB1 protein induces a metabolic type of tumour cell death by blocking aerobic respiration," Nature Communications, Mar. 7, 2016, pp. 1-13, vol. 7.

Gdynia et al., "HMGB1 als metabolische Waffe im Arsenal natiirlicher Killerzellen," Der Pathologe, Sep. 14, 2016, pp. 169-172, vol. 37 (Suppl 2).

Grundtman et al., "Effects of HMGB1 on in vitro responses of isolated muscle fibers and functional aspects in skeletal muscles of idiopathic inflammatory myopathies," The FASEB Journal, 2010, pp. 570-578, vol. 24.

Hitosugi et al., "Tyrosine Phosphorylation Inhibits PKM2 to Promote the Warburg Effect and Tumor Growth," Sci Signal., Jan. 28, 2010, pp. 1-16, vol. 2(97).

Ikeda et al., "Allosteric Regulation of Pyruvate Kinase M2 Isozyme Involves a Cysteine Residue in the Intersubunit Contact," The Journal of Biological Chemistry, May 15, 1998, pp. 12227-12233, vol. 273(20).

Iqbal et al., "Insulin Upregulates PKM2 Expression But Inhibits its Activity to Promote Cancer Cell Metabolism," European Journal of Cancer, Jul. 10, 2012, p. S120, vol. 48, Suppl. 5.

Kaminski et al., "T cell Activation is Driven by an ADP-Dependent Glucokinase Linking Enhanced Glycolysis with Mitochondrial Reactive Oxygen Species Generation," Cell Reports, Nov. 29, 2012, pp. 1300-1315, vol. 2.

Lazzarino et al., "Prevention by Fructose-1,6-bisphosphate of Cardiac Oxidative Damage Induced in Mice by Subchronic Doxorubicin Treatment," Cancer Research, Dec. 15, 1987, pp. 6511-6516, vol. 47.

Lotze et al., "High-mobility group box 1 protein (HMGB1): nuclear weapon in the immune arsenal," Nature Reviews—Immunology, Apr. 2005, pp. 331-342, vol. 5.

Min et al., "Chaperone-like Activity of High-Mobility Group Box 1 Protein and Its Role in Reducing the Formation of Polyglutamine Aggregates," The Journal of Immunology, Jan. 9, 2013, pp. 1797-1806, vol. 190.

Ren et al., "Induction of Erythroid Differentiation in Human Erythroleukemia Cells by Depletion of Malic Enzyme 2," PLoS ONE, Sep. 2010, pp. 1-12, vol. 5, Issue 9.

Sahdev et al., "Production of active eukaryotic proteins through bacterial expression systems: a review of the existing biotechnology strategies," Mol Cell Biochem, 2008, pp. 249-264, vol. 307.

Saidi et al., "HMGB1-Dependent Triggering of HIV-1 Replication and Persistence in Dendritic Cells as a Consequence of NK-DC Cross-Talk," PLoS ONE, Oct. 2008, pp. 1-13, vol. 3, Issue 10.

Tennant et al., "Targeting metabolic transformation for cancer therapy," Nature Reviews—Cancer, Apr. 2010, pp. 267-277, vol. 10.

Vander Heiden et al., "Understanding the Warburg Effect: The Metabolic Requirements of Cell Proliferation," Science, May 22, 2009, pp. 1029-1033, vol. 324(5930).

Veith et al., "Organism-Adapted Specificity of the Allosteric Regulation of Pyruvate Kinase in Lactic Acid Bacteria," PLoS Computational Biology, Jul. 2013, pp. 1-15, vol. 9, Issue 7.

Walsh et al., "ML265, a potent PKM2 activator induces tetramerization and reduces tumor formation and size in a mouse xenograft model," Probe Report from the NIH Molecular Libraries Program, May 8, 2013, pp. 1-33.

Wang et al., "HMG-1 as a Late Mediator of Endotoxin Lethality in Mice," Science, Jul. 9, 1999, 248-251, vol. 285.

Yang, D. et al., "High mobility group box-1 protein induces the migration and activation of human dendritic cells and acts as an alarmin," Journal of Leukocyte Biology, Jan. 2007, pp. 59-66, vol. 81.

Yang, L. et al., "PKM2 regulates the Warburg effect and promotes HMGB1 release in sepsis," Nature Communications, Jul. 14, 2014, pp. 1-9, vol. 5.

Youn et al., "Nucleocytoplasmic Shuttling of HMGB1 is Regulated by Phosphorylation that Redirects It toward Secretion," J. Immunol, 2006, pp. 7889-7897, vol. 177.

Zetterstrom et al., "High Mobility Group Box Chromosomal Protein 1 (HMGB1) Is an Antibacterial Factor Produced by the Human Adenoid," Pediatric Research, 2002, pp. 148-154, vol. 52, No. 2.

Zhdanov et al., "Availability of the key metabolic substrates dictates the respiratory response of cancer cells to the mitochondrial uncoupling," Biochimica et Biophysica Acta, 2014, pp. 51-62, vol. 1837.

European Patent Office, International Search Report for PCT/EP2016/080671, dated Nov. 15, 2017.

European Patent Office, Written Opinion of the International Searching Authority for PCT/EP2016/080671, dated Nov. 15, 2017.

English Translation of Office Action; Japanese Patent Office; Japanese Application No. 2019-531095; dated Mar. 9, 2021; 6 pages.

Taskinen, Minna et al.; Prognostic Impact of Microvessel Density in Follicular Lymphoma Patients Treated with Immunochemotherapy; Blood, Journal of the American Society of Hematology; 2008; p. 980; vol. 112; No. 11; The American Society of Hematology.

Carsetti, Laura et al.; Molecular Requirements for Syk-Mediated Intracellular Signaling and B-Cell Transformation; Blood, Journal of the American Society of Hematology; 2008; p. 980; vol. 112; No. 11; The American Society of Hematology.

Alexanian, Anna et al.; Post-translational regulation of COX2 activity by FYN in prostate cancer cells; Oncotarget; 2014; pp. 4232-4243; vol. 5; No. 12.

Cerwenka, Adelheid et al.; HMGB1: The metabolic weapon in the arsenal of NK cells; Molecular & Cellular Oncology; 2016; 4 pages; vol. 3; No. 4; Taylor & Francis Group, LLC.

First Office Action; China National intellectual Property Administration; Chinese Application No. 201680072545.0; dated May 24, 2021; 11 pages.

Office Action; Japanese Patent Office; Japanese Application No. 2018-530152; dated May 25, 2021; 17 pages.

Telusma, Gloria et al.; Dendritic cell activating peptides induce distinct cytokine profiles; International Immunology; 2006; pp. 1563-1573; vol. 18, No. 11; Japanese Society for Immunology.

Stefanovsky, Victor Y. et al.; ERK Modulates DNA Bending and Enhancesome Structure by Phosphorylating HMG1-Boxes 1 and 2 of the RNA Polymerase I Transcription Factor UBF; Biochemistry; 2006; pp. 3626-3634; vol. 45; American Chemical Society.

Office Action; European Patent Office; European Application No. 16831815.2; dated May 10, 2021; 11 pages.

(56) References Cited

OTHER PUBLICATIONS

Heidari, Reza et al.; Dithiothreitol supplementation mitigates hepatic and renal injury in bile duct litigated mice: Potential application in the treatment of cholestasis-associated complications; Biomedicine & Pharmacotherapy; 2018; pp. 1022-1032; vol. 99; Elsevier Masson SAS.

Official Action (Inquiry) of the Substantive Examination; Federal Institute of Industrial Property in St. Petersburg; Russian Patent Application No. 2019115811/10(030067); dated Aug. 14, 2020; 18 pages.

\* cited by examiner

SEQUENCE LISTING

```
<160> NUMBER OF SEQ ID NOS: 12

<210> SEQ ID NO 1
<211> LENGTH: 15
<212> TYPE: PRT
<213> ORGANISM: Artificial
<220> FEATURE:
<223> OTHER INFORMATION: PKM2 inhibitory peptide NP-M2tide
<220> FEATURE:
<221> NAME/KEY: MOD_RES
<222> LOCATION: (8)..(8)
<223> OTHER INFORMATION: phosphotyrosine

<400> SEQUENCE: 1

Gly Gly Ala Val Asp Asp Asp Tyr Ala Gln Phe Ala Asn Gly Gly
1               5                   10                  15

<210> SEQ ID NO 2
<211> LENGTH: 531
```

<212> TYPE: PRT
<213> ORGANISM: Homo sapiens

<400> SEQUENCE: 2

```
Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Ile Tyr His Leu Gln Leu Phe Glu Glu Leu Arg Arg
385                 390                 395                 400
```

```
Leu Ala Pro Ile Thr Ser Asp Pro Thr Glu Ala Thr Ala Val Gly Ala
                405                 410                 415
Val Glu Ala Ser Phe Lys Cys Cys Ser Gly Ala Ile Ile Val Leu Thr
            420                 425                 430
Lys Ser Gly Arg Ser Ala His Gln Val Ala Arg Tyr Arg Pro Arg Ala
        435                 440                 445
Pro Ile Ile Ala Val Thr Arg Asn Pro Gln Thr Ala Arg Gln Ala His
    450                 455                 460
Leu Tyr Arg Gly Ile Phe Pro Val Leu Cys Lys Asp Pro Val Gln Glu
465                 470                 475                 480
Ala Trp Ala Glu Asp Val Asp Leu Arg Val Asn Phe Ala Met Asn Val
                485                 490                 495
Gly Lys Ala Arg Gly Phe Phe Lys Lys Gly Asp Val Val Ile Val Leu
            500                 505                 510
Thr Gly Trp Arg Pro Gly Ser Gly Phe Thr Asn Thr Met Arg Val Val
        515                 520                 525
Pro Val Pro
    530

<210> SEQ ID NO 3
<211> LENGTH: 1593
<212> TYPE: DNA
<213> ORGANISM: Artificial
<220> FEATURE:
<223> OTHER INFORMATION: cDNA encoding PKM2, lacking stop codon

<400> SEQUENCE: 3
atgtcgaagc ccatagtga agccgggact gccttcattc agacccagca gctgcacgca      60
gccatggctg acacattcct ggagcacatg tgccgcctgg acattgattc accacccatc    120
acagcccgga cactggcat catctgtacc attggcccag cttcccgatc agtggagacg     180
ttgaaggaga tgattaagtc tggaatgaat gtggctcgtc tgaacttctc tcatggaact    240
catgagtacc atgcggagac catcaagaat gtgcgcacag ccacggaaag ctttgcttct    300
gaccccatcc tctaccggcc cgttgctgtg gctctagaca ctaaaggacc tgagatccga    360
actgggctca tcaagggcag cggcactgca gaggtggagc tgaagaaggg agccactctc    420
aaaatcacgc tggataacgc ctacatggaa aagtgtgacg agaacatcct gtggctggac    480
tacaagaaca tctgcaaggt ggtggaagtg gcagcaagaa tctacgtgga tgatgggctt    540
atttctctcc aggtgaagca gaaaggtgcc gacttcctgg tgacgaggt ggaaaatggt    600
ggctccttgg gcagcaagaa gggtgtgaac cttcctgggg ctgctgtgga cttgcctgct    660
gtgtcggaga aggacatcca ggatctgaag tttgggg tcg agcaggatgt tgatatggtg    720
tttgcgtcat tcatccgcaa ggcatctgat gtccatgaag ttaggaaggt cctgggagag    780
aagggaaaga acatcaagat tatcagcaaa atcgagaatc atgaggg ggt tcggaggttt    840
gatgaaatcc tggaggccag tgatgggatc atggtggctc gtggtgatct aggcattgag    900
attcctgcag agaaggtctt ccttgctcag aagatgatga ttggacggtg caaccgagct    960
gggaagcctg tcatctgtgc tactcagatg ctggagagca tgatcaagaa gccccgcccc   1020
actcgggctg aaggcagtga tgtggccaat gcagtcctgg atggagccga ctgcatcatg   1080
ctgtctggag aaacagccaa aggg gactat cctctggagg ctgtgcgcat gcagcacctg   1140
attgcccgtg aggcagaggc tgccatctac cacttgcaat atttgagga actccgccgc   1200
ctggcgccca ttaccagcga ccccacagaa gccaccgccg tgggtgccgt ggaggcctcc   1260
```

-continued

```
ttcaagtgct gcagtggggc cataatcgtc ctcaccaagt ctggcaggtc tgctcaccag   1320
gtggccagat accgcccacg tgcccccatc attgctgtga cccggaatcc ccagacagct   1380
cgtcaggccc acctgtaccg tggcatcttc cctgtgctgt gcaaggaccc agtccaggag   1440
gcctgggctg aggacgtgga cctccgggtg aactttgcca tgaatgttgg caaggcccga   1500
ggcttcttca agaagggaga gtgtggtcat tgtgctgaccg gatggcgccc tggctccggc   1560
ttcaccaaca ccatgcgtgt tgttcctgtg ccg                                1593
```

<210> SEQ ID NO 4
<211> LENGTH: 215
<212> TYPE: PRT
<213> ORGANISM: Homo sapiens

<400> SEQUENCE: 4

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Asp Glu Asp Glu
        195                 200                 205

Glu Glu Asp Asp Asp Asp Glu
    210                 215
```

<210> SEQ ID NO 5
<211> LENGTH: 75
<212> TYPE: PRT
<213> ORGANISM: Homo sapiens

<400> SEQUENCE: 5

```
Lys Phe Lys Asp Pro Asn Ala Pro Lys Arg Pro Pro Ser Ala Phe Phe
1               5                   10                  15

Leu Phe Cys Ser Glu Tyr Arg Pro Lys Ile Lys Gly Glu His Pro Gly
            20                  25                  30

Leu Ser Ile Gly Asp Val Ala Lys Lys Leu Gly Glu Met Trp Asn Asn
        35                  40                  45
```

Thr Ala Ala Asp Asp Lys Gln Pro Tyr Glu Lys Lys Ala Ala Lys Leu
            50                  55                  60

Lys Glu Lys Tyr Glu Lys Asp Ile Ala Ala Tyr
 65                  70                  75

<210> SEQ ID NO 6
<211> LENGTH: 645
<212> TYPE: DNA
<213> ORGANISM: Homo sapiens

<400> SEQUENCE: 6
atgggcaaag gagatcctaa gaagccgaga cggaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaaagcgga caaggcccgt tatgaaagag aaatgaaaac ctatatccct     240
cccaaagggg agacaaaaaa gaagttcaag gatcccaatg cacccaagag gcctccttcg     300
gccttcttcc tcttctgctc tgagtatcgc ccaaaaatca aggagaaaca tcctggcctg     360
tccattggtg atgttgcgaa gaaactggga gagatgtgga taacactgc tgcagatgac     420 aagcagcctt atgaaaagaa ggctgaaaag ctgaaggaaa atacgaaaa ggatattgct     480 gcatatcgag ctaaaggaaa gcctgatgca gcaaaaaagg gagttgtcaa ggctgaaaaa     540
agcaagaaaa agaaggaaga ggaggaaggt gaggaagatg aagaggatga ggaggaggag     600
gaagatgaag aagatgaaga tgaagaagaa gatgatgatg atgaa                    645

<210> SEQ ID NO 7
<211> LENGTH: 225
<212> TYPE: DNA
<213> ORGANISM: Homo sapiens

<400> SEQUENCE: 7
aagttcaagg atcccaatgc acccaagagg cctccttcgg ccttcttcct cttctgctct      60
gagtatcgcc caaaaatcaa ggagaacat cctggcctgt ccattggtga tgttgcgaag     120
aaactgggag agatgtggaa taacactgct gcagatgaca agcagcctta tgaaaagaag     180
gctgcgaagc tgaaggaaaa atacgaaaag gatattgctg catat                    225

<210> SEQ ID NO 8
<211> LENGTH: 531
<212> TYPE: PRT
<213> ORGANISM: Homo sapiens

<400> SEQUENCE: 8

Met Ser Lys Pro His Ser Glu Ala Gly Thr Ala Phe Ile Gln Thr Gln
 1               5                  10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
 65                  70                  75                  80

His Glu Tyr His Ala Glu Thr Ile Lys Asn Val Arg Thr Ala Thr Glu
                85                  90                  95

```
Ser Phe Ala Ser Asp Pro Ile Leu Tyr Arg Pro Val Ala Val Ala Leu
                100                 105                 110

Asp Thr Lys Gly Pro Glu Ile Arg Thr Gly Leu Ile Lys Gly Ser Gly
            115                 120                 125

Thr Ala Glu Val Glu Leu Lys Lys Gly Ala Thr Leu Lys Ile Thr Leu
        130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
                405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
        435                 440                 445

Pro Ile Ile Ala Val Thr Arg Asn Pro Gln Thr Ala Arg Gln Ala His
    450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
```

Pro Val Pro
    530

<210> SEQ ID NO 9
<211> LENGTH: 25
<212> TYPE: RNA
<213> ORGANISM: Artificial
<220> FEATURE:
<223> OTHER INFORMATION: artificial siRNA

<400> SEQUENCE: 9
cccugugggu aaauuggcuc uauau                                          25

<210> SEQ ID NO 10
<211> LENGTH: 21
<212> TYPE: DNA
<213> ORGANISM: Artificial
<220> FEATURE:
<223> OTHER INFORMATION: artifical control siRNA

<400> SEQUENCE: 10
ccugcaguac uucaagcggt t                                              21

<210> SEQ ID NO 11
<211> LENGTH: 75
<212> TYPE: PRT
<213> ORGANISM: Artificial
<220> FEATURE:
<223> OTHER INFORMATION: HMGB1 box B Y-> Q mutein

<400> SEQUENCE: 11

Lys Phe Lys Asp Pro Asn Ala Pro Lys Arg Pro Pro Ser Ala Phe Phe
1               5                   10                  15

Leu Phe Cys Ser Glu Gln Arg Pro Lys Ile Lys Gly Glu His Pro Gly
            20                  25                  30

Leu Ser Ile Gly Asp Val Ala Lys Lys Leu Gly Glu Met Trp Asn Asn
        35                  40                  45

Thr Ala Ala Asp Asp Lys Gln Pro Gln Glu Lys Ala Ala Lys Leu
    50                  55                  60

Lys Glu Lys Gln Glu Lys Asp Ile Ala Ala Gln
65                  70                  75

<210> SEQ ID NO 12
<211> LENGTH: 215
<212> TYPE: PRT
<213> ORGANISM: Artificial
<220> FEATURE:
<223> OTHER INFORMATION: HMGB1 Y -> Q mutein

<400> SEQUENCE: 12

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

```
Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Gln Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Gln
    130                 135                 140

Glu Lys Lys Ala Ala Lys Leu Lys Glu Lys Gln Glu Lys Asp Ile Ala
145                 150                 155                 160

Ala Gln Arg Ala Lys Gly Lys Pro Asp Ala Ala Lys Lys Gly Val Val
            165                 170                 175

Lys Ala Glu Lys Ser Lys Lys Lys Lys Glu Glu Glu Glu Asp Glu Glu
            180                 185                 190

Asp Glu Glu Asp Glu Glu Glu Glu Asp Glu Glu Asp Glu Glu Asp Glu
            195                 200                 205

Glu Glu Asp Asp Asp Asp Glu
    210                 215
```

COMBINED PREPARATIONS OF PKM2 MODULATORS AND HMGB1

CROSS-REFERENCE TO RELATED APPLICATIONS

The present application is a U.S. national stage of, and claims the priority benefit of, International Patent Application Serial No. PCT/EP2016/080671, filed Dec. 12, 2016, and also claims the priority benefit of European Patent Application Serial No. 15199555.2, filed Dec. 11, 2015 and European Patent Application Serial No. 15201752.1, filed Dec. 21, 2015, the text and drawings of which are hereby incorporated by reference in their entireties.

The present invention relates to a combined preparation comprising (i) a modulator of pyruvate kinase M2 (PKM2) activity, and (ii) an agent providing high mobility group box 1 (HMGB1) polypeptide or a derivative thereof. The present invention also relates to the aforesaid combined preparation for use as a medicament and for use in the treatment of inappropriate cellular proliferation, preferably in the treatment of cancer. Moreover, the present invention relates to a method for determining whether a subject suffering from inappropriate cellular proliferation is amenable to a treatment comprising administration of a modulator of PKM2 activity as the only PKM2 inhibitor and to treatment methods related thereto.

The High Mobility Group Box 1 (HMGB1) protein belongs to the High Mobility Group (HMG) family of nuclear proteins, which was named due to the unusual high mobility of its members in SDS-polyacrylamide gel-electrophoresis (SDS-PAGE). These proteins are, second to histones, among the most abundant proteins associated with chromatin and they play an architectural role in the nucleus of the eukaryotic cell in that they bend, distort or otherwise modify the conformation of DNA, thereby also modifying the binding of transcription factors to DNA. HMG proteins have been implicated in the genesis of various disorders, like several kinds of benign tumors and autoimmune diseases. Furthermore, the release of high amounts of HMGB1, in particular from NK cells, is pivotal for dendritic cell activation (Saidi et al. (2008), PloS one 3, e3601) and chemotaxis (Yang et al. (2007), Journal of leukocyte biology 81, 59-66). In addition, HMGB1 exhibits striking antimicrobial activity resulting in rapid killing of bacteria (Zetterstrom et al., (2002), Pediatric research 52, 148-154).

Endogenous HMGB1 is also intricately involved in the energy metabolism of cells and organs. HMGB1 knock-out mice are unable to utilize glycogen storage pools in hepatocytes and die due to perinatal hypoglycemia. Glucose temporarily rescues the animals, but the mice succumb several days later due to severe atrophy of inner organs, muscle, and fatty tissue (Calogero et al. (1999), Nature genetics 22, 276-280). Ex vivo incubation of murine muscle tissue with HMGB1 leads to rapid exhaustion of muscle fibers, and elevated HMGB1 concentrations are found in the myoplasm of patients suffering from polymyositis (Grundtman et al. (2010), The FASEB journal 24, 570-578). In summary, both lack and excess of HMGB1 severely affects cellular energy metabolism.

Extracellular HMGB1 is a potent cytokine and a strong activating factor for macrophages and other cells of the immune system, leading to an extensive inflammatory reaction. For this reason, HMGB1 has been implicated in autoimmune diseases such as systemic lupus erythematosus and rheumatoid arthritis. However, high amounts of HMGB1 in blood have also been found to indicate serious or life-threatening inflammatory conditions like sepsis. To antagonize such HMGB1 related pathologies, inhibitors of HMGB1 function, like inhibitory antibodies or fragments thereof, variants of HMGB1 comprising mutations in box A, or polymer conjugates of the box A domain have been described (US 6,468,533, WO 02/074337, US 2003/0144201, WO 2006024547, and WO 2008031612). On the other hand, HMGB1 was proposed as an anti-cancer agent (US 2011/0123483 A1).

For the HMGB1 proteins, several structural motifs have been described: two DNA-binding domains (box A and box B), two nuclear localization sequences, and a C-terminal acidic domain. The HMGB1 proteins can be extensively posttranslationally modified by acetylation, methylation, ADP-ribosylation, phosphorylation or glycosylation. Acetylation of the nuclear localization sites is the signal that causes the HMGB1 protein to be actively secreted from activated cells of the immune system. Besides active secretion, HMGB1 is also released passively from necrotic cells.

The enzyme pyruvate kinase M2 (PKM2) was recently identified as a specific target for cancer therapy, which is in particular produced in cancer cells. PKM2 is a pacemaker enzyme of glycolysis and occurs in two forms: the tetrameric form serves in the aerobic degradation of glucose and has a low $K_m$ value for its substrate phosphoenolpyruvate (PEP); accordingly, the tetrameric form is highly active at physiological concentrations of PEP, causing channeling of glucose into energy metabolism. The dimeric form of PKM2 has a high $K_m$ value for PEP and is almost inactive at physiological concentrations of PEP, causing glycolytic intermediates before pyruvate to be channeled into synthetic processes.

Two groups of modulators of PKM2 are known: Inhibitors, e.g. specific phosphotyrosine-peptides, e.g. P-M2tide (tyrosine-phosphorylated peptide GGAVDDDYAQFANGG (SEQ ID NO:1)) cause dissociation of tetramers into the dimeric form. Activators, e.g. ML265 (CAS-NO: 1221186-53-3, 6-(3-aminobenzyl)-4-methyl-2-(methylsulfinyl)-4,6-dihydro-5H-thieno[2',3':4,5]pyrrolo[2,3-d]pyridazin-5-one), stabilize the tetrameric form of PKM2. Interestingly, inhibitors as well as activators of PKM2 were found to have anti-tumor activity; however, the compounds have to be used at high concentrations (approx. 100 µM or higher) in order to have an effect.

Cancer treatment, besides surgical removal of tumor tissue, essentially relies on the application of medicaments and/or treatments that exert a deleterious function on actively dividing cells. By its nature, such treatment will also harm non-tumor cells and tissues undergoing cell division in the human body, leading to most of the well-known and dreaded side effects of chemo- and radiotherapy, like nausea, digestive distortions, fatigue, hair loss, and more. It is, thus, desirable to have new therapeutic agents at hand that are effective via hitherto unknown routes of action, thereby potentially allowing a dose reduction in chemo- and/or radiotherapy, alleviating side-effects. The provision of such agents using new routes of cancer cell killing could also potentially contribute to the removal of cancer stem cells, which can survive chemotherapy by falling into a resting state and which were recently found to be responsible for at least a fraction of all relapses and metastases.

Accordingly, the present invention relates to a combined preparation comprising (i) a modulator of pyruvate kinase M2 (PKM2) activity, and (ii) an agent providing high mobility group box 1 (HMGB1) protein or a derivative thereof.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not noted otherwise, the term "about" relates to the indicated value ±20%.

The term "combined preparation", as referred to in this application, relates to a preparation comprising the pharmaceutically active compounds of the present invention in one preparation. Preferably, the combined preparation is comprised in a container, i.e. preferably, said container comprises all pharmaceutically active compounds of the present invention. Preferably, said container comprises the pharmaceutically active compounds of the present invention as separate formulations, i.e. preferably, one formulation of the modulator of PKM2 activity, and one formulation of the agent providing high mobility group box 1 (HMGB1) protein or a derivative thereof; more preferably, said container comprises the pharmaceutically active compounds of the present invention in a single formulation, e.g. preferably, as a two-layer-tablet, or the like. Most preferably, the combined preparation is a mixed formulation, i.e. preferably, the combined preparation comprises a mixture of the compounds of the present invention. As will be understood by the skilled person, the term "formulation" relates to a, preferably pharmaceutically acceptable, mixture of compounds, comprising or consisting of at least one pharmaceutically active compound of the present invention. Preferably, the combined preparation comprises a modulator of PKM2 activity and an agent providing high mobility group box 1 (HMGB1) protein or a derivative thereof in a single formulation, e.g. a tablet or infusion; more preferably, the combined preparation comprises a mixture of a modulator of PKM2 activity and an agent providing high mobility group box 1 (HMGB1) protein or a derivative thereof.

Preferably, the combined preparation is for separate or for combined administration. "Separate administration", as used herein, relates to an administration wherein at least two of the pharmaceutically active compounds of the present invention are administered via different routes. E.g. one compound may be administered by enteral administration (e.g. orally), whereas a second compound is administered by parenteral administration (e.g. intravenously). Preferably, the combined preparation for separate administration comprises at least two physically separated preparations for separate administration, wherein each preparation contains at least one pharmaceutically active compound; said alternative is preferred e.g. in cases where the pharmaceutically active compounds of the combined preparation have to be administered by different routes, e.g. parenterally and orally, due to their chemical or physiological properties. Conversely, "combined administration" relates to an administration wherein the pharmaceutically active compounds of the present invention are administered via the same route, e.g. orally or intravenously.

Also preferably, the combined preparation is for simultaneous or for sequential administration. "Simultaneous administration", as used herein, relates to an administration wherein the pharmaceutically active compounds of the present invention are administered at the same time, i.e., preferably, administration of the pharmaceutically active compounds starts within a time interval of less than 15 minutes, more preferably, within a time interval of less than 5 minutes. Most preferably, administration of the pharmaceutically active compounds starts at the same time, e.g. by swallowing a tablet comprising the pharmaceutically active compounds, or by applying an intravenous injection of a solution comprising the pharmaceutically active compounds. Conversely, "sequential administration", as used herein, relates to an administration causing plasma concentrations of the pharmaceutically active compounds in a subject enabling the synergistic effect of the present invention, but which, preferably, is not a simultaneous administration as specified herein above. Preferably, sequential administration is an administration wherein administration of the pharmaceutically active compounds, preferably all pharmaceutically active compounds, starts within a time interval of 1 or 2 days, more preferably within a time interval of 12 hours, still more preferably within a time interval of 4 hours, even more preferably within a time interval of one hour, most preferably within a time interval of 5 minutes.

Preferably, the combined preparation is a pharmaceutically compatible combined preparation. The terms "pharmaceutically compatible preparation" and "pharmaceutical composition", as used herein, relate to compositions comprising at least one compound of the present invention and optionally one or more pharmaceutically acceptable carrier. The compounds of the present invention can be formulated as pharmaceutically acceptable salts. Preferred acceptable salts are acetate, methylester, HCl, sulfate, chloride and the like. The pharmaceutical compositions are, preferably, administered topically or, more preferably, systemically. Suitable routes of administration conventionally used for drug administration are oral, intravenous, or parenteral administration as well as inhalation. However, depending on the nature and mode of action of a compound, the pharmaceutical compositions may be administered by other routes as well. Moreover, the compounds can be administered in combination with other drugs either in a common pharmaceutical composition or as separated pharmaceutical compositions as specified elsewhere herein, wherein said separated pharmaceutical compositions may be provided in form of a kit of parts.

The compounds are, preferably, administered in conventional dosage forms prepared by combining the drugs with standard pharmaceutical carriers according to conventional procedures. These procedures may involve mixing, granulating and compressing or dissolving the ingredients as appropriate for the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the compound or compounds. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depend upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Preferred doses and concentrations of the compounds of the present invention are specified elsewhere herein.

The pharmaceutical compositions and formulations referred to herein are, preferably, administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The term "derivative", as used in the context of a chemical compound of the present invention, relates to a chemical molecule having a structure related to said chemical compound of the present invention. Preferably, a derivative can be produced from a chemical compound of the present invention by at most three, more preferably at most two, most preferably at most one chemical derivatization reactions. Preferably, the derivative is a compound which is metabolized in a mammalian, preferably a human, body into a chemical compound of the present invention. Also preferably, a derivative is a compound from which a chemical compound of the present invention can be obtained by hydrolysis. In case the chemical compound is a peptide or a polypeptide, the derivative, preferably, is a compound having at least a degree of similarity as specified herein below to the compound it is derived from. As used herein, a derivative of the high mobility group box 1 (HMGB1) polypeptide as specified herein below or a derivative of Box B of the HMGB1 polypeptide as specified herein below has the activity of inhibiting cancer cells, preferably colon cancer cells, more preferably HCT116 cells and/or, preferably, of inhibiting the activity of the tetrameric form of PKM2.

The term "pyruvate kinase" or "PK" is understood by the skilled person and relates to an enzyme catalyzing the transfer of a phosphate group from phosphoenolpyruvate to ADP to yield ATP and pyruvate (EC 2.7.1.40). Vertebrates are known to comprise four isoforms of pyruvate kinase, of which two are encoded by the same gene, respectively. The human genes encoding pyruvate kinases are PKLR (Genbank Acc. No: NM_000298.5 GI:189095249) and PKM as specified herein below.

As used herein, the term "pyruvate kinase M" or "PKM" relates to one of the products of the PKM gene, preferably the human PKM gene. From the PKM gene, several splice-variants are transcribed, which give rise to isoenzymes. Isoform a, also referred to as Pyruvate kinase M1 (PKM1, Genbank Acc. No: NP_002645.3 GI:33286418, SEQ ID NO: 8) is a tetrameric enzyme with high affinity to the substrate phosphoenolpyruvate. A second isoform of pyruvate kinase M is referred to as "pyruvate kinase M2" or "PKM2". Thus, preferably, the PKM of the present invention is PKM2. Preferably, PKM2 is mammalian PKM2, more preferably human PKM2. Preferably, PKM2 comprises or, more preferably, consists of the amino acid sequence of Genbank Acc NO: AAQ15274.1 GI:33346925 (SEQ ID NO: 2), preferably encoded by a polynucleotide comprising or consisting of the nucleic acid sequence of Genbank Acc NO: KJ891817.1 GI:649102182 or SEQ ID NO: 3. PKM2 can exist in a, preferably non-phosphorylated, tetrameric form having a high affinity for its substrate phosphoenolpyruvate; and in a, preferably phosphorylated, dimeric form having a low affinity for its substrate phosphoenolpyruvate. Since conventional activity assays do not discriminate between PKM1 and the high-affinity form of PKM2, the terms "high-affinity pyruvate kinase", also referred to as "Pyruvate kinase high affinity" or "PKHA" include both of the aforesaid isoenzymes. In contrast, the term "low-affinity pyruvate kinase", also referred to as "Pyruvate kinase low affinity" or "PKLA" relates to the dimeric form of PKM2. Where necessary, for a specific reference to the high-affinity form of PKM2, the term "high-affinity PKM2" or "PKM2HA" is used.

The term "modulator of PKM2 activity", as used herein, relates to an agent modulating the activity of pyruvate kinase M2 (PKM2), i.e., preferably, the modulator causes the activity of PKM2 to increase or decrease by at least 10%, more preferably at least 25%, most preferably at least 50% if present at an effective concentration in an assay mixture determining activity of PKM2 known to the skilled person, preferably as specified herein below. The skilled person knows how to determine an effective concentration; preferably, an effective concentration of a modulator of PKM2 activity is of from 10 µM to 100 mM, more preferably of from 50 µM to 50 mM, most preferably of from 100 µM to 10 mM. As will be understood by the skilled person, activity of a candidate compound in modulating PKM2 activity is preferably determined in the absence of further modulators of PKM2 activity. Preferably, the modulator of PKM2 is a compound not produced by the body of a subject, more preferably a compound not being produced and/or consumed in glycolysis. Thus, the modulator of PKM2 activity is not an agent providing HMGB1 or a derivative thereof and, preferably, is not D-Fructose-1,6,bisphosphate. Preferably, the modulator of PKM2 activity is an inhibitor of PKM2 activity, more preferably, a compound destabilizing the tetrameric form of PKM2, even more preferably, is P-M2tide (tyrosine-phosphorylated peptide GGAVDDDYAQFANGG (SEQ ID NO:1)) or a derivative thereof, said derivative of P-M2tide having the activity of inhibiting PKM2 activity or providing a compound having said activity upon metabolization in the body of a subject. Also preferably, the modulator of PKM2 activity is an activator of PKM2 activity, more preferably, a compound stabilizing the tetrameric form of PKM2, even more preferably, is ML265 (CAS-NO: 1221186-53-3,6-(3-aminobenzyl)-4-methyl-2-(methylsulfinyl)-4,6-dihydro-5H-thieno[2',3':4,5]-pyrrolo[2,3-d]pyridazin-5-one) or DASA (1-(2,6-Difluorophenylsulfonyl)-4-(2,3-dihydrobenzo[b][1,4]dioxin-6-ylsulfonyl)piperazine). Accordingly, according to the present invention, a modulator of PKM2 activity is an agent modulating the equilibrium of the tetrameric and dimeric forms of PKM2.

Preferably, the modulator of PKM2 activity is used at a concentration of less than 0.1 mM, more preferably less than 0.05 mM, most preferably less than 0.01 mM; or, preferably, at a dose inducing a plasma concentration of less than 0.1 mM, more preferably less than 0.05 mM, most preferably less than 0.01 mM. Also preferably, the modulator of PKM2 activity is used at a concentration of from 0.0005 mM to 0.1 mM, more preferably of from 0.001 mM to 0.05 mM, most preferably of from 0.005 mM to 0.01 mM; or, preferably, at a dose inducing a plasma concentration of from 0.0005 mM to 0.1 mM, more preferably of from 0.001 mM to 0.05 mM, most preferably of from 0.005 mM to 0.01 mM.

As used herein, the term "High Mobility Group Box 1 polypeptide" (HMGB1 polypeptide) relates to a member of the high mobility group of polypeptides known to the skilled person; or to partial sequences or derivatives thereof having the activity of inhibiting the activity of the tetrameric form of PKM2. Preferably, the HMGB1 polypeptide is the human HMGB1 polypeptide (Genbank ACC No: NP002119.1 GI:4504425, SEQ ID NO: 4) or a partial sequence or a derivative thereof having the activity as specified above. Suitable assays for measuring the activities mentioned before are described in the accompanying Examples. The HMGB1 polypeptide may be purified from cells or tissues or it may be chemically synthesized or, preferably, can be recombinantly manufactured. The HMGB1 polypeptide may comprise further amino acids which may serve as a tag for purification or detection, and/or the HMGB1 polypeptide may be comprised by a fusion polypeptide, as specified elsewhere herein.

Preferred derivatives of the polypeptides of the present invention, including the HMGB1 polypeptide, are described elsewhere herein. In a preferred embodiment, a derivative of the HMGB1 polypeptide is a polypeptide comprising the B-box motif of the HMGB1 polypeptide, preferably comprising Box B of human HMGB1, more preferably comprising SEQ ID NO: 5 or a derivative thereof, more preferably comprising the polyphosphorylated Box B of human HMGB1, preferably as specified herein below.

Preferably, the HMGB1 polypeptide is phosphorylated, more preferably tyrosine-phosphorylated at at least one, preferably at at least two, more preferably at at least three, most preferably at all four positions selected from Y109, Y144, Y155 and Y162. Also preferably, the polypeptide comprising the B-box motif of the HMGB1 polypeptide is phosphorylated, more preferably tyrosine-phosphorylated at at least one, preferably at at least two, more preferably at at least three, most preferably at all four positions selected from the positions corresponding to Y109, Y144, Y155 and Y162 of the HMGB1 polypeptide. Accordingly, the term "polyphosphorylated HMGB1 polypeptide", as used herein, relates to a HMGB1 polypeptide being phosphorylated at at least two, preferably at least three, more preferably all four positions selected from the positions corresponding to Y109, Y144, Y155 and Y162 of the HMGB1 polypeptide. Most preferably, a polyphosphorylated HMGB1 polypeptide is an HMGB1 polypeptide being phosphorylated at the four aforesaid tyrosine residues and additionally being phosphorylated at at least one further residue, preferably serine and/or threonine residue, preferably within the B-Box of the polypeptide. Correspondingly, the term "derivative of polyphosphorylated HMGB1 polypeptide", as used herein, relates to a derivative of a HMGB1 polypeptide, as specified elsewhere herein, being phosphorylated at at least two, preferably at least three, more preferably all four positions selected from the positions corresponding to Y109, Y144, Y155 and Y162 of the HMGB1 polypeptide. Most preferably, a derivative of polyphosphorylated HMGB1 polypeptide is a derivative of an HMGB1 polypeptide being phosphorylated at the four aforesaid tyrosine residues and additionally being phosphorylated at at least one further residue, preferably serine and/or threonine residue, preferably within the B-Box of the polypeptide.

In a preferred embodiment, the HMGB1 polypeptide or derivative thereof is an oligophosphorylated HMGB1 polypeptide as specified herein below.

The term "agent providing HMGB1 polypeptide or a derivative thereof", as used herein, relates to any agent or composition having the capacity of releasing HMGB1 polypeptide or a derivative thereof as specified herein to a biological system. Preferably, the agent providing HMGB1 polypeptide or a derivative thereof is used at a dose inducing a plasma concentration of from 1 nM to 1000 nM, more preferably of from 10 nM to 250 nM, most preferably of from 25 nM to 150 nM.

In a preferred embodiment, the agent providing HMGB1 polypeptide or derivative thereof is an agent providing oligophosphorylated HMGB1 polypeptide as specified herein below.

Preferably, said agent providing HMGB1 polypeptide or a derivative thereof is the HMGB1 polypeptide itself or a derivative thereof as specified herein; the term, preferably, further includes a polypeptide having an amino acid sequence at least 70% identical to the HMGB1 polypeptide or to Box B of the HMGB1 polypeptide and having the activity of inhibiting the activity of the tetrameric form of PKM2. Preferably, the term also relates to an agent specifically binding to a tumor cell comprising the HMGB1 polypeptide or Box B of the HMGB1 polypeptide. Preferably, said agent specifically binding to a tumor cell is an antibody, an aptamer, a lectin, or the like. Also preferably, the term agent providing HMGB1 polypeptide or a derivative thereof relates to a HMGB1 secreting cell induced to secrete the HMGB1 polypeptide. Cells which can be induced to secrete HMGB1 and methods for doing so are known in the art and include, preferably, the methods as shown in the examples; preferred cells which can be induced to secrete HMGB1 are macrophages and NK cells. Also preferably, the term agent providing HMGB1 polypeptide or a derivative thereof relates to an expressible polynucleotide encoding the HMGB1 polypeptide and/or Box B of the HMGB1 polypeptide. As will be understood by the skilled person, said polynucleotide is, preferably, comprised in a vector or in a host cell.

The term "polynucleotide", as used herein, relates to a polynucleotide comprising a nucleic acid sequence which encodes a polypeptide having the biological activity as described above, preferably comprising the nucleotide sequence of SEQ ID NO: 6 and/or 7. Preferably, the polynucleotide is a polynucleotide encoding a polypeptide comprising the amino acid sequence of SEQ ID NO: 4 and/or 5 or a derivative thereof as specified herein above. It is to be understood that a polypeptide having an amino acid sequence as detailed above may also be encoded due to the degenerated genetic code by more than one species of polynucleotide. Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a polypeptide having the activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above.

Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptides of the present invention may be identified by a sequence comparison of the nucleic acid sequence of the polynucleotide or of the amino acid sequence of the polypeptides as specified above. Suitable PCR conditions are well known in the art. As a template, DNA or cDNA from AAVs may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences detailed above. The percent identity values are, preferably, calculated as set forth above.

A polynucleotide comprising a fragment of any of the aforementioned nucleic acid sequences is also encompassed as a polynucleotide of the present invention. The fragment shall encode a polypeptide which still has the biological activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The polynucleotide of the present invention shall be provided, preferably, either as an isolated polynucleotide (i.e. isolated from its natural context) or in genetically modified form. The polynucleotide, preferably, is DNA including cDNA or RNA. The term encompasses single as well as double stranded polynucleotides. Moreover, comprised are also chemically modified polynucleotides including naturally occurring modified polynucleotides such as glycosylated or methylated polynucleotides or artificially modified ones such as biotinylated polynucleotides.

The polynucleotides of the present invention either essentially consist of the aforementioned nucleic acid sequences or comprise the aforementioned nucleic acid sequences. Thus, they may contain further nucleic acid sequences as well. Specifically, the present invention also relates to a vector comprising the polynucleotide of the present invention.

The term "vector", preferably, encompasses phage, plasmid, viral or retroviral vectors as well as artificial chromosomes, such as bacterial or yeast artificial chromosomes. More preferably, the term relates to a vector derived from a virus, said virus, preferably, preferentially infecting tumor cells (tumorotropic virus) or a virus preferentially lysing cancer cells (oncolytic virus). Moreover, the term also relates to targeting constructs which allow for random or site-directed integration of the targeting construct into genomic DNA. Such targeting constructs, preferably, comprise DNA of sufficient length for either homologous or heterologous recombination. The vector encompassing the polynucleotide of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Viral vectors may be replication competent or replication defective.

Preferably, in the vector of the invention the polynucleotide of the invention is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may, preferably, comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

The term "host cell", preferably, relates to a cell compatible with being administered to a subject. More preferably, said cell is immunologically compatible with the subject. Most preferably, the cell is a cell which was obtained from said subject. The host cell of the current invention, preferably, is a cell with a tendency to migrate into the vicinity of cancer cells, More preferably, the host cell is an immune cell, and most preferably is a cell of the immune system specifically recognizing a tumor specific antigen, like, e.g. a tumor antigen specific T-cell.

In a preferred embodiment of a polypeptide or peptide of the present invention, the polypeptide or peptide further comprises a detectable tag. The term "detectable tag" refers to a stretch of amino acids which are added to or introduced into the polypeptide or peptide. Preferably, the tag shall be added C- or N-terminally to the polypeptide or peptide; said stretch of amino acids may, e.g., allow for detection of the polypeptide or peptide by an antibody which specifically recognizes the tag or it shall allow for forming a functional conformation, such as a chelator or it shall allow for visualization by fluorescent tags. Preferred tags are the Myc-tag, FLAG-tag, 6-His-tag, HA-tag, GST-tag or GFP-tag. These tags are all well known in the art.

Preferably, the term "derivative thereof" relating to a polypeptide or peptide includes variants of the amino acid sequence of said polypeptide or peptide, said variants having an amino acid sequence being at least 70%, at least 80%, at least 90%, at least 95%, least 96%, at least 97%, at least 98% or at least 99% identical to the amino acid sequence of the polypeptide or peptide and said variants retaining the function of the polypeptide or peptide as specified herein. The percent identity values are, preferably, calculated over the entire amino acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981)), which are part of the GCG software packet (Genetics Computer Group, 575 Science Drive, Madison, Wisconsin, USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000.

Moreover, derivatives of polypeptides or peptides further encompass variants of the aforementioned specific amino acid sequences which may represent orthologs, paralogs or other homologs of the specific polypeptides or peptides. The variants, preferably, comprise an amino acid sequence characterized in that the sequence can be derived from the aforementioned sequences of polypeptides or peptides described above by at least one amino acid substitution and/or addition and/or deletion.

The term derivative also includes chemically modified polypeptides, e.g., polypeptides containing modified amino acids or polypeptides which are, e.g., biotinylated, or are coupled to fluorophores, such as fluorescein, or Cy 3, are conformationally restricted, e.g. by disulfide bridging or by stapling (Walensky 2004, Science 305(5689): 1466-1470), or are linked to cell penetration polypeptides or protein transduction domains (Snyder 2004, Pharm Res 21(3): 389-393). Such modifications may improve the biological properties of the polypeptides, e.g., cell penetration, binding, stability, or may be used as detection labels.

Advantageously, it was found in the work underlying the present invention that in the combined preparations of the present invention, the two compounds comprised therein mediate a synergistic effect, among others permitting decreasing the dose required for a modulator of PKM2 activity required for achieving a therapeutical effect. Moreover, it was found that the resistance of cells to a modulator of PKM2 or to HMGB1 can be broken by providing a combination therapy and that occurrence of such resistance can be avoided by providing combined treatment.

The definitions made above apply mutatis mutandis to the following. Additional definitions and explanations made further below also apply for all embodiments described in this specification mutatis mutandis.

Accordingly, the present invention also relates to the combined preparation of the present invention for use as a medicament.

Further, the present invention relates to the combined preparation of the present invention, for use in the treatment of inappropriate cellular proliferation.

The term "inappropriate cellular proliferation", as used herein, refers to a disease of an animal, preferably man, characterized by inappropriate and/or uncontrolled growth by a group of body cells. This uncontrolled growth may be accompanied by intrusion into and destruction of surrounding tissue and possibly spread of inappropriately proliferating cells to other locations in the body. Preferably, said inappropriate cellular proliferation is cancer, and, preferably, said inappropriately proliferating cells are cancer cells. Thus, preferably, the combined preparation is for use in the treatment of cancer.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, Burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, gallbladder cancer, gastric cancer, gastrointestinal stromal tumor, gestational trophoblastic tumor, hairy cell leukemia, head and neck cancer, hepatocellular cancer, Hodgkin lymphoma, hypopharyngeal cancer, hypothalamic and visual pathway glioma, intraocular melanoma, Kaposi sarcoma, laryngeal cancer, medulloblastoma, medulloepithelioma, melanoma, Merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, Waldenström macroglobulinemia, and wilms tumor.

More preferably, the cancer is leukemia, lymphoma, HPV-related cancer, colorectal carcinoma, gastric cancer, pancreas cancer, lung cancer, brain cancer, or breast cancer. A preferred colorectal carcinoma is colon carcinoma. Even more preferably, the cancer is leukemia, most preferably chronic lymphocytic leukemia (CLL).

In accordance with the above, the present invention also relates to a modulator of PKM2 activity for use in a combination therapy against inappropriate cellular proliferation comprising administration of an agent providing HMGB1 or a derivative thereof.

Preferably, at least a fraction of the cells of said inappropriate cellular proliferation is resistant to treatment with HMGB1 or a derivative thereof; preferably, said fraction is at least 2%, more preferably at least 5%, even more preferably at least 25%, most preferably at least 50%. The term "resistant to treatment" is understood by the skilled person and, preferably, relates to an inappropriate cellular proliferation wherein at least 75%, more preferably at least 90% of the cells of said inappropriate cellular proliferation are viable after 24 h in vivo treatment with the compound under investigation at a clinically relevant concentration; preferably, the clinically relevant concentration is 80 nM for HMGB1 or a derivative thereof, and is 100 µM for a modulator of PKM2 activity.

Also in accordance with the above, the present invention relates to an agent providing HMGB1 or a derivative thereof for use in a combination therapy against inappropriate cellular proliferation comprising administration of a modulator of PKM2 activity.

Preferably, at least a fraction of the cells of said inappropriate cellular proliferation is resistant to treatment with a modulator of PKM2 activity; preferably, said fraction is at least 2%, more preferably at least 5%, even more preferably at least 25%, most preferably at least 50%.

Preferably, the treatment wherein said method is a method for preventing selection of cells in said inappropriate cellular proliferation which are (i) resistant to treatment with a modulator of PKM2 activity or (ii) resistant to treatment with an agent providing HMGB1 or a derivative thereof.

Preferably, the compounds of the present invention are for use in preventing selection of cells in an inappropriate cellular proliferation which are (i) resistant to treatment with a modulator of PKM2 activity or (ii) resistant to treatment with an agent providing HMGB1 or a derivative thereof.

Also, the present invention relates to a method of treating inappropriate cellular proliferation in a subject suffering from inappropriate cellular proliferation comprising administering a modulator of PKM2 activity and an agent providing HMGB1 or a derivative thereof, thereby treating inappropriate cellular proliferation.

The method of treating inappropriate cellular proliferation of the present invention, preferably, is an in vivo method. Moreover, it may comprise steps in addition to those explicitly mentioned above. For example, further steps may relate, e.g., to surgically removing tumor tissue before or after administration of said pharmaceutically active compounds. Moreover, one or more of said steps may be performed by automated equipment.

The term "subject", as used herein, relates to an animal, preferably a farm or companion animal, more preferably a mammal, most preferably a human.

The term "treating" refers to ameliorating the diseases or disorders referred to herein or the symptoms accompanied therewith to a significant extent. Said treating as used herein also includes, preferably, an entire restoration of the health with respect to the diseases or disorders referred to herein. It is to be understood that treating as used in accordance with the present invention may not be effective in all subjects to be treated. However, the term shall, preferably, require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

The present invention also relates to the use of a modulator of PKM2 activity and an agent providing HMGB1 or a derivative thereof for the manufacture of a pharmaceutical composition or of a kit for the treatment of cancer.

Moreover, the present invention relates to a process for the preparation of a combined preparation according to the present invention, comprising the step of mixing a modulator of PKM2 activity and an agent providing HMGB1 or a derivative thereof. Preferably, said method further comprises the step of formulating the mixture of a modulator of PKM2 activity and a HMGB1 or a fragment or derivative thereof as a pharmaceutical composition.

The present invention also relates to a pharmaceutical composition comprising a modulator of PKM2 activity and an agent providing HMGB1 or a derivative thereof and a pharmaceutically acceptable carrier and to a kit comprising a modulator of PKM2 activity and an agent providing HMGB1 or a derivative thereof.

The term "kit" as used herein refers to a collection comprising at least the aforementioned means, e.g., a modulator of PKM2 activity and an agent providing HMGB1 or a derivative thereof, preferably, provided separately or combined, preferably within a single container. The container, also preferably, further comprises instructions for carrying out the method of the present invention. The components of the kit are provided, preferably, in a "ready-to-use" manner, e.g., concentrations are adjusted accordingly, etc.

The present invention further relates to an oligophosphorylated HMGB1 polypeptide or derivative thereof, wherein at least one of the tyrosine residues corresponding to amino acids Y109, Y144, Y155 and Y162 of the HMGB1 polypeptide was exchanged for a non-phosphorylatable amino acid.

Further, the present invention relates to an oligophosphorylated HMGB1 polypeptide or derivative thereof for treating disease; and the present invention relates to an oligophosphorylated HMGB1 polypeptide or derivative thereof for treating inappropriate cellular proliferation.

As used herein, the term "oligophosphorylated HMGB1 polypeptide" relates to a HMGB1 polypeptide as specified herein above in which at least one of the tyrosine residues corresponding to amino acids Y109, Y144, Y155 and Y162 of the HMGB1 polypeptide was exchanged for a non-phosphorylatable amino acid. Thus, compared to the wildtype HMGB1 polypeptide, the oligophosphorylated derivative of the HMGB1 polypeptide lacks at least one of the aforesaid potential phosphorylation sites. As will be understood, the term "oligophosphorylated" relates to a polypeptide providing less potential sites of phosphorylation, immaterial to which extent phosphorylation sites are actually phosphorylated in the wildtype HMGB1 polypeptide and/or the oligophosphorylated HMGB1 polypeptide. The oligophosphorylated HMGB1 polypeptide or derivative thereof still has the activity of inducing cell death in carcinoma cell lines. The activity of a compound to induce cell death can be established by the skilled person, preferably by comparing cell viability in a cell culture treated with said compound to an untreated control. Preferably, said activity is established by determining lactate dehydrogenase release, more preferably as specified herein in the Examples, most preferably using cell line SW480, which is available e.g. from the European Collection of Authenticated Cell Cultures (ECACC) under reference NO: SW 480 (ECACC 87092801). Preferably, at least the tyrosine residue corresponding to amino acid Y109 is exchanged, preferably to one of the amino acid specified above, more preferably to glutamine. Preferably, at least the tyrosine residue corresponding to amino acid Y144 is exchanged, preferably to one of the amino acid specified above, more preferably to glutamine. Preferably, at least the tyrosine residue corresponding to amino acid Y155 is exchanged, preferably to one of the amino acid specified above, more preferably to glutamine. Preferably, at least the tyrosine residue corresponding to amino acid Y162 is exchanged, preferably to one of the amino acid specified above, more preferably to glutamine. Preferably, at least the tyrosine residues corresponding to amino acids Y109 and Y144 are exchanged, preferably to amino acids independently selected from the amino acids specified above, more preferably to glutamine. Preferably, at least the tyrosine residues corresponding to amino acids Y109 and Y155 are exchanged, preferably to amino acids independently selected from the amino acids specified above, more preferably to glutamine. Preferably, at least the tyrosine residues corresponding to amino acids Y109 and Y162 are exchanged, preferably to amino acids independently selected from the amino acids specified above, more preferably to glutamine. Preferably, at least the tyrosine residues corresponding to amino acids Y144 and Y155 are exchanged, preferably to amino acids independently selected from the amino acids specified above, more preferably to glutamine. Preferably, at least the tyrosine residues corresponding to amino acids Y144 and Y162 are exchanged, preferably to amino acids independently selected from the amino acids specified above, more preferably to glutamine. Preferably, at least the tyrosine residues corresponding to amino acids Y155 and Y162 are exchanged, preferably to amino acids independently selected from the amino acids specified above, more preferably to glutamine. Preferably, at least the tyrosine residues corresponding to amino acids Y109, Y144 and Y155 are exchanged, preferably to amino acids independently selected from the amino acids specified above, more preferably to glutamine. Preferably, at least the tyrosine residues corresponding to amino acids Y109, Y144 and Y162 are exchanged, preferably to amino acids independently selected from the amino acids specified above, more preferably to glutamine. Preferably, at least the tyrosine residues corresponding to amino acids Y109, Y155 and Y162 are exchanged, preferably to amino acids independently selected from the amino acids specified above, more preferably to glutamine. Preferably, at least the tyrosine residues corresponding to amino acids Y144, Y155, and Y162 are exchanged, preferably to amino acids independently selected from the amino acids specified above, more preferably to glutamine. More preferably, at least the tyrosine residues corresponding to amino acids Y109, Y144, Y155, and Y162 are exchanged, preferably to amino acids independently selected from the amino acids specified above, more preferably to glutamine. Most preferably, the tyrosine residues corresponding to amino acids Y109, Y144, Y155, and Y162 are exchanged, preferably to amino acids independently selected from the amino acids specified above, more preferably to glutamine. Thus, preferably, the oligophosphorylated HMGB1 polypeptide or derivative thereof is a polypeptide comprising the amino acid sequence of SEQ ID NO:11, more preferably of SEQ ID NO:12.

The term "non-phosphorylatable amino acid", as used herein, relates to an amino acid for which post-translational phosphorylation is known not to occur in a eukaryotic cell, preferably is not known to occur in a living cell. Post-translational phosphorylation is known to occur in eukaryotic organisms on serine, threonine, tyrosine, arginine, lysine, and cysteine residues in eukaryotic cells, and additionally on histidine residues in prokaryotic cell. Accordingly, the non-phosphorylatable amino acid, preferably, is a proteinogenic amino acid which is not serine, threonine, tyrosine, arginine, lysine, cysteine, or histidine. Preferably, the non-phosphorylatable amino acid is an amino acid with a non-charged side chain, preferably is alanine, valine, leucine, isoleucine, phenylalanine, tryptophan, asparagine, or glutamine, preferably is alanine, valine, leucine, isoleucine, phenylalanine, asparagine, or glutamine, even more preferably, is alanine, valine, leucine, isoleucine, phenylalanine, tryptophan, asparagine, or glutamine. More preferably, the non-phosphorylatable amino acid is an amino acid with a non-charged side chain having a similar size to the side chain of tyrosine, more preferably is phenylalanine or glutamine, most preferably is glutamine.

Further, the present invention relates to a method for determining whether a subject suffering from inappropriate cellular proliferation is amenable to a treatment comprising administration of a modulator of PKM2 activity as the only PKM2 modulator, comprising (a) providing a sample of inappropriately proliferating cells of said subject (b) incubating a first subportion of said inappropriately proliferating cells under an atmosphere comprising at least 15% oxygen for at least 12 hours (normoxic subportion), (c) incubating a second subportion of said inappropriately proliferating cells under an atmosphere comprising at most 5% oxygen for at least 12 hours (hypoxic subportion), (d) determining the activities of at least the enzymes high-affinity Pyruvate Kinase and low-affinity Pyruvate Kinase in cells of said first and second subportions, (e) comparing said activities determined in step (d), and (f) based on the result of comparison step (e), determining whether said subject suffering from inappropriate cellular proliferation is being amenable to a treatment comprising administration of a modulator of PKM2 activity as the only PKM2 modulator.

The method for determining whether a subject suffering from inappropriate cellular proliferation is amenable to a treatment comprising administration of a modulator of PKM2 activity as the only PKM2 inhibitor of the present invention, preferably, is an in vitro method. Moreover, it may comprise steps in addition to those explicitly mentioned above. For example, further steps may relate, e.g., to deciding whether said subject is suffering from inappropriate cellular proliferation by methods known to the skilled person. Moreover, one or more of said steps may be performed by automated equipment. Preferably, the method for determining whether a subject suffering from inappropriate cellular proliferation is amenable to a treatment comprising administration of a modulator of PKM2 activity as the only PKM2 inhibitor is performed as described in EP 2 821 790 A1, which is herewith incorporated by reference with respect to its complete disclosure.

The term "sample" refers to a sample of a body fluid, to a sample of separated cells or to a sample from a tissue or an organ or to a sample of wash/rinse fluid obtained from an outer or inner body surface. The sample comprises cells, preferably the sample comprises inappropriately proliferating cells. Samples can be obtained by well known techniques and include, preferably, scrapes, swabs or biopsies from any body surface, body cavity, organ or tissue. Such samples can be obtained by use of brushes, (cotton) swabs, spatula, rinse/wash fluids, punch biopsy devices, puncture of cavities with needles or surgical instrumentation. However, samples of blood, urine, saliva, lacrimal fluid, stool are also encompassed by the method of the present invention. Tissue or organ samples may be obtained from any tissue or organ by, e.g., biopsy or other surgical procedures. Separated cells may be obtained from the body fluids or the tissues or organs by separating techniques such as filtration, centrifugation or cell sorting. Preferably, cell, tissue or organ samples are obtained from those cells, tissues or organs which are known or suspected targets of inappropriate proliferation. It is to be understood that the sample may be further processed in order to carry out the method of the present invention, in particular as specified in the claims, the embodiments, and in the examples. Preferably, the sample is pre-treated to obtain viable cells comprised in said sample.

Preferably, subportions are obtained such that there is a high probability that there is a similar number of inappropriately proliferating cells in all subportions obtained, e.g. by providing tissue slices of similar size, preferably obtained from subsequent cuts; or by providing approximately equal amounts of small tissue cuttings, or by enzymatically digesting the sample (e.g. with trypsin) to isolate cells and providing similar cell numbers.

The term "incubate" is understood by the skilled person and, preferably relates to maintaining cells under conditions permissive for survival and/or proliferation of said cells. Preferred conditions for maintaining inappropriately proliferating cells are known to the skilled person. Preferably, incubation is for of from 6 h to 24 h, more preferably of from 7 h to 15 h, even more preferably of from 10 h to 14 h, most preferably 12 h±1 h. Preferably, the first subportion and the second subportion are incubated for the same time, i.e. the difference in incubation time between the first subportion and the second subportion, preferably, is at most 1 h, more preferably, is at most 0.5 h, even more preferably, is at most 0.25 h. Preferably, samples are preconditioned under standard cell culture conditions for at least 12 h, more preferably at least 18 h, most preferably for at least 24 h.

According to the present invention, at least a first subportion of the sample is incubated under normoxic conditions, i.e. under an atmosphere comprising oxygen at an amount approximately corresponding to the oxygen content in a cancer tissue (approx. 1% to 10%) or of the normal atmosphere (21% oxygen). Preferably, the oxygen concentration is at least 1%, more preferably at least 5%, more preferably at least 10%; most preferably, the oxygen concentration is 21%.

According to the present invention, at least a second subportion of the sample is incubated under hypoxic conditions, i.e. under an atmosphere comprising an oxygen concentration inducing a hypoxic response in the cell. Preferably, the oxygen concentration is at most 0.5%, more preferably at most 0.3%, even more preferably, at most 0.1%, most preferably, is 0%.

Preferably, normoxic and hypoxic conditions are selected such that a significant difference between said two oxygen concentrations is affecting the samples. Accordingly, the difference in oxygen concentration between normoxic and hypoxic conditions, preferably, is at least 1%, more preferably, is at least 2%, even more preferably is at least 10%, most preferably is at least 20%.

Methods of determining enzyme activities, in particular of high-affinity Pyruvate Kinase, low-affinity Pyruvate Kinase are known in the art. Preferably, in the method, additional enzyme activities are determined, in particular at least one of Hexokinase, Malate decarboxylase, Lactate dehydrogenase (LDH), and cytochrome c oxidizing Complex IV. Preferably, the activities of at least the enzymes high-affinity Pyruvate Kinase, low-affinity Pyruvate Kinase, and Lactate Dehydrogenase are determined. The enzyme activities can be measured as described in textbooks and known to the skilled person, e.g. from EP 2 821 790 A1. Table 1 summarizes potential assays and reaction conditions for determining relevant enzyme activities.

TABLE 1

Exemplary enzyme assays

| Enzyme activity determined | Substrates | Helper Enzyme | Reaction measured |
|---|---|---|---|
| Pyruvate kinase low affinity | 10 mM PEP 1 mM ADP 0.5 mM NADH | Lactate dehydrogenase Stock 6 U/mL | NADH-oxidation |
| Pyruvate kinase high affinity | 0.1 mM PEP 1 mM ADP 0.5 mM NADH | Lactate dehydrogenase 6 U/mL | NADH-oxidation |
| Lactate dehydrogenase | 1 mM pyruvate 0.5 mM NADH | | NADH-Oxidation |

Preferably, the activities determined are specific activities, i.e. activity per mass of protein (U/mg). It will be understood by the skilled person that the above assay for high-affinity PK does not differentiate between Pyruvate Kinase M1 (product of the PKM1 gene) activity and high-affinity Pyruvate Kinase M2 (product of the PKM2 gene) activity; accordingly, in the assay, the total activity of high-affinity Pyruvate kinase and low-affinity Pyruvate kinase will be determined, respectively.

According to the method of the present invention, a strong change in the activity of either PKHA or PKLA under hypoxic conditions as compared to the activity under normoxic conditions is indicative of a sample from a patient amenable to a treatment comprising administration of a modulator of PKM2 activity as the only PKM2 modulator. Preferably, said change may be an increase or a decrease; also preferably, said change is a change by a factor of at least 1.5, more preferably at least 2, most preferably at least 3. Conversely, a moderate or no change in the activity of either PKHA or PKLA under hypoxic conditions as compared to the activity under normoxic conditions, or a parallel change of both PKHA and PKLA, is indicative of a sample from a patient not amenable to a treatment comprising administration of a modulator of PKM2 activity as the only PKM2 modulator. Preferably, for said patient not amenable to a treatment comprising administration of a modulator of PKM2 activity as the only PKM2 modulator, combined treatment with HMGB1 as described elsewhere herein is recommended.

Preferably, the method step (e) is calculating the ratios of the enzyme activity in the hypoxic subportion to the enzyme activity in the normoxic subportion. More preferably, aforementioned method step (e) further comprises calculating a ratio of the sum of activities of anaerobic enzyme(s) to the sum of activities of aerobic enzyme(s).

If, e.g., the enzyme activities of the enzymes LDH, PKLA as anaerobic enzymes and the aerobic enzymes PKHA are determined in a tumor tissue of a patient, one may proceed as follows: In a first step, preferably, normalized hypoxic/normoxic enzyme activities ($X_N$, with X=enzyme of interest) are calculated: $LDH_N=LDH_{hypoxic}/LDH_{normoxic}$, $PKLA_N=PKLA_{hypoxic}/PKLA_{normoxic}$, and $PKHA_N=PKHA_{hypoxic}/PKHA_{normoxic}$. Further, preferably, the anaerobic/aerobic ratio S may be calculated according to, e.g., the following equation:

$$S = \frac{LDH_N + PKLA_N}{PKHA_N} \quad \text{(eq. 1)}$$

As will be understood from the above, a value of S corresponding to the number of summands in the dividend, divided by the number of summands in the divisor in the formula applied for calculating S (reference score $S_R$), is indicative of a sample from a patient not amenable to a treatment comprising administration of a modulator of PKM2 activity as the only PKM2 modulator; preferably, S corresponds to $S_R \pm 0.5 S_R$, more preferably $\pm 0.25 S_R$, most preferably $\pm 0.1 S_R$ in such case. Conversely, a value of S strongly deviating from $S_R$ is indicative of a sample from a patient amenable to a treatment comprising administration of a modulator of PKM2 activity as the only PKM2 modulator; Preferably, S is higher or lower than $S_R \pm 0.1 S_R$, more preferably $\pm 0.25 S_R$, most preferably $\pm 0.5 S_R$ in such case. In the example of eq. 1, $S_R$ is $2((1+1)/1)$.

Further, the present invention relates to a method of treating inappropriate cellular proliferation in a subject suffering thereof comprising (A) determining whether said subject is being amenable to a treatment comprising administration of a modulator of PKM2 activity as the only PKM2 modulator, preferably by the method according to the present invention, and (B) administering to said subject a modulator of PKM2 activity in case said subject is determined to be amenable to a treatment comprising administration of a modulator of PKM2 activity as the only PKM2 inhibitor in step A), thereby treating inappropriate cellular proliferation.

The method of treating inappropriate cellular proliferation, preferably, is an in vivo method. Moreover, it may comprise steps in addition to those explicitly mentioned above. For example, further steps may relate, e.g., to deciding whether said subject is suffering from inappropriate cellular proliferation by methods known to the skilled person. Moreover, one or more of said steps may be performed by automated equipment. Preferably, the method comprises the further step of (C) administering to said subject a modulator of PKM2 activity and a HMGB1 or a fragment or derivative thereof, preferably the combined preparation of the present invention, in case said subject is determined not to be amenable to a treatment comprising administration of a modulator of PKM2 activity as the only PKM2 inhibitor in step A), thereby treating inappropriate cellular proliferation.

Advantageously, it was found in the experiments underlying the present invention that the differential activity of the enzymes specified above in tumor samples incubated under normoxic conditions compared to the activities under hypoxic conditions are indicative of whether the cells comprised therein are sensitive to a modulator of PKM2.

In view of the above, the following embodiments are preferred:

1. A combined preparation comprising
   (i) a modulator of pyruvate kinase M2 (PKM2) activity, and
   (ii) an agent providing high mobility group box 1 (HMGB1) polypeptide or a derivative thereof.
2. The combined preparation of embodiment 1, wherein said HMGB1 or derivative thereof inhibits activity of the tetrameric form of high affinity pyruvate kinase, preferably of PKM2.
3. The combined preparation of embodiment 1 or 2, wherein said agent providing HMGB1 polypeptide or a derivative thereof is
   (i) a polypeptide comprising a HMGB1 polypeptide,
   (ii) a polypeptide comprising Box B of the HMGB1 polypeptide,
   (iii) a polypeptide having an amino acid sequence at least 70% identical to the polypeptide of (i) or (ii) and having the activity of inhibiting the activity of the tetrameric form of PKM, preferably PKM2.
   (iv) an agent specifically binding to a tumor cell comprising the polypeptide of any one of (i) to (iii),
   (v) a HMGB1 secreting cell induced to secrete HMGB1 polypeptide,
   (vi) an expressible polynucleotide encoding the polypeptide of (i), (ii), and/or (iii), preferably comprised in a vector and/or in a host cell; or
   (vii) any combination of (i) to (vi).
4. The combined preparation of any one of embodiments 1 to 3, wherein said HMGB1 polypeptide of (i) is the human HMGB1 polypeptide, preferably comprising the amino acid sequence of SEQ ID NO: 4.
5. The combined preparation of any one of embodiments 3 to 4, wherein said Box B of the HMGB1 polypeptide of (ii) is Box B of the human HMGB1 polypeptide, preferably comprising the amino acid sequence of SEQ ID NO: 5.
6. The combined preparation of any one of embodiments 3 to 5, wherein said polypeptide of (i), (ii), or (iii) is a fusion polypeptide.
7. The combined preparation of any one of embodiments 3 to 6, wherein said HMGB1 secreting cell of (iv) is a macrophage or an NK cell.
8. The combined preparation of any one of embodiments 3 to 7, wherein said expressible polynucleotide of (vi) is a polynucleotide comprising
   (I) the nucleic acid sequence of SEQ ID NO: 6 and/or 7, or
   (II) a nucleic acid sequence at least 70% identical to the nucleic acid sequence of (I),
   and a promoter, preferably a heterologous promoter.
9. The combined preparation of any one of embodiments 3 to 8, wherein said agent specifically binding to a tumor cell of (iv) is an antibody or a fragment thereof or an aptamer.
10. The combined preparation of any one of embodiments 3 to 9, wherein said vector of (vi) is a viral vector, preferably an oncotropic viral vector.
11. The combined preparation of any one of embodiments 3 to 10, wherein said host cell is an immune cell, preferably tumor-specific B-cell.
12. The combined preparation of any one of embodiments 1 to 11, wherein said HMGB1 is phosphorylated HMGB1 and/or wherein said Box B of the HMGB1 polypeptide is phosphorylated Box B of the HMGB1 polypeptide.
13. The combined preparation of any one of embodiments 1 to 12, wherein said modulator of PKM2 is an inhibitor of PKM2, preferably an inhibitor of tetramerization of PKM2, more preferably P-M2tide (tyrosine-phosphorylated SEQ ID NO: 1).
14. The combined preparation of any one of embodiments 1 to 13, wherein said modulator is an activator of PKM2, preferably an agent stabilizing PKM2 tetramers, more preferably ML265 (6-(3-aminobenzyl)-4-methyl-2-(methylsulfinyl)-4,6-dihydro-5H-thieno[2',3':4,5]pyrrolo[2,3-d]pyridazin-5-one).
15. The combined preparation of any one of embodiments 1 to 14, wherein said PKM2 is human PKM2.
16. The combined preparation of any one of embodiments 1 to 15, wherein said combined preparation is for combined or separate and/or for simultaneous or sequential use.
17. The combined preparation of any one of embodiments 1 to 16, wherein said combined preparation is a pharmaceutically compatible preparation.
18. A combined preparation according to any one of embodiments 1 to 17 for use as a medicament.
19. A combined preparation according to any one of embodiments 1 to 17 for use in the treatment of inappropriate cellular proliferation, preferably cancer.
20. A modulator of PKM2 activity for use in a combination therapy against inappropriate cellular proliferation comprising administration of an agent providing HMGB1 or a derivative thereof.
21. The modulator of PKM2 activity for use of embodiment 20, wherein said inappropriate cellular proliferation is resistant to treatment with HMGB1 or a derivative thereof.
22. An agent providing HMGB1 or a derivative thereof for use in a combination therapy against inappropriate cellular proliferation comprising administration of a modulator of PKM2 activity.
23. The agent providing HMGB1 or a derivative thereof for use of embodiment 22, wherein said inappropriate cellular proliferation is resistant to treatment with a modulator of PKM2 activity.
24. The combined preparation for use according to any one of embodiments 1 to 17 for use in preventing selection of cells in an inappropriate cellular proliferation which are (i) resistant to treatment with a modulator of PKM2 activity or (ii) resistant to treatment with an agent providing HMGB1 or a derivative thereof.
25. The combined preparation for use according to embodiment 19 or the modulator of PKM2 activity for use of embodiment 20 or 21, wherein said modulator of PKM2 activity is used at a concentration of less than 0.1 mM, preferably less than 0.05 mM, more preferably less than 0.01 mM; or at a dose inducing a plasma concentration of less than 0.1 mM, preferably less than 0.05 mM, more preferably less than 0.01 mM.
26. The combined preparation for use according to embodiment 19 or the modulator of PKM2 activity for use of embodiment 20 or 21, wherein said modulator of PKM2 activity is used at a concentration of from 0.0005 mM to 0.1 mM, preferably of from 0.001 mM to 0.05 mM, more preferably of from 0.005 mM to 0.01 mM; or at a dose inducing a plasma concentration of from 0.0005 mM to 0.1 mM, preferably of from 0.001 mM to 0.05 mM, more preferably of from 0.005 mM to 0.01 mM.

27. The combined preparation for use according to embodiment 19, the modulator of PKM2 activity for use of embodiment 20 or 21, or the agent providing HMGB1 or a derivative thereof for use of embodiment 22 or 23, wherein said cancer is colorectal carcinoma or chronic lymphocytic leukemia (CLL).

28. A method of treating inappropriate cellular proliferation in a subject suffering from inappropriate cellular proliferation comprising administering a modulator of PKM2 activity and an agent providing HMGB1 or a derivative thereof, thereby treating inappropriate cellular proliferation.

29. Use of a modulator of PKM2 activity and an agent providing HMGB1 or a derivative thereof for the manufacture of a pharmaceutical composition or a kit for the treatment of cancer.

30. The use of embodiment 29, wherein said pharmaceutical composition is a combined composition according to any one of embodiments 1 to 17.

31. A process for the preparation of a combined preparation according to any one of embodiments 1 to 17, comprising the step of mixing a modulator of PKM2 activity and an agent providing HMGB1 or a derivative thereof.

32. The process of embodiment 31, further comprising the step of formulating the mixture of a modulator of PKM2 activity and an agent providing HMGB1 or a derivative thereof as a pharmaceutical composition.

33. A pharmaceutical composition comprising a modulator of PKM2 activity and an agent providing HMGB1 or a derivative thereof and a pharmaceutically acceptable carrier.

34. A kit comprising a modulator of PKM2 activity and an agent providing HMGB1 or a derivative thereof.

35. A method for determining whether a subject suffering from inappropriate cellular proliferation is amenable to a treatment comprising administration of a modulator of PKM2 activity as the only PKM2 inhibitor, comprising
   (a) providing a sample of inappropriately proliferating cells of said subject
   (b) incubating a first subportion of said inappropriately proliferating cells under an atmosphere comprising at least 1% oxygen for at least 12 h±1 h (normoxic conditions),
   (c) incubating a second subportion of said inappropriately proliferating cells under an atmosphere comprising at most 0.1% oxygen for at least 12 h±1 h (hypoxic conditions),
   (d) determining the activities of at least the enzymes high-affinity Pyruvate Kinase and low-affinity Pyruvate Kinase in cells of said first and second subportions,
   (e) comparing said activities determined in step (d), and
   (f) based on the result of comparison step (e), determining whether said subject suffering from inappropriate cellular proliferation is being amenable to a treatment comprising administration of a modulator of PKM2 activity as the only PKM2 inhibitor.

36. The method of embodiment 35, wherein a strong change in the activity of either PKHA or PKLA under hypoxic conditions as compared to the activity under normoxic conditions is indicative of a sample from a patient amenable to a treatment comprising administration of a modulator of PKM2 activity as the only PKM modulator.

37. The method of embodiment 35 or 36, wherein a moderate or no change in the activity of either PKHA or PKLA under hypoxic conditions as compared to the activity under normoxic conditions, or a parallel change of both PKHA and PKLA, is indicative of a sample from a patient not amenable to a treatment comprising administration of a modulator of PKM2 activity as the only PKM2 modulator.

38. A method of treating inappropriate cellular proliferation in a subject suffering thereof comprising
   (A) determining whether said subject is being amenable to a treatment comprising administration of a modulator of PKM2 activity as the only PKM2 inhibitor, preferably by the method according to any one of embodiments 35 to 37, and
   (B) administering to said subject a modulator of PKM2 activity as the only PKM2 inhibitor, in case said subject is determined to be amenable to a treatment comprising administration of a modulator of PKM2 activity as the only PKM2 inhibitor in step A), thereby treating inappropriate cellular proliferation.

39. The method of embodiment 39 further comprising
   (C) administering to said subject a modulator of PKM2 activity and a HMGB1 or a fragment or derivative thereof, preferably the combined preparation of any one of embodiments 1 to 17, in case said subject is determined not to be amenable to a treatment comprising administration of a modulator of PKM2 activity as the only PKM2 inhibitor in step A), thereby treating inappropriate cellular proliferation.

40. A polyphosphorylated High Mobility Group B1 (HMGB1) polypeptide or derivative thereof.

41. A polyphosphorylated HMGB1 polypeptide or derivative thereof for use as a medicament.

42. A polyphosphorylated HMGB1 polypeptide or derivative thereof for use in the treatment of cancer.

43. A combined preparation according to any one of embodiments 1 to 18, wherein said HMGB1 polypeptide or derivative thereof is a polyphosphorylated HMGB1 polypeptide or derivative thereof.

44. A method for treating a subject suffering from inappropriate cellular proliferation, preferably cancer, comprising administering to said subject a therapeutically effective dose of a polyphosphorylated HMGB1 polypeptide or derivative thereof.

45. A method of producing a polyphosphorylated HMGB1 polypeptide or derivative thereof, comprising
   (i) inducing peripheral blood monocytes, preferably NK cells, to produce HMGB1 or a derivative thereof; and
   (ii) purifying said HMGB1 or derivative thereof from the cell culture supernatant or from the cytosol of these cells.

46. The combined preparation according to any one of embodiments 1 to 11 or 13 to 17, the agent providing HMGB1 or a derivative thereof for use according to embodiment 22 or 23, the method according to embodiment 28, the use according to embodiment 29 or 30, the process according to embodiment 31 or 32, the pharmaceutical composition according to embodiment 33, the kit according to embodiment 34, wherein said derivative of the HMGB1 polypeptide is a polypeptide comprising Box B of the HMGB1 polypeptide in which at least one, preferably at least two, more preferably at least three, most preferably all four tyrosine residues corresponding to amino acids Y109, Y144, Y155 and Y162 of the HMGB1 polypeptide were exchanged to non-phosphorylatable amino acid residues, preferably glutamine residues, more preferably is a polypeptide comprising, more preferably consisting of, SEQ ID NO:11.

47. The combined preparation according to any one of embodiments 1 to 11 or 13 to 17, the agent providing HMGB1 or a derivative thereof for use according to embodiment 22 or 23, the method according to embodiment 28, the use according to embodiment 29 or 30, the process according to embodiment 31 or 32, the pharmaceutical composition according to embodiment 33, the kit according to embodiment 34, wherein said derivative of the HMGB1 polypeptide is a HMGB1 polypeptide in which at least one, more preferably at least two, even more preferably at least three, most preferably all four tyrosine residues Y109, Y144, Y155 and Y162 were exchanged to non-phosphorylatable amino acid residues, preferably glutamine residues, more preferably is a polypeptide comprising, more preferably consisting of, SEQ ID NO:12.

48. An oligophosphorylated HMGB1 polypeptide or derivative thereof, wherein at least one of the tyrosine residues corresponding to amino acids Y109, Y144, Y155 and Y162 of the HMGB1 polypeptide was exchanged for a non-phosphorylatable amino acid.

49. The oligophosphorylated HMGB1 polypeptide or derivative thereof of embodiment 48, wherein said non-phosphorylatable amino acid is an uncharged non-phosphorylatable amino acid.

50. The oligophosphorylated HMGB1 polypeptide or derivative thereof of embodiment 48 or 49, wherein said non-phosphorylatable amino acid in each case is independently selected from the groups consisting of alanine, valine, leucine, isoleucine, phenylalanine, tryptophan, asparagine, an glutamine, preferably is glutamine.

51. The oligophosphorylated HMGB1 polypeptide according to any one of embodiments 48 to 50 for use in treatment of disease.

52. The oligophosphorylated HMGB1 polypeptide according to any one of embodiments 48 to 50 for use in treatment of inappropriate cellular proliferation.

All references cited in this specification are herewith incorporated by reference with respect to their entire disclosure content and the disclosure content specifically mentioned in this specification.

FIGURE LEGENDS

FIG. 1: HMGB1 from human NK cells induces cell death in colorectal cancer. (A) HMGB1 was purified from NK-92 CI cells by chromatography. Arrow=HMGB1 containing fraction (eluate #38). (B) Immunoblot showing the membrane containing eluates 37-42. A specific HMGB1 band at 30 kD was detected only in eluate #38. (C) Cytotoxicity assay after 72 h incubation with HMGB1 (n=3). A 1:40 dilution of the purified HMGB1 (#38) was used (corresponding to approximately 16 nM). Recombinant human HMGB1 was used at 80 nM. (D) Supernatants from activated human peripheral blood NK cells (cross-linked with anti-Nkp30 antibody) from two donors were tested for their cytotoxic capacity in a crystal violet assay (72h, n=3). Glycyrrhizin (200 µM) was used as an inhibitor of HMGB1. (E) Immunoblot of the supernatants used in (D). HMGB1 was specifically secreted upon Nkp30 crosslinking. *=non-specific band. p<0.002. (F) to (M) NK cell derived HMGB1 induces cell death in colorectal cancer. (F, G) HMGB1 from cytotoxic granules from NK-92 CI cell line was purified by reversed phase chromatography on a Resource RPC column (F) and on a Source 15RPC ST 4.6/100 column (G) before the final purification step. Details are given in the Experimental Procedures section. The dashed line indicates the acetonitrile gradient. HMGB1 containing fractions are indicated by arrows. (H) The purification yield was approx. 90% as determined by Commassie Blue staining of the corresponding gel. (I, left) Survival of HT29 cancer cells as assessed by crystal violet viability assay. Cells were treated with recombinant human HMGB1 (160 nM) or NK cell derived HMGB1 (160 nM); where indicated 200 µM glycyrrhizin was used (72h, n=3). (I, right) Side-by-side comparison of HMGB1 cytotoxicity was performed using 80 nM HMGB1 concentrations (72 h, n=3). (K) Silver gel showing purity of HMGB1 in eluate #38 (0.5 µg protein loaded). (L) HPLC-purified HMGB1 (80 nM, 24 h, n=3) from the supernatant of Nkp30 stimulated blood donor NK cells was diluted in the IgG1 control supernatant and shows substantial cytotoxicity. (M) Interferon gamma concentration was determined by ELISA (see Experimental Procedures) and used as a positive control for the activation of the cultured and stimulated NK cells derived from blood donors. Error bars represent the SD. p<0.002.

Figure 2:
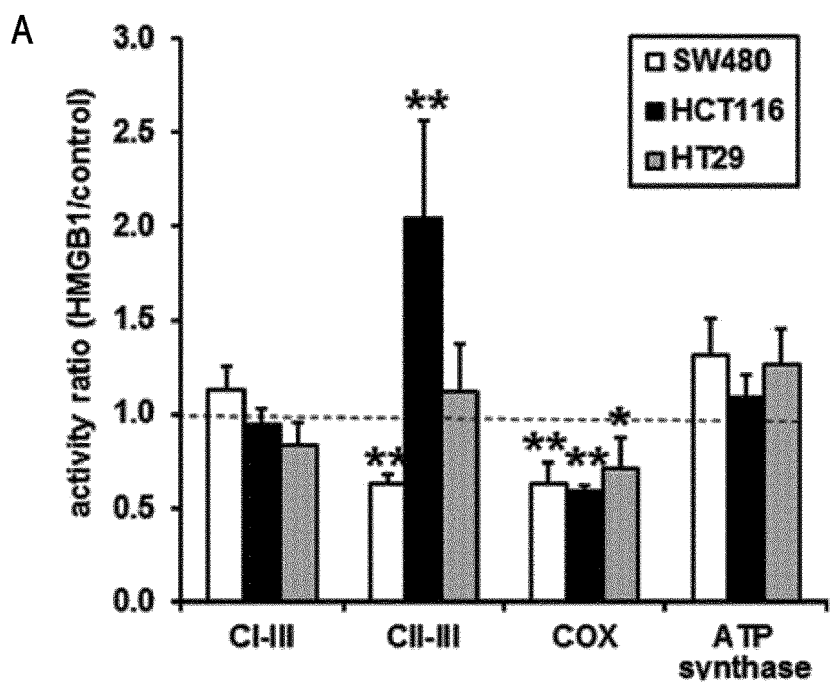
Figure 2:
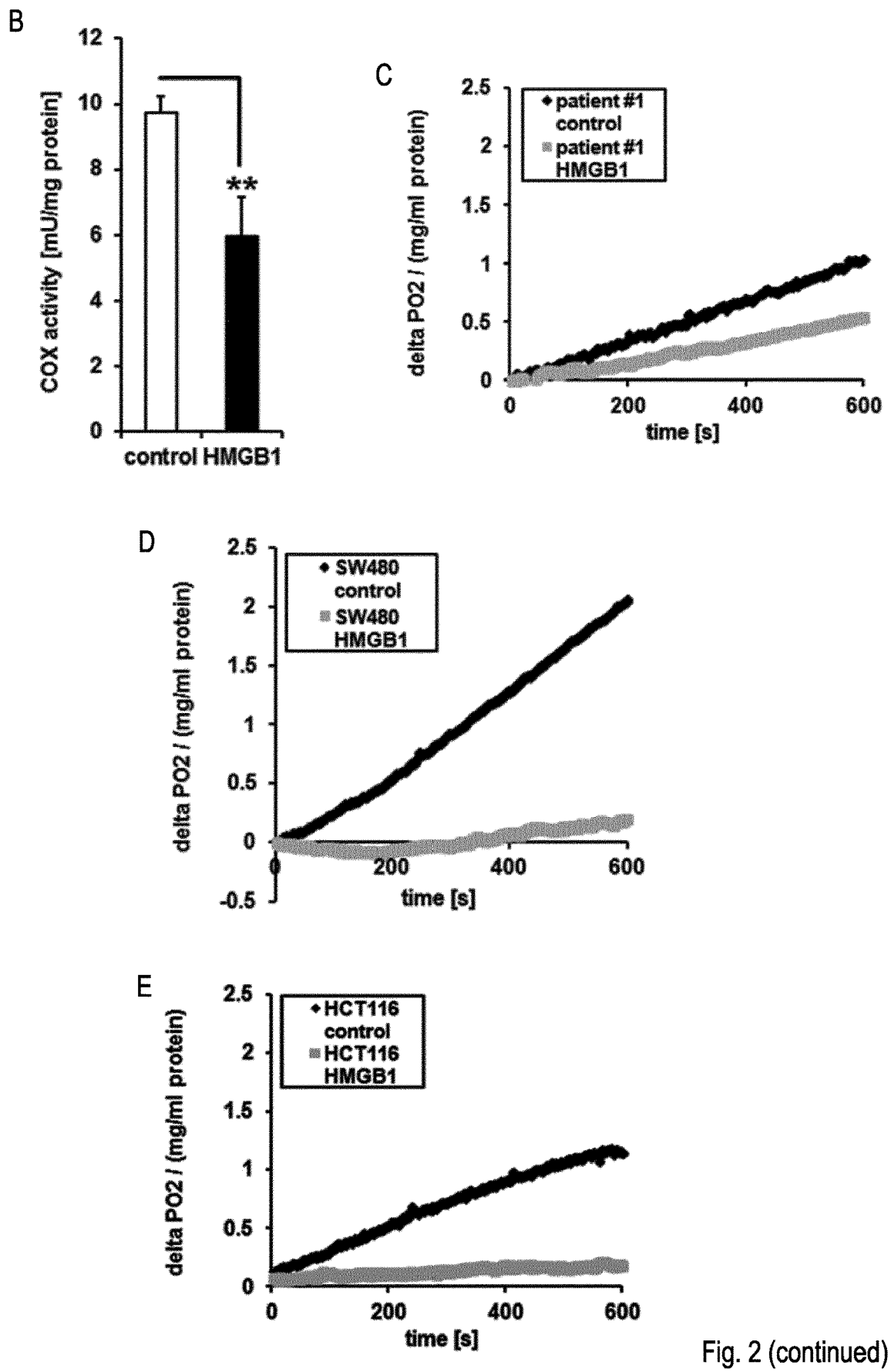
Figure 2:
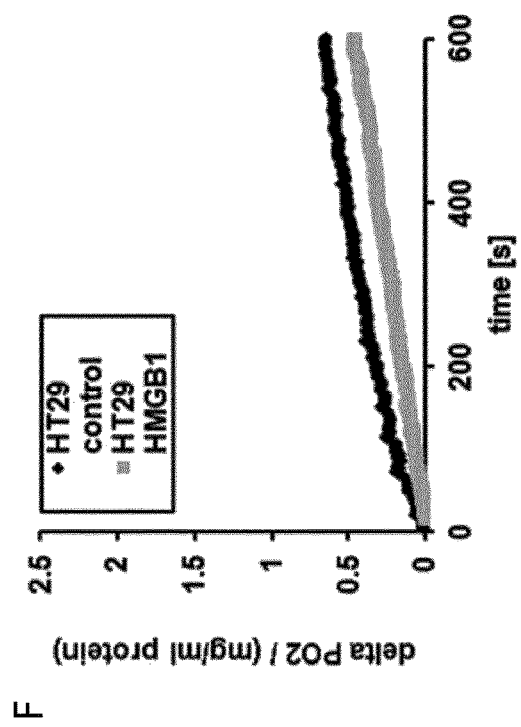

FIG. 2: HMGB1 inhibits mitochondrial respiration. (A) Activities of respiratory chain complexes measured in mitochondrial fractions of colorectal cancer cell lines after treatment with HMGB1 (80 nM, 24 h, n=5). (B) Tissue slices were generated from a fresh surgical human colon carcinoma specimen and treated with HMGB1 (160 nM, 72 h). After homogenization of tissue slices, COX activity was measured in the mitochondrial fractions (n=8). (C-F) Colorectal cancer cells and tissue slices were treated with HMGB1 as described in (A) and (B), respectively. Then, cyanide sensitive respiration was measured. *p<0.05, **p<0.001.

Figure 3:
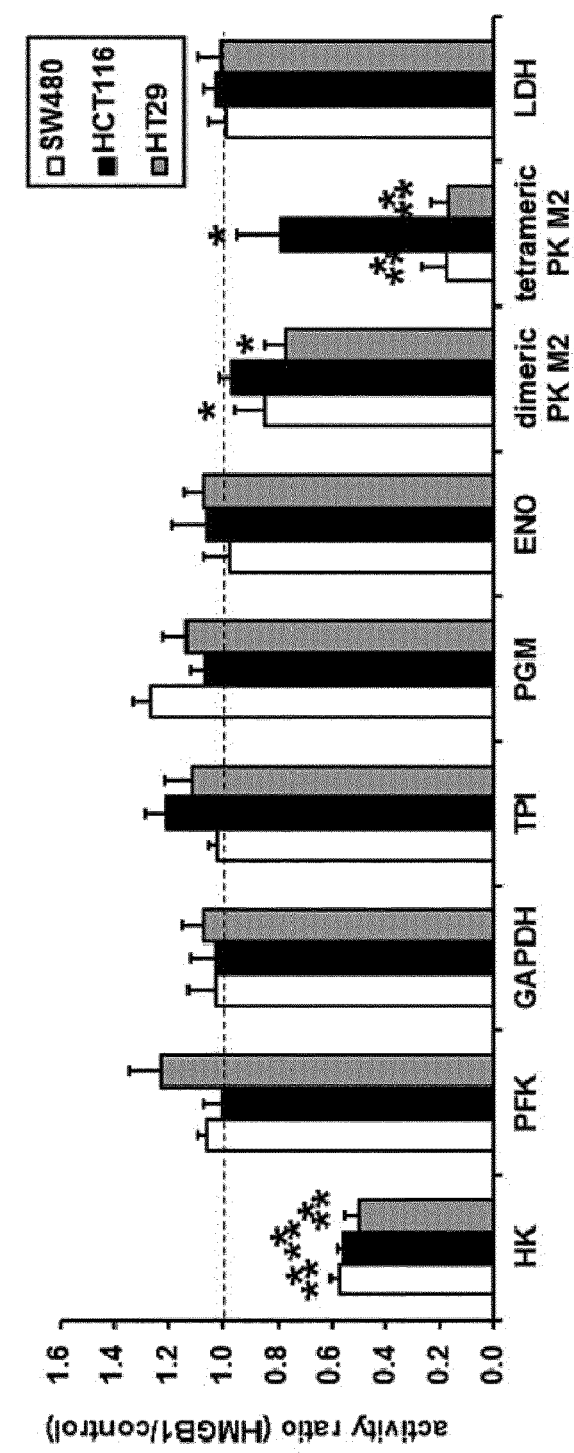
Figure 3:
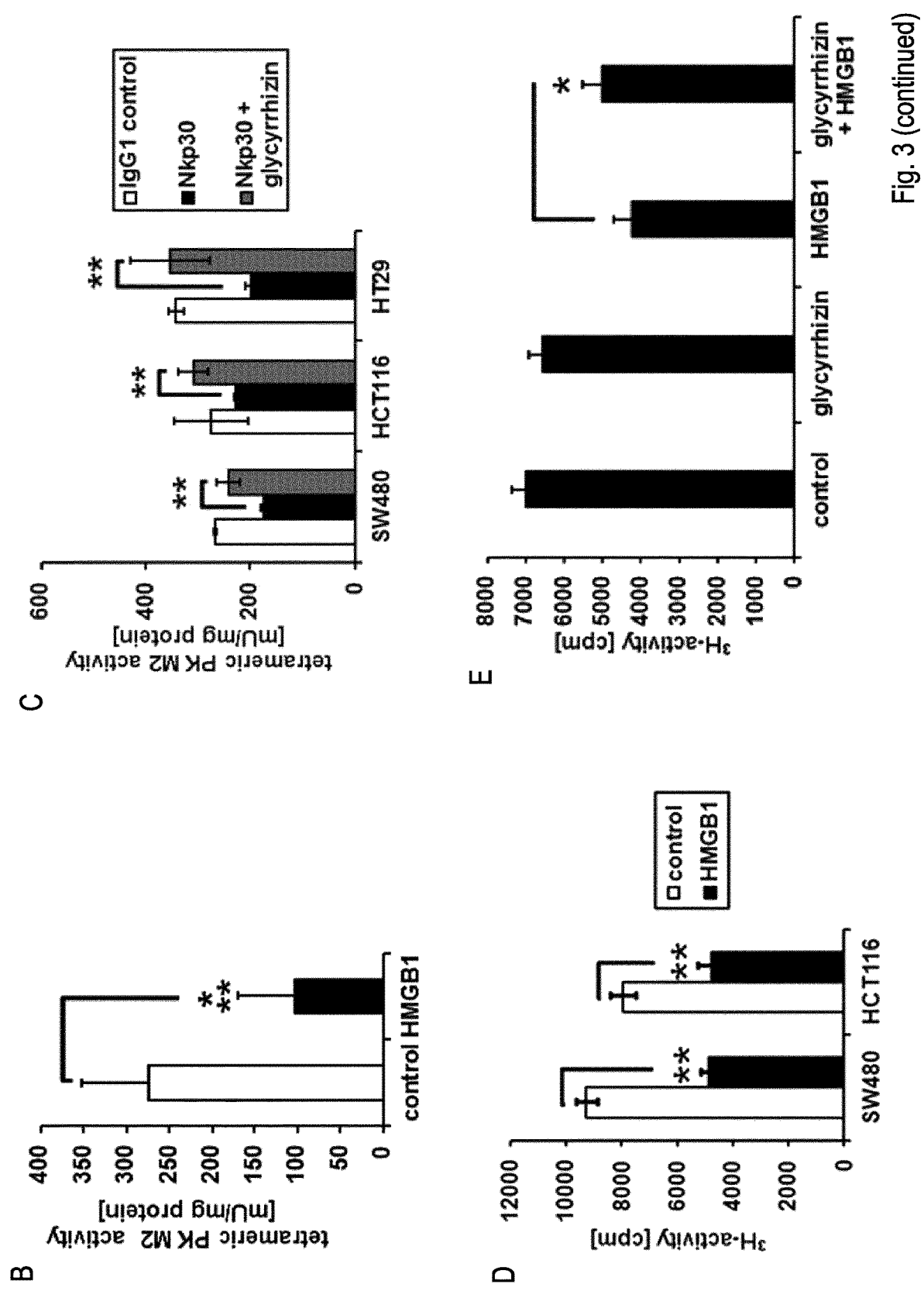
Figure 3:
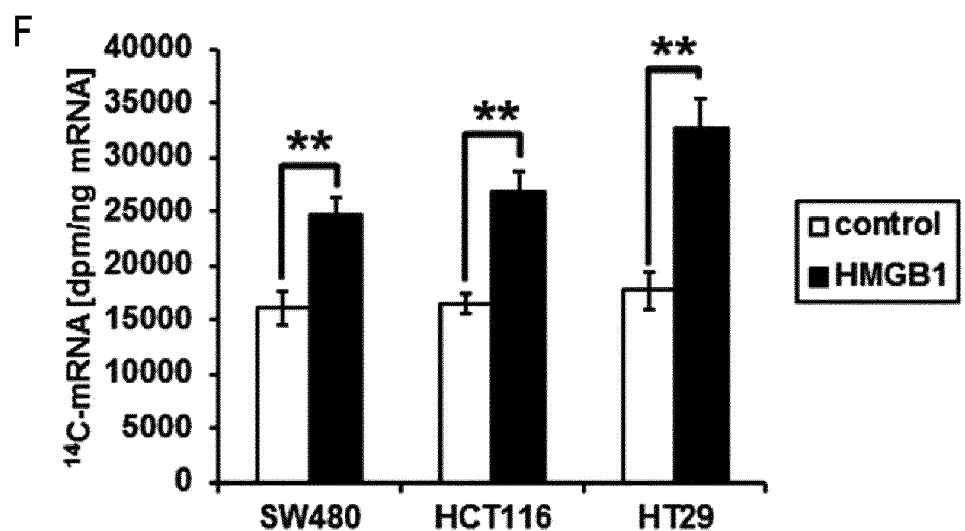
Figure 3:
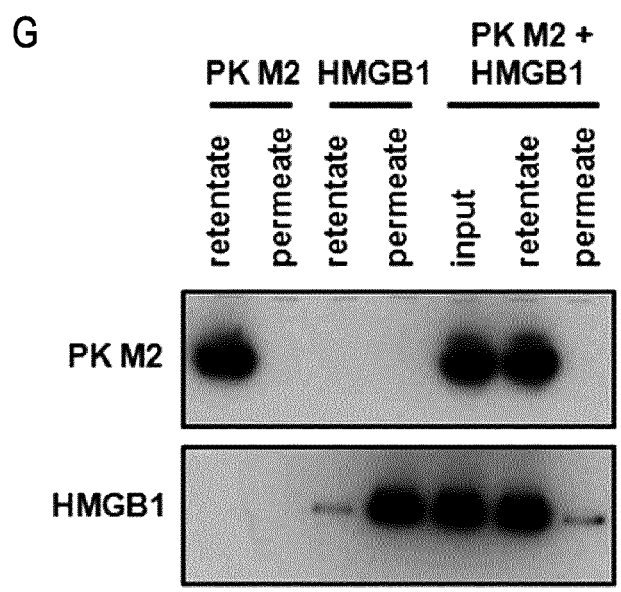

FIG. 3: HMGB1 blocks glycolysis by interfering with PK M2. (A) Activities of glycolytic enzymes measured in cytosolic fractions after treatment with HMGB1 (80 nM, 24 h, n=5). HK=Hexokinase, PFK=Phosphofructokinase, GAPDH=Glyceraldehyde 3-phosphate dehydrogenase, TPI=Triose-phosphate isomerase, PGM=Phosphoglycerate mutase, ENO=Enolase, LDH=Lactate dehydrogenase. (B) Colon cancer tissue slices from a fresh surgical specimen were treated with HMGB1 (160 nM, 72 h). Tetrameric PK M2 activity was measured in eight homogenates. (C) PK M2 activity in colorectal cancer cells was measured after 24 h incubation with the supernatant derived from stimulated NK cells from blood donor #2 (see FIG. 1D). Glycyrrhizin (200 µM) was used as a HMGB1 inhibitor (n=3). (D) 5-3H-glucose turn-over was assessed after treatment with HMGB1 (80 nM, 24 h, n=3). (E) The experiment using SW480 cells was performed as outlined in (D). Glycyrrhizin (200 µM) was used as an inhibitor of HMGB1 (n=3). (F) Enrichment of 14C in the mRNA of crude extracts after treatment with HMGB1 (80 nM, 24 h, n=3). (G) Isolation of the PK M2-HMGB1 complex: ultrafiltration of a solution containing 2 µM human PK M2 and 2 µM human HMGB1. The filtrated PK M2-HMGB1 complex was exposed to Western Blotting. *p<0.05, p<0.002, *p<0.00008.

Figure 4:
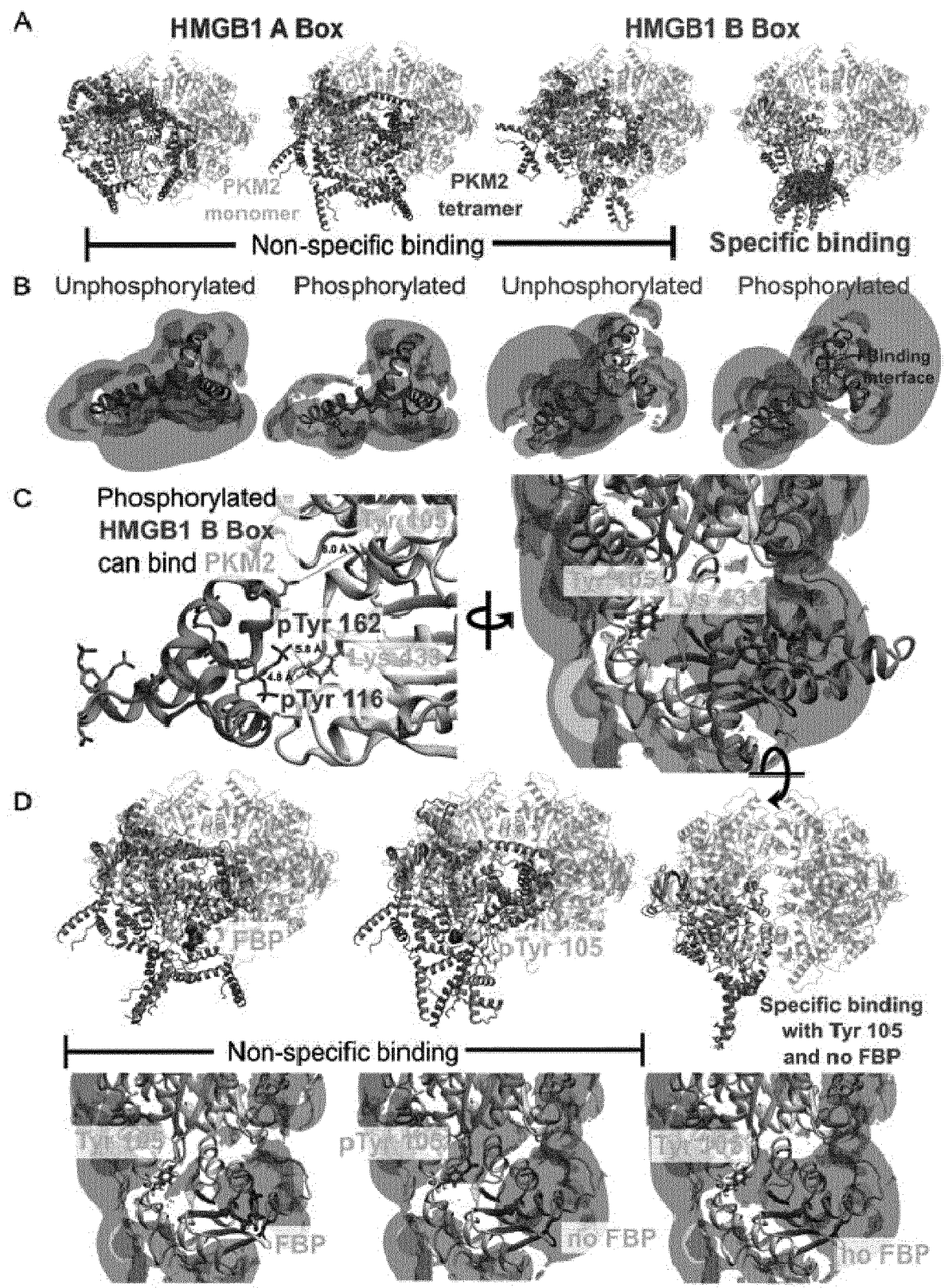

FIG. 4: HMGB1 is an allosteric inhibitor of tetrameric PK M2. (A) The calculations were performed for the following HMGB1 constructs: leftmost: A box (dark), tyrosines unphosphorylated; center left: A box, tyrosines phosphorylated; center right: B box, tyrosines unphosphorylated; rightmost: B box, tyrosines phosphorylated. (B) Dark clouds=electrostatic potentials of HMGB1 A and B box, with: leftmost) A box, unphosphorylated tyrosines; center left) A box, phosphorylated tyrosines; center right) B box, unphosphorylated tyrosines; rightmost) B box, phosphorylated tyrosines. (C) Left: Distances from HMGB1 Box B residues pTyr 116 and pTyr 162 (numbering according to PDB file: 2YRQ, corresponding to residues 109 and 155, respectively, in the human sequence) to PK M2 K433 for the best ranked docked pose and of PK M2 Y105 to the nearest charged residue from the HMGB1 Box B. Right: A rotated view with the electrostatic potential (dark) of PK M2. (D) The experiment was performed as outlined in (A), here in the presence of FBP (left) or with Tyr105 phosphorylated (center) or in the absence of FBP and with unphosphorylated Tyr 105 (right).

Figure 5:
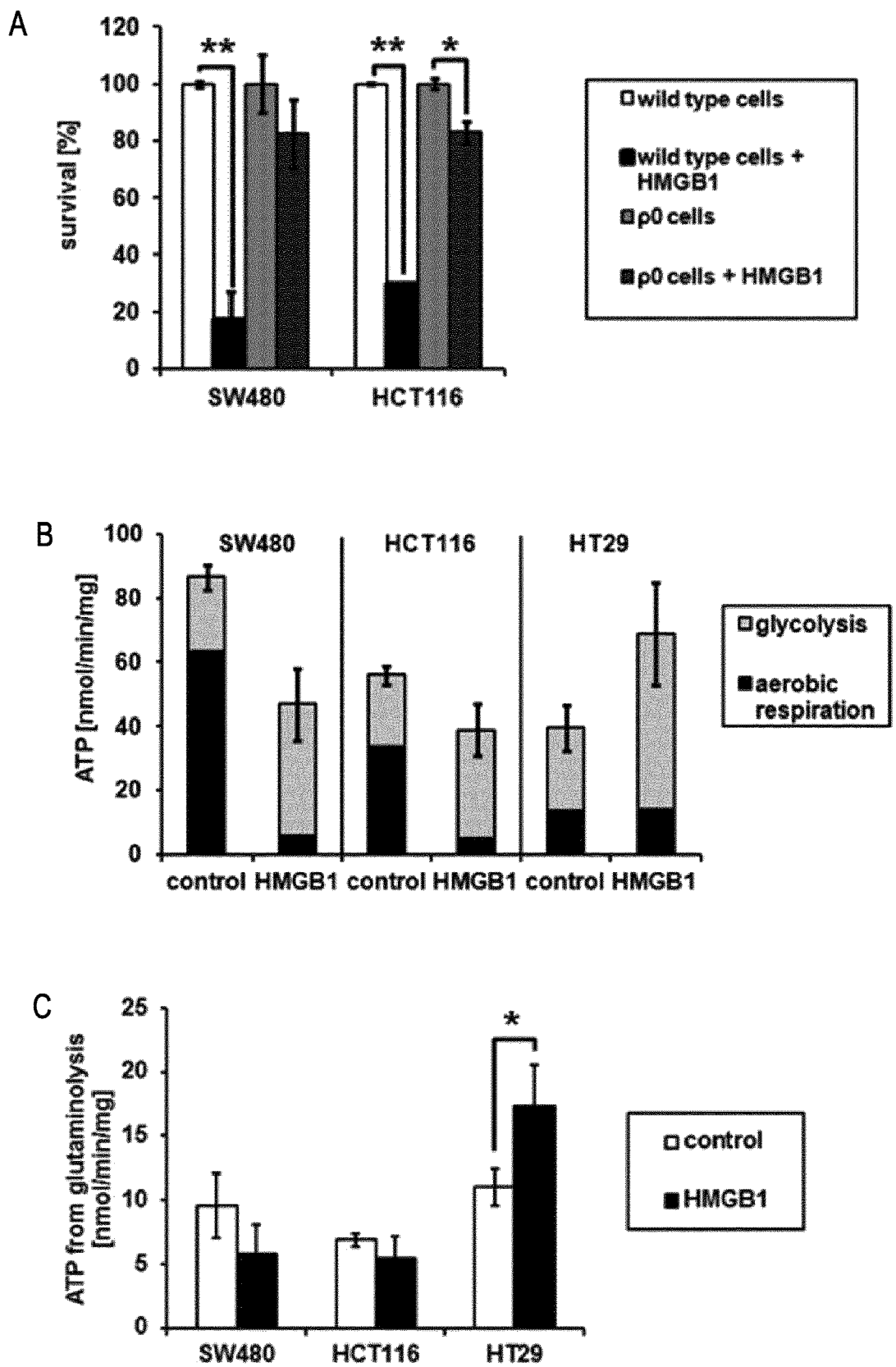
Figure 5:
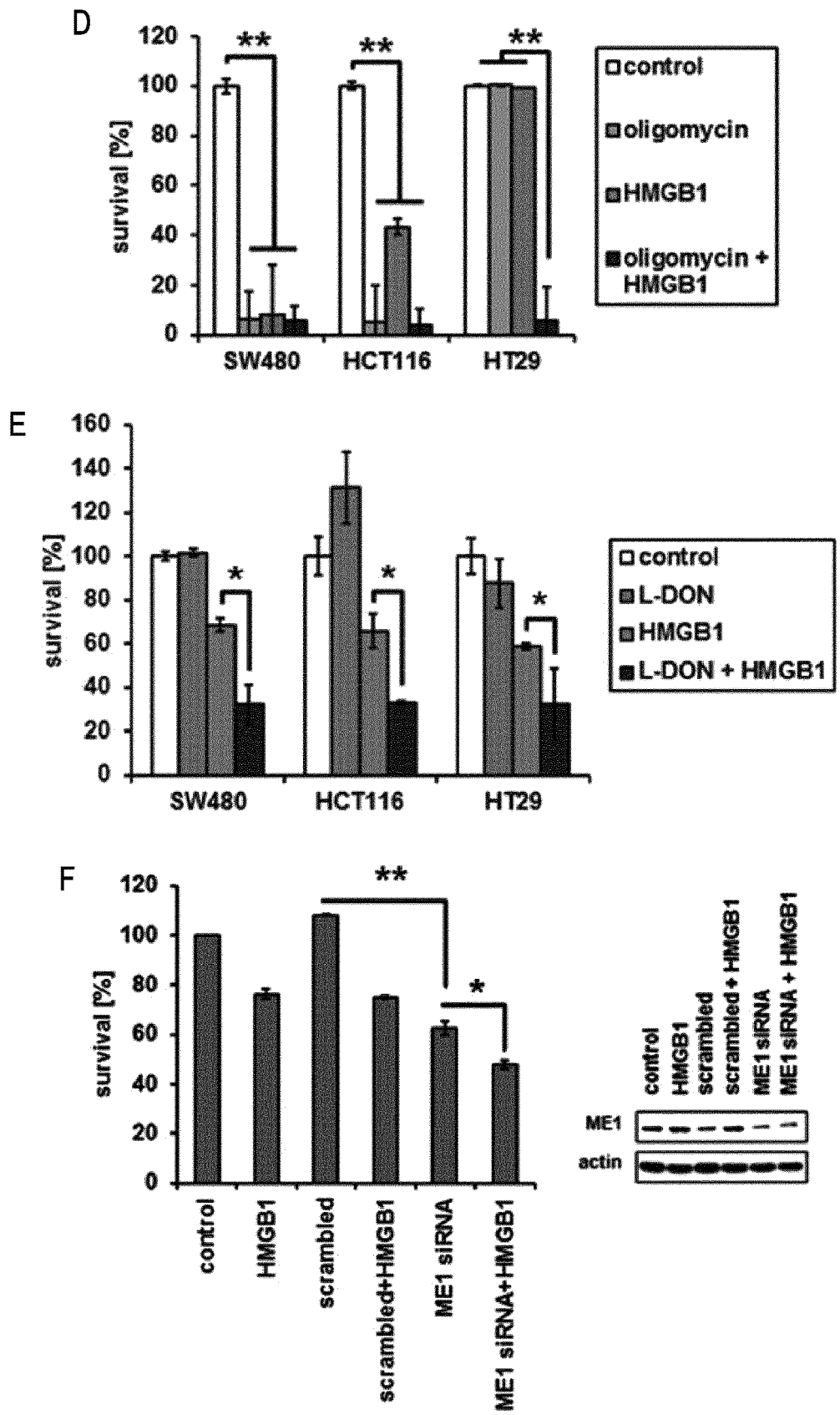
Figure 5:
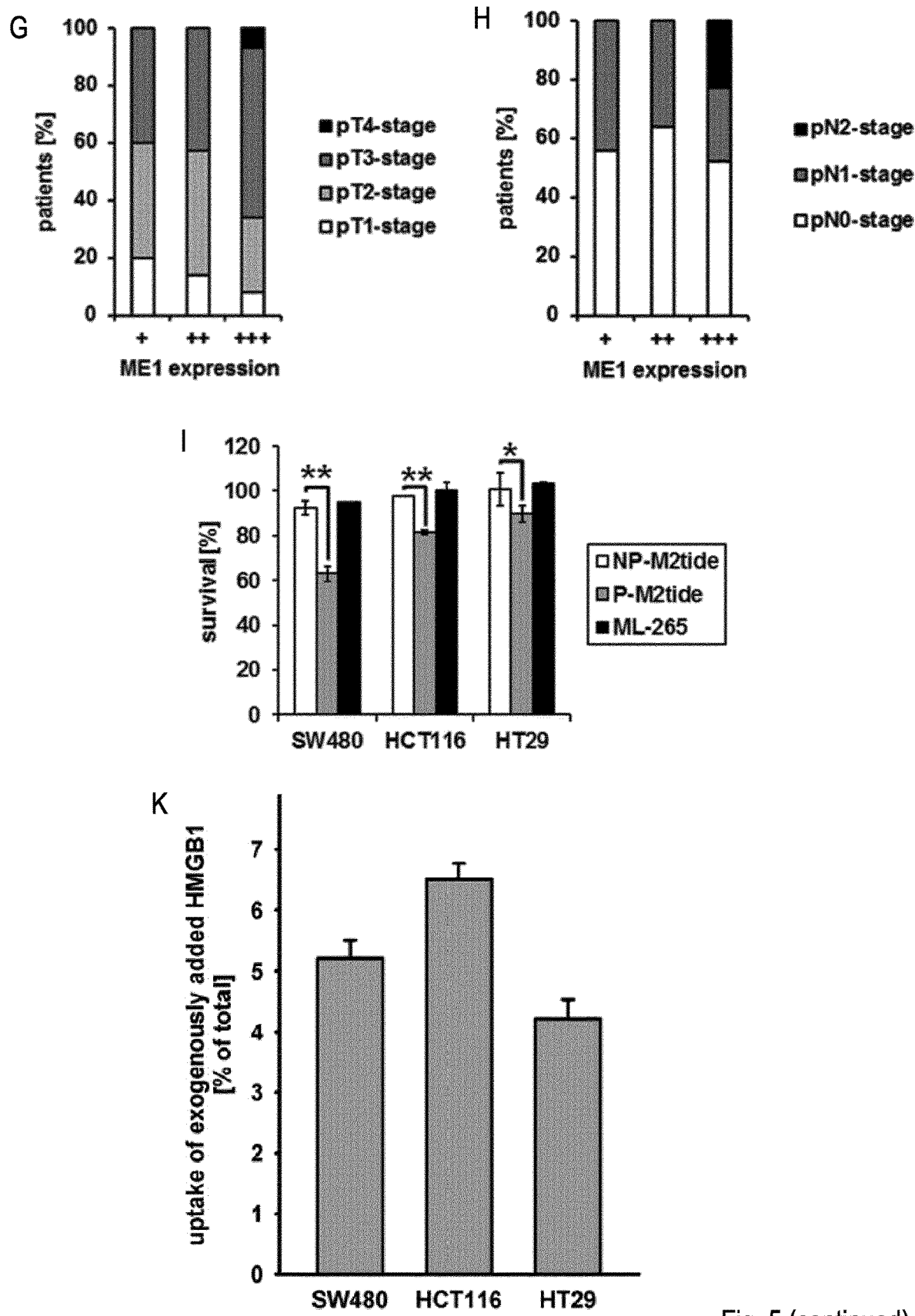
Figure 5:
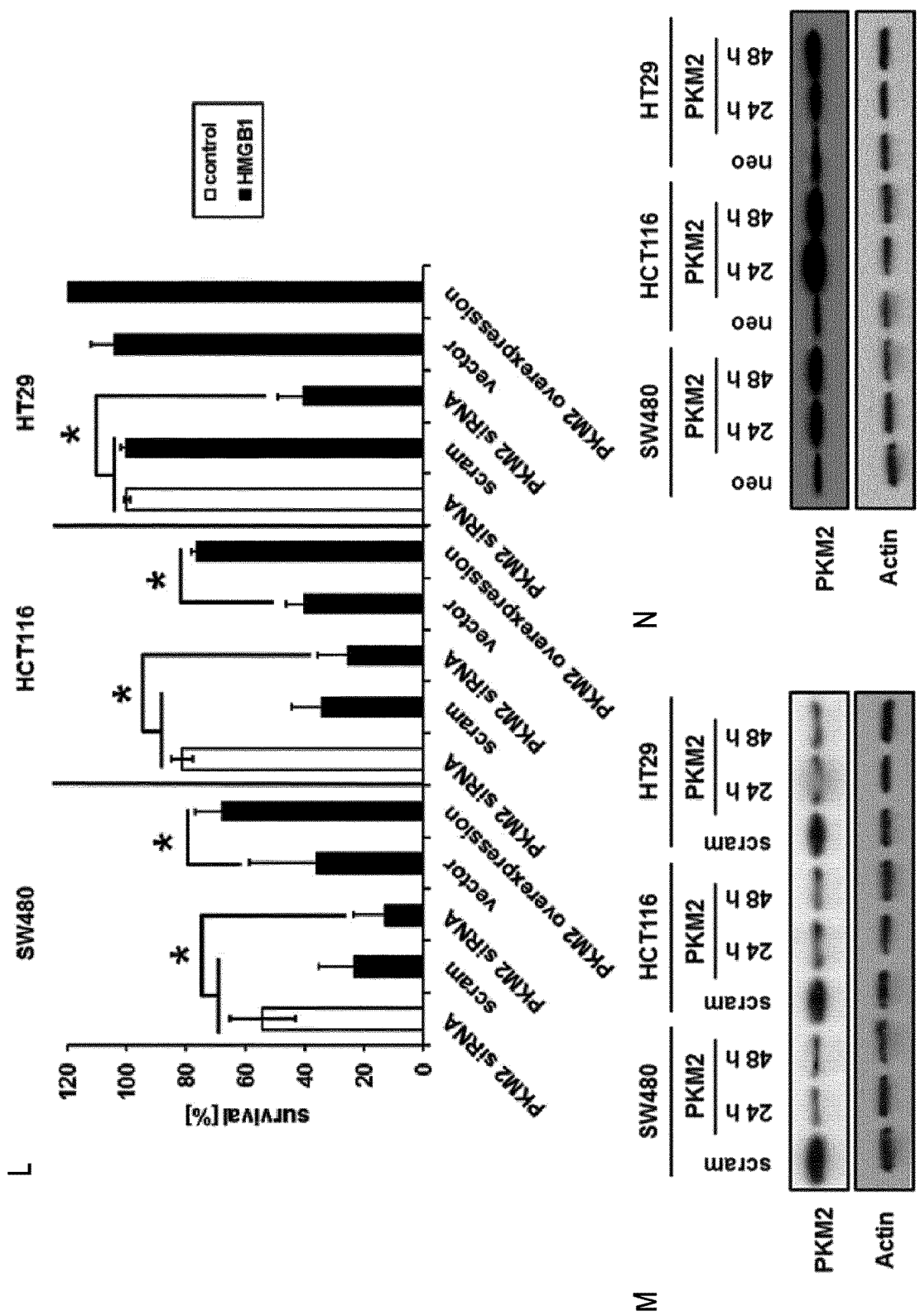

FIG. 5: Glucose fermentation and glutaminolysis circumvent the HMGB1-triggered metabolic block in cancer cells. (A) Viability assay performed with respiratory chain deficient cells (ρ0) and control (wild type) cells treated with HMGB1 (160 nM, 72 h, n=3). **p<0.0001. (B) The amount of ATP production was calculated from 02 consumption and from 13C-lactate efflux derived from 13C labeled glucose. (C) The amount of ATP production was calculated from 13C-lactate efflux derived from 13C labeled glutamine. Cells were treated with HMGB1 (80 nM, 24 h, n=3, *p<0.02). (D) Survival of cells after treatment with oligomycin (10 ng/ml) and HMGB1 (80 nM) (both 72 h, n=3, **p<0.0001). (E) Crystal violet survival assay in glucose free medium after treatment with HMGB1 (80 nM, SW480 and HCT116; 160 nM, HT29; 24 h). L-DON (1 μM) was added as indicated (n=3, *p<0.02). (F) After siRNA-mediated knock-down of ME1 the HT29 cells were treated with HMGB1 (80 nM, 72 h, n=3, *p<0.0003, **p<0.000002). Right panel: immunoblot with anti-ME1 antibody to confirm the knock-down. (G) ME1 expression levels and local invasion depth of cancer tissue (pT stage) in patients with rectal carcinoma; +low, ++moderate, +++ strong expression of ME1. (H) Association of ME1 expression levels and lymph node metastasis (pN stage) in patients with rectal carcinoma. (I) to Inhibition of tetrameric PKM2 phenocopies the cytotoxicity of HMGB1. (I) Cells were treated with 100 μM P-M2tide (phosphotyrosine peptide) for 24 h (n=3). The PKM2 activating small molecule ML-265 that binds to the dimer-dimer interface distant from the P-M2tide binding site did not induce cytotoxicity. (K) Cytosolic fractions of the indicated cells treated with 125I-labelled HMGB1 (80 nM, 24 h, n=3). (L) PKM2 was down-regulated or overexpressed transiently and then treated with HMGB1 (80 nM, 72 h, n=3). Successful knock-down or overexpression of PKM2 was confirmed by western blotting (M, N). Error bars represent the SD. *p<0.05, **p<0.01.

Figure 6:
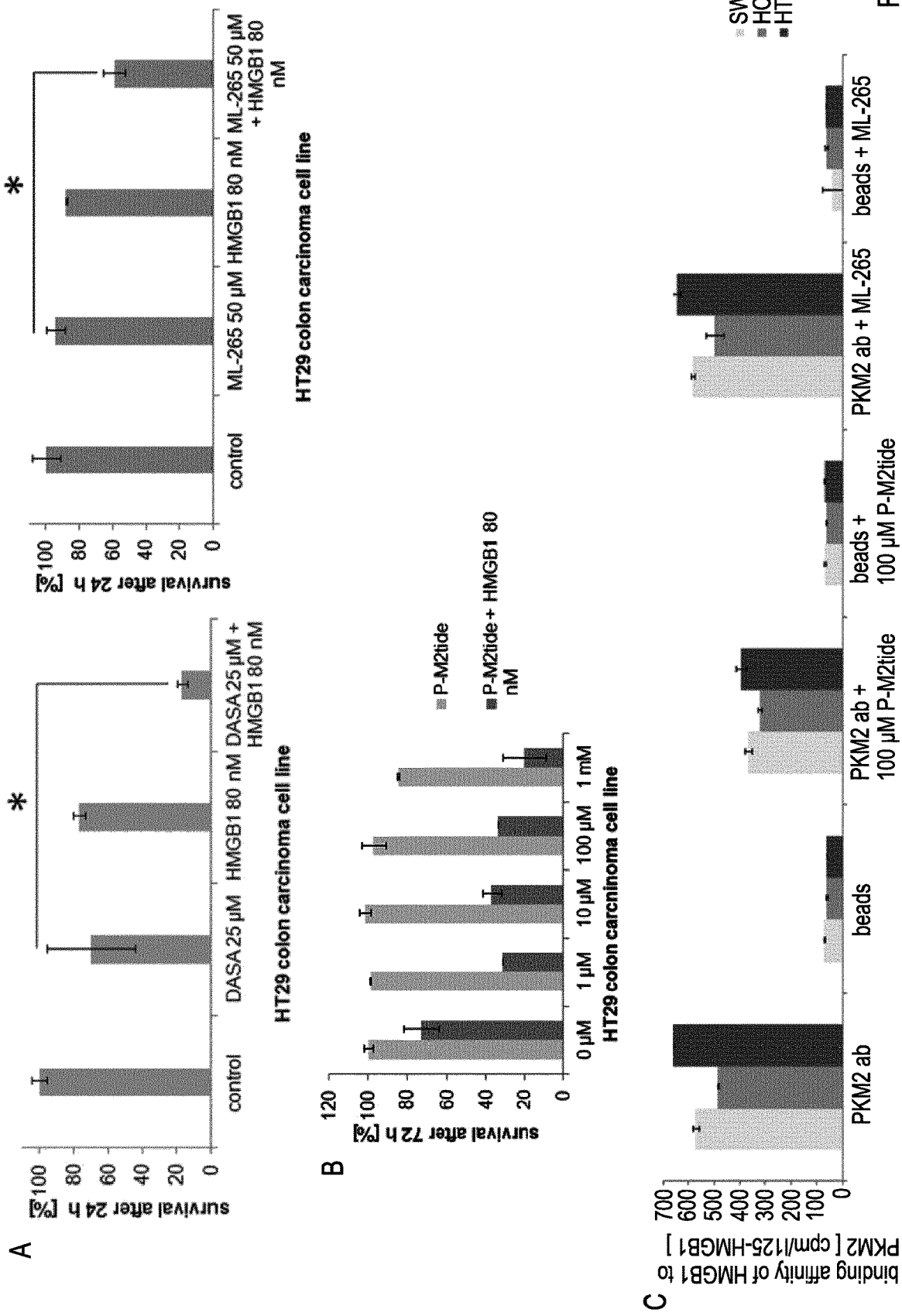

FIG. 6: Co-administration of HMGB1 and an activator (A left and right) or an inhibitor (B) of PMK2 has a synergistic cytotoxic effect, as determined in the crystal violet cytotoxicity assay (assays were performed in duplicate, * indicates p<0.05). (C) Immunoprecipitation with I125-labeled HMGB1 (PKM2 pull-down). HMGB1, like phosphotyrosine-peptides, binds close to the allosteric center of PKM2, leading to a competition in binding. In contrast, the activator ML265, which binds to the tetramer at the dimer-dimer interface, which is far off the allosteric center, does not compete with HMBG1.

Figure 7:
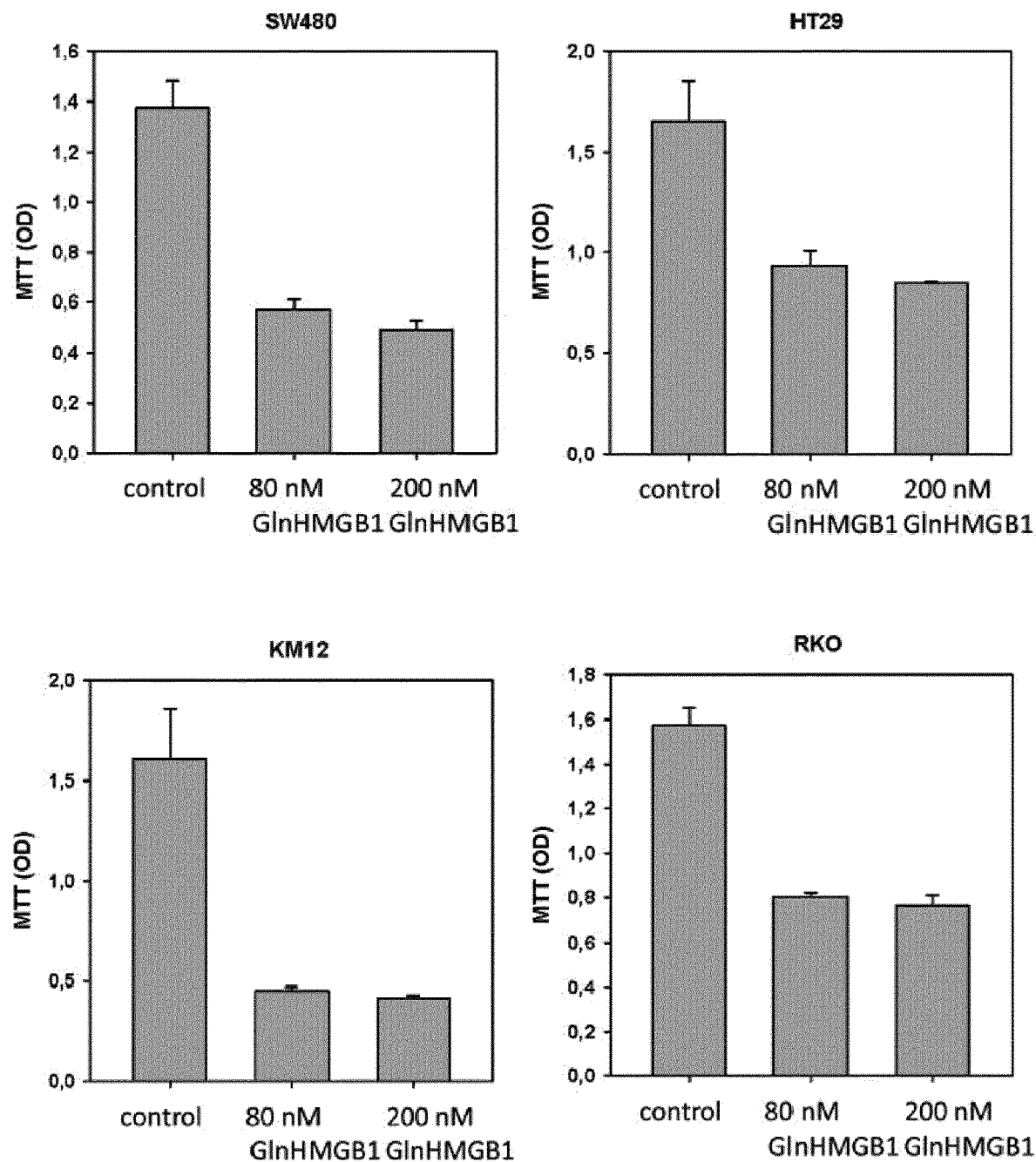
Figure 7:
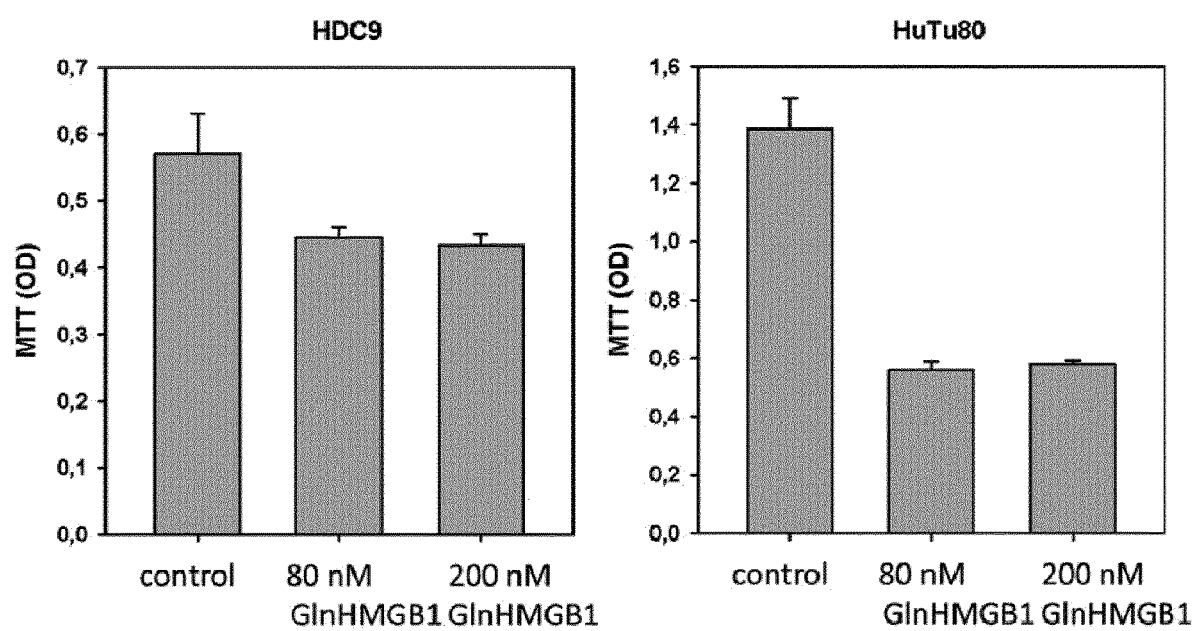

FIG. 7: Cell-death inducing effect of oligo-phosphorylated HMGB1: indicated cancer cell lines were incubated with two different concentrations of GInHMGB1 (SEQ ID NO:12) and cell viability was tested with the MTT assay; control: no addition of GInHMGB1; y-axis: optical density at 630 nm.

Figure 8:
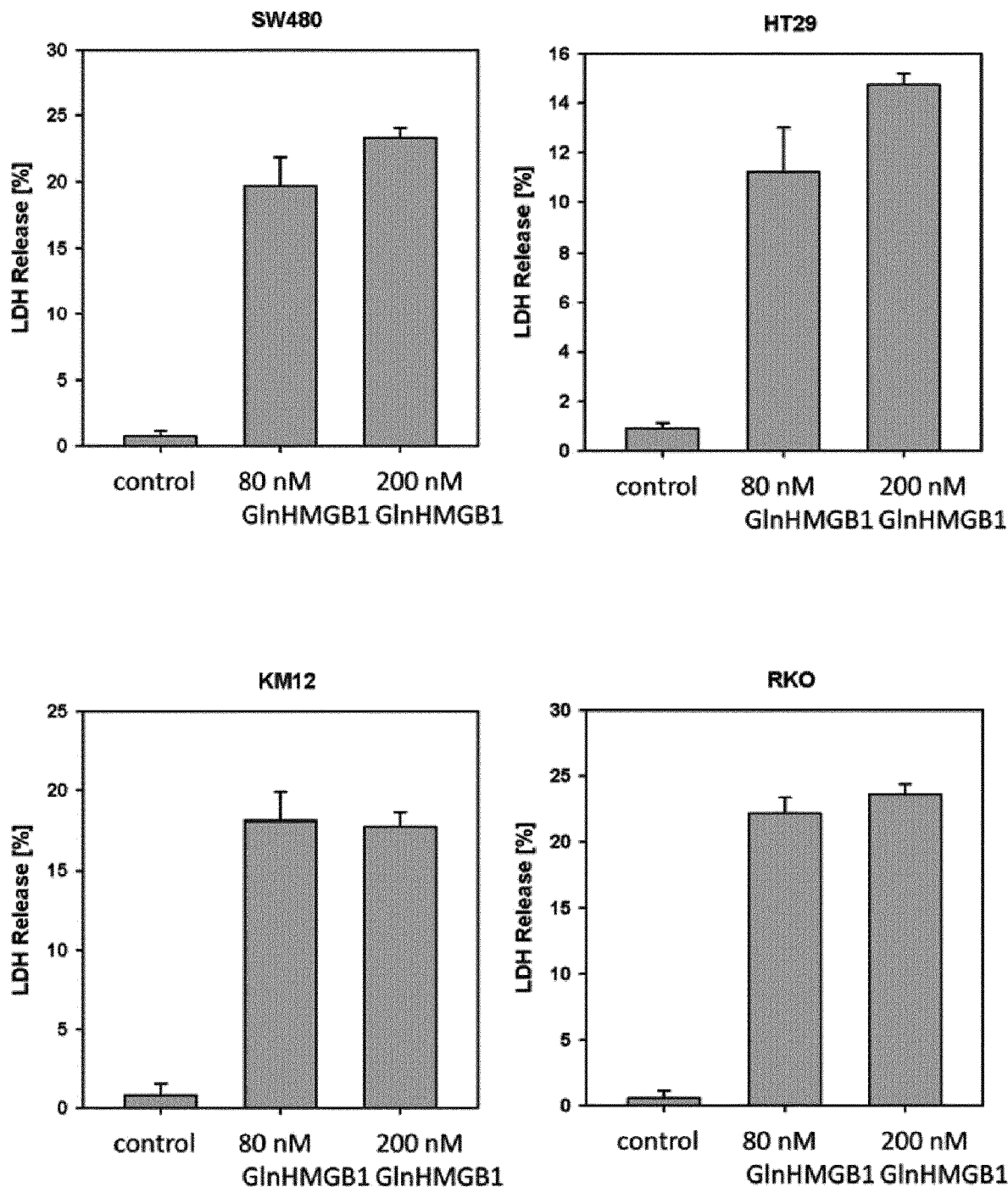
Figure 8:
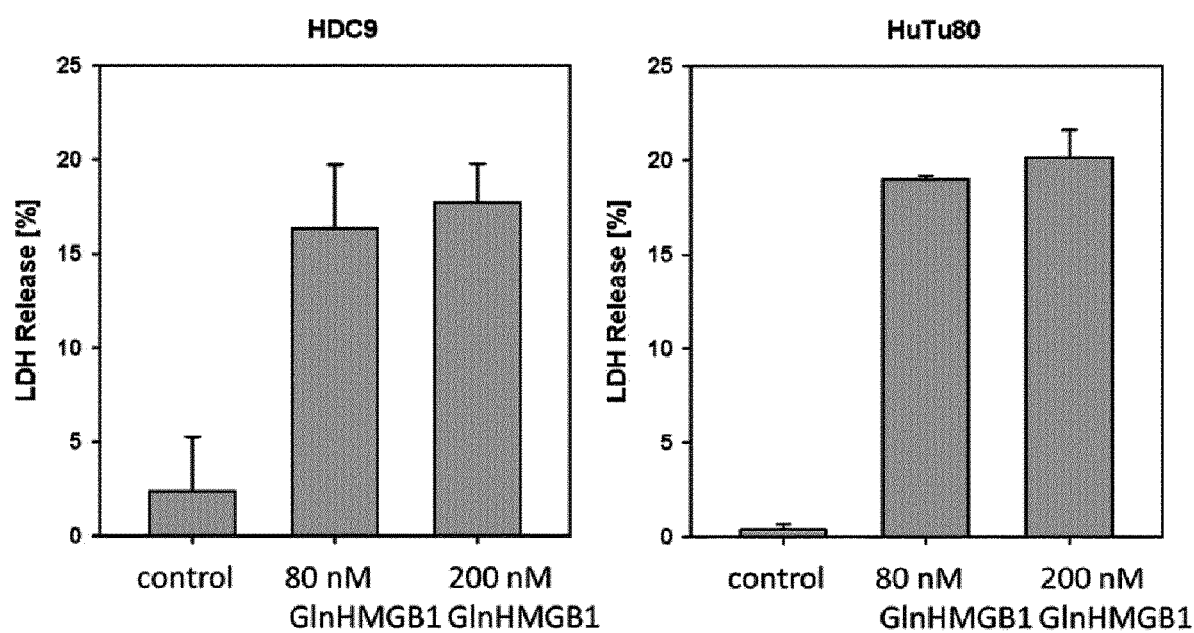

FIG. 8: Cell-death inducing effect of oligo-phosphorylated HMGB1: indicated cancer cell lines were incubated with two different concentrations of GInHMGB1 (SEQ ID NO:12) and cell viability was tested with the LDH release assay; control: no addition of GInHMGB1; y-axis: fraction of LDH in the supernatant (%).

The following Examples shall merely illustrate the invention. They shall not be construed, whatsoever, to limit the scope of the invention.

EXAMPLE 1

NK Cell Derived HMGB1 Protein Induces Cell Death in Colorectal Cancer

Given the cytotoxic activity of recombinant human HMGB1 protein on cancer cells [9] we sought to examine the cellular effects of immune cell derived endogenous HMGB1. To this end, we isolated HMGB1 from the cytosolic granules of the NK cell line NK-92 CI by HPLC (FIG. 1A). Elution of HMGB1 was confirmed by immunoblot analysis (FIG. 1B). Both NK cell derived HMGB1 and, as a comparison, recombinant human HMGB1 efficiently killed SW480 and HCT116 colorectal cancer cells (FIG. 1C). The observed cell death was specific for HMGB1 since glycyrrhizin, an inhibitor of HMGB1, significantly blocked its cytotoxic effects. In contrast, HT29 cells were resistant to low to intermediate HMGB1 concentrations (16 to 80 nM). Higher concentrations (80 nM or 160 nM) of NK cell derived HMGB1 exerted higher cytotoxicity than recombinant HMGB1 as assessed in side-by-side cytotoxicity experiments (FIG. 1I). A silver staining gel of eluate #38 confirmed that HMGB1 was isolated with high purity (single band at approximately 30 kD, FIG. 1K).

Upon stimulation of activated human peripheral blood NK cells from healthy blood donors by agonistic anti-Nkp30 mAbs, the NK cell-dependent cytotoxic effect on HT29 and HCT116 colon cancer cells was diminished by the HMGB1-specific inhibitor glycyrrhizin, indicating that HMGB1 was partly mediating the NK cell-triggered tumor cell death (FIG. 1D). In contrast, cytotoxicity in SW480 cells was not changed by glycyrrhizin.

Secretion of HMGB1 from NK cells was confirmed by immunoblot (FIG. 1E). Moreover, high levels of Interferon-γ were detected in the supernatant, indicating activation of NK cells by the agonistic anti-NKp30 mAb. Thus, NK cell derived HMGB1 protein induces cell death in colorectal cancer cells.

EXAMPLE 2

HMGB1 Inhibits Aerobic Respiration in Colorectal Carcinomas In Vitro and Ex Vivo The HMGB1 mediated cell death was characterized by formation of giant mitochondria and a substantial decrease of ATP in HMGB1-sensitive (SW480) and HMGB1 partly resistant (HCT116) cancer cells, but not in HMGB1 resistant HT29 cells. Due to the observed loss of energy equivalents and the altered mitochondrial morphology we examined whether HMGB1 affects the main ATP generating pathways, oxidative phosphorylation (OXPHOS) and glycolysis. HMGB1 treatment resulted in significantly lower activity levels of cytochrome c oxidase (COX) which is vital for oxygen derived ATP generation (FIG. 2A). Electron flow from complex I to III was unchanged, whereas coupled complex II and III activity was decreased in the HMGB1 sensitive cells (SW480) and maintained or even upregulated in the partly HMGB1-resistant cell line HCT116 and the HMGB1-resistant cell line HT29. ATP synthase activity was not diminished supporting the hypothesis that the decrease of intracellular ATP was caused by inhibition of energy metabolism up-stream of the respiratory chain. Next, we confirmed our in vitro monolayer cell culture based results in an alternative model accounting for the in vivo complexity of human colorectal cancer tissue using 300 μm thick slices from fresh tumor tissue of colorectal cancer patients. HMGB1 treatment decreased the turn-over of oxygen as demonstrated by a potent inhibition of COX activity in the primary tumor tissue (FIG. 2B). Consistently, HMGB1 strongly decreased mitochondrial oxygen consumption in colorectal cancer tissue (FIG. 2C). A similar effect was observed in cultured colon cancer cells, where the inhibition of mitochondrial oxygen consumption was pronounced in HMGB1-sensitive SW480 cells and in partly HMGB1-resistant HCT116 cells (FIGS. 2 D+E) whereas mitochondrial respiration of HMGB1-resistant HT29 cells was only slightly reduced by HMGB1 (FIG. 2F). These results indicate that HMGB1 inhibits aerobic respiration in colorectal carcinoma cells.

EXAMPLE 3

HMGB1 Controls Glycolysis in Colorectal Carcinoma Cells by Specific Inhibition of Tetrameric PK M2

Since aerobic respiration can be glucose-driven we studied the effect of HMGB1 on the activity of the major glycolytic enzymes. We observed a reduced activity of an isoform (M2) of pyruvate kinase (PK) after HMGB1 treatment (FIG. 3A) that is known to drive glucose-mediated respiration. HMGB1 specifically inhibited the tetrameric pyruvate kinase isoform PK M2 in all colorectal cancer cell lines tested as well as in ex vivo tissue slice cultures (FIGS. 3A+B). Further experiments showed that HMGB1-containing supernatants from Nkp30 stimulated NK cells from a blood donor (donor #2, see FIG. 1) also significantly inhibited the tetrameric PK M2 (FIG. 3C). Importantly, this inhibition was caused by HMGB1 since glycyrrhizin completely restored tetrameric PK M2 activity. Dimeric PK M2 activity was unchanged. Glucose flux in HMGB1-treated cells was reduced at the enolase reaction step (FIG. 3D). The observed metabolic shift was partly reversed by co-treatment with the HMGB1 inhibitor glycyrrhizin (FIG. 3E). Moreover, HMGB1 treatment resulted in an increased flux of glycolytic intermediates into the pentose phosphate shunt (FIG. 3F). Consistent with the accumulation of glucose intermediates up-stream of pyruvate kinase there was a strong increase in the hexokinase (HK) product glucose-6-phosphate that could explain the observed decrease in HK activity by product inhibition. Supporting the results from the enzymatic tests, HMGB1 physically interacted with PK M2 (FIG. 3G) in vitro. Using $^{125}$I-labeled HMGB1 we could show specific binding of HMGB1 to PKM2 in vivo by immunoprecipitating PKM2 (FIG. 6C). Non-cytotoxic P-M2tide concentrations substantially inhibited binding of HMGB1 to PKM2 supporting our in silico results (FIG. 6C). These data implicate that HMGB1 binding competes with the P-M2tide PKM2 binding site, involving the K433 near in the FBP binding pocket of PKM2. Importantly, the small molecule ML-265, an activator of PKM2, previously identified to bind to the dimer-dimer-interface of PKM2[10] (far away from the FBP binding pocket) did not compete with HMGB1 binding to PKM2 (FIG. 6C).

EXAMPLE 4

Binding and Allosteric Inhibition of Tetrameric PK M2 by HMGB1

To characterize the inhibition of tetrameric PK M2 by HMGB1 in more detail we performed in silico protein docking studies. The polyphosphorylated HMGB1 B Box produced a single cluster of poses indicating specific binding to PK M2 (FIG. 4A). Specific binding was not observed when the same calculation procedure was applied to the unphosphorylated HMGB1 B Box, or the polyphosphorylated or unphosphorylated HMGB1 A Box (FIG. 4A). This was further supported by energetic analysis of the bound clusters which showed a strongly electrostatically driven binding for the polyphosphorylated HMGB1 B Box, which is in contrast to a mainly hydrophobically driven binding typical of non-specific binding in the three other test cases (FIG. 4B). For the phosphorylated B Box, where specific binding is observed, a large region of negative electrostatic potential (red isopotential) was present in the vicinity of the binding interface, whereas the non-specific binding cases lacked such a region (FIG. 4B). Furthermore, the interaction involves K433 of PK M2 (FIG. 4C), previously shown to be involved in phosphotyrosine (pTyr) peptide binding near the FBP binding pocket[11], and in the regulation of PK M2 activity through controlling tetramerization[12]. There is variation of the electrostatic potential in the region surrounding the proposed HMGB1 binding site on binding of FBP or phosphorylation of Y105 (FIG. 4D). The decrease in the size of the positive electrostatic potential on binding FBP, or the introduction of negative electrostatic potential on phosphorylation of Y105 is likely to hinder binding of the negatively charged phosphate groups from the phosphorylated HMGB1 Box B (FIG. 4D). These results support that HMGB1 is an allosteric inhibitor of the PK M2 tetramer.

Moreover, we could phenocopy the observed cell death using a known inhibitor of the PKM2 tetramer, a phosphotyrosine peptide called P-M2tide (FIG. 5L). P-M2tide has previously been shown to bind near the FBP binding pocket involving the interaction of K433 of PKM2[11]. Whereas P-M2tide induced substantial cell death, an activator of PKM2, the small molecule ML-265 was not able to induce cell death (FIG. 5L). Penetration of the cell membrane was confirmed using $^{125}$I-labelled HMGB1[9], showing a rapid (24 h) increase of cytosolic radioactivity (FIG. 5K). Gain- and loss-of-function experiments for PKM2 using PKM2 siRNA/plasmid showed that down-regulation of PKM2 sensitized the cells to HMGB1 whereas overexpression of PKM2 rendered them more resistant to HMGB1 (FIG. 5L-N).

EXAMPLE 5

HMGB1 Resistant Cancer Cells are Characterized by Enhanced Glucose Fermentation and Increased Glutaminolysis The observed cell death induced by specific inhibition of the PK M2 tetramer and consequent inhibition of glucose driven respiration should favour the survival of cancer cells performing mainly (anaerobic) glycolysis. To test this hypothesis we generated colorectal cancer cells devoid of an intact respiratory chain ($\rho^0$ cells) from one HMGB1-sensitive (SW480) and one partly HMGB1-sensitive (HCT116) cell line. These modified cell lines, performing solely glycolysis, became almost completely resistant to HMGB1 (FIG. 5A). In order to assess the relative contributions of glycolysis, glutaminolysis, and aerobic respiration to cellular survival in presence of HMGB1 we calculated total ATP generation (FIG. 5B+C) from the lactate production rates and from the oxygen consumption. Both HMGB1 partly (HCT116) and highly resistant (HT29) cancer cells compensated the HMGB1-caused decline of ATP production efficiently by glycolysis whereas SW480 cells showed a strong decline of ATP production of ~50% (FIG. 5B). However, after HMGB1 treatment, only HT29 cells could sustain ATP production from aerobic respiration by employing glutaminolysis, as ATP yield from glutaminolysis (FIG. 5C) was in good agreement with ATP produced by 02 utilization (FIG. 5B). Consistently, after HMGB1 treatment of HT29 cells glucose oxidation was strongly decreased (~50%) and glutamine oxidation increased (~35%) as assessed by measuring production of labeled $CO_2$. Importantly, energy from aerobic respiration was critical for survival of SW480 and HCT116 cells as shown by induction of rapid cell death by oligomycin (FIG. 5D). Inhibition of glutaminolysis by L-DON resulted in synergistic cytotoxicity in both glucose deprived (FIG. 5E) and glucose supplemented medium. After down-regulation of ME1 we observed sensitization of HT29 cells towards HMGB1 cytotoxicity (FIG. 5F). Further HMGB1 inhibited HMGB1-sensitive SW480 xenograft tumor growth nude mice whereas treatment of HMGB1-resistant HT29 xenograft tumors with a combination therapy of HMGB1 and L-DON substantially inhibited tumor growth. Taken together, both enhanced glucose fermentation and increased glutaminolysis might render cancer cells resistant to HMGB1 and animal experiments suggest that treatment with recombinant HMGB1 could constitute a therapeutic option.

EXAMPLE 6

Methods

Cell Culture and Animal Studies

Human colorectal carcinoma, human glioblastoma and human NK cell lines were purchased from ATCC. Human NK cells were purified out of leukocyte concentrates. All animal work was carried out in accordance with the NIH guidelines Guide for the Care and Use of Laboratory Animals. Cell lines, cell culture and generation of rho zero cells and animal studies Human colon carcinoma cell lines SW480, HCT116, HT29 and Caco2, the human glioblastoma cell line U251MG and the Natural killer cell line NK-92 C1 were purchased from ATCC. Cell lines were regularly tested for contamination by multiplex PCR performed in the Genomics and Proteomics Core Facility 2 (DKFZ, Heidelberg, Germany). For experiments, cells were cultured for no more than 10 passages. Rho zero cells were generated as described earlier 1. (Gdynia, G. et al. Danger signaling protein HMGB1 induces a distinct form of cell death accompanied by formation of giant mitochondria. Cancer research 70, 8558-8568). Cells used in the experiments were cultured in RPMI (#1640, colon carcinomas, NK cells) or DMEM high glucose (#41965-039, glioblastoma cells) medium. Rho zero cells were generated as described earlier (Gdynia, G. et al. ibd.). Briefly, cells were cultured in RPMI medium (10% FCS, 1% P/S) supplemented with 250 ng/ml ethidiumbromide, 50 µg/ml L-pyruvate and 5 mg/ml uridine over a period of 12 weeks. For cytotoxicity measurements, cells were cultured in 96-well plates, treated with recombinant human HMGB1 protein (Sigma-Aldrich®), glycyrrhizinic acid ((3β, 18α)-30-hydroxy-11, 30-dioxoolean-12-en-3-yl 2-O-β-D-glucopyranuronosyl-β-D-glucopyranosiduronic acid)) (Sigma-Aldrich®), 10 µM (non-toxic) or 100 µM (cytotoxic) P-M2tide (aa sequence: GGAVDDDpYAQFANGG; #BML-P239-0001; Enzo Life Sciences) or 100 µM ML-265 (Cayman Chemical), then cell viability was assessed by crystal violet staining (Gillies, R. J., Didier, N. & Denton, M. Determination of cell number in monolayer cultures. Analytical biochemistry 159, 109-113 (1986)). Malic enzyme 1 knock-down was performed with 40 nM siRNA using lipofectamine in 6-well plates followed by treatment with 80 nM HMGB1 for 72 h. Sequences of siRNA were: ME1, 5'-CCCUGUGGGUAAAUUGGCUC-UAUAU-3' and scrambled control 5'-CCUGCAGUACUU-CAAGCGGtt-3'. PKM2 siRNA was from Santa Cruz. A nonspecific siRNA served as control (Dharmacon, Schwerte, Germany). For overexpression of PKM2 or ME1, cells were transfected with pCMV-PKM2 (Sino Biological Inc., Beijing, China) or pCMV-ME1 (OriGene, Rockville, Md., USA) using Lipofectamine 2000. For cytotoxicity measurements confluent cells were cultured in 96-well plates if not otherwise indicated. Cytotoxic activity of supernatants from stimulated NK cells was assessed in 96-well plates for 3 days with RPMI medium as reference. Recombinant human HMGB1 (10 ng, Sigma) suited as positive control. For mass isotopomer assays, cells were cultured in glucose- or glutamine-free medium supplemented with either uniformly labeled (U)-13C-D-glucose or U-13C-glutamine (Sigma-Aldrich®).

For animal studies six-week-old female and male athymic CD1 nude mice (Charles River, n=40) were injected subcutaneously with 5×106 SW480 or HT29 cells in 100 µl PBS in the right flank using a 30-gauge needle. Treatment was started when tumors were palpable. Daily intraperitoneal injections at the contralateral side for 2 weeks were done with 10 µg rhHMGB1 in 500 µl PBS or PBS only (control group) and/or 12.5 mg/kg/injection L-DON (Ovejera, A. A., Houchens, D. P., Catane, R., Sheridan, M. A. & Muggia, F. M. Efficacy of 6-diazo-5-oxo-L-norleucine and N-[N-gamma-glutamyl-6-diazo-5-oxo-norleucinyl]-6-diazo-5-oxo-norleucine against experimental tumors in conventional and nude mice. Cancer research 39, 3220-3224 (1979).). Tumor volume was measured by a calliper using the ellipsoid formula (length×width×height×½) as described (Tomayko, M. M. & Reynolds, C. P. Determination of subcutaneous tumor size in athymic (nude) mice. Cancer Chemother Pharmacol 24, 148-154 (1989).). After 2 weeks of treatment the animals were sacrificed.

Reversed-Phase HPLC Purification and Identification of HMGB1

Reversed phase chromatography: HMGB1 was extracted and purified by reversed phase chromatography referring to Zetterstrom and coworkers (Zetterstrom, C. K. et al. High mobility group box chromosomal protein 1 (HMGB1) is an antibacterial factor produced by the human adenoid. Pediatric research 52, 148-154) with the exception that Source 15 media were applied for chromatography. For the first purification step a Resource RPC column (6.4×100 mm; GE Healthcare) was applied. Solvent A was water with 0.17% TFA, solvent B was acetonitrile with 0.15% TFA. Flow rate was 1 ml/min. The following elution program was performed: 5% solvent B isocratic for 10 min, 5-30% B linear for 15 min, 30-60% B linear for 45 min, 60-90% B for 5 min, 90% B isocratic for 5 min. The second purification step was conducted on a Source 15RPC ST 4.6/100 column applying the same elution conditions as described above. Final purification was achieved on the Source 15RPC ST 4.6/100 column by elution with 5% B isocratic for 10 min, 5-40% B linear for 15 min, 40-50% B linear for 45 min, 50-90% B for 5 min and 90% B isocratic for 5 min.

NK-92 Cl cells were cultured in minimum essential medium (MEM) alpha (Gibco) supplemented with 12.5% fetal bovine serum (Gibco), 12.5% horse serum (Life technologies GmbH), 0.1% 2-mercaptoethanol (Gibco) and 100 IU/ml penicillin and 100 µg/ml streptomycin (both Sigma Aldrich). Cells were split and expanded by carefully rocking the culture flasks on a daily basis and adding fresh medium upon necessity. 24 hours before harvesting the cells, recombinant human IL-2 (Tecin™ from Roche, kindly provided by the NIH) was added to a concentration of 100 IU/ml. $6 \times 10^8$ NK-92 Cl cells were harvested from 1.8 l of culture medium and used for purification of intracellular membraneous vesicles as described[7]. Coomassie blue staining of all eluates (80) was performed with Brilliant Blue R-250 dye (Sigma) according to standard protocols. HMGB1 was detected by immunoblot analysis using human anti-HMGB1 antibody (1:1,000, abcam). The gel was stained with the Pierce Silver Stain Kit (Thermo Scientific, Rockford, Ill.) according to the manufacturer's instructions.

Preparation and Culture of Human Natural Killer Cells

Human NK cells were purified out of leukocyte concentrates from the blood bank in Mannheim (Germany). The concentrate was diluted with PBS and subjected to a centrifugation step on biocoll separation solution (Biochrom AG). The buffy coat was harvested and plastic adherence was carried out for 45 minutes. Out of the obtained peripheral blood leukocytes NK cells were isolated with the human NK cell isolation kit (Miltenyi) according to the manufacturer's instructions. Highly pure NK cells (95% CD3− CD56+ cells as determined by flow cytometry) were then cultured in CellGro stem cell growth medium (CellGenix) with 10% human AB serum (PAA Laboratories), 200 U/ml recombinant human interleukin-2 (IL-2, National Institutes of Health) and 100 U/mL penicillin and 100 mg/ml streptomycin (Sigma-Aldrich) at a density of $1 \times 10^6$ cells/ml. After 6 days the NK cells were harvested, counted and re-seeded at a density of $2 \times 10^6$ cells/ml in antibody pre-coated wells of a 96 well-plate in RPMI (Sigma-Aldrich) supplemented with 10% fetal calf serum (Invitrogen) and 100 U/ml IL-2. For the coating, one day before seeding the cells, the wells were incubated with 1 µg/ml of either mIgG1 (clone MOPC-21) or anti-NKp30 antibody (clone P30-15, both from BioLegend) in PBS over night at 4° C. After 2 days on the pre-coated plates, the supernatants were harvested and centrifuged to pellet potential cellular contaminants. Aliquots of the supernatants were used for performing an IFN-γ ELISA (BioLegend) according to the instructions provided by the manufacturer.

Ex Vivo Colon Carcinoma Specimens, Colon Carcinoma Tissue Microarray

Immediately after the surgical removal of the colon part containing the tumor, a fresh tumor biopsy was processed with a vibrating blade microtome (Vibratome™, Leica). Tissue slices of 300 µm were generated and incubated for the indicated times in RPMI cell culture medium. Control sections were fixed overnight in buffered 4% formalin (pH 7.4) solution, then paraffin embedded and hematoxylin and eosin (HE) staining was performed on an automated staining system (Techmate 500, DakoCytomation). HE-sections were reviewed by pathologists (WR, GG) for the presence of colorectal carcinoma. All surgical specimens were obtained from the Department of General, Visceral and Accident Surgery of the Heidelberg University Hospital (Germany). The use of the human tissue for study purposes was approved by the local ethics committee at the Heidelberg University Hospital.

For creation of the tumor microarray (TMA), tissue samples from 1.260 colorectal carcinoma patients, included in the German DACHS (Darmkrebs: Chancen der Verhutung durch Screening; *Colon Cancer: Chances of Prevention through Screening*) case control study, were collected by the Tumor Tissue Bank of the NCT Heidelberg. The use of the human tissue was approved by the local ethics committee of the University of Heidelberg and the medical boards of Baden-Wuerttemberg and Rhineland-Palatinate. Written informed consent was obtained from each participant at baseline, including the assignment of tumor tissue from patients with CRC.

Immunohistochemistry

TMA sections were immunostained as described earlier (Gdynia, G. et al. Basal caspase activity promotes migration and invasiveness in glioblastoma cells. Molecular cancer research: MCR 5, 1232-1240, doi:10.1158/1541-7786.MCR-07-0343 (2007)) using an automated staining system (Techmate 500, DakoCytomation). Visualization was done with avidin-biotin-complex peroxidase, aminoethylcarbazole and hematoxylin. The sections were incubated with the rabbit polyclonal anti-malic enzyme 1 antibody (1:100, ab97445, abcam) and processed with the following kits: ChemMate Detection Kit (K5003, DakoCytomation), ChemMate Buffer Kit (K5006, DakoCytomation) and Avidin/Biotin Blocking Kit (SP-2001, Vector Laboratories). A product of the scores of staining intensity and quantity of positive cancer cells was assessed semiquantitatively and independently by two pathologists (WR, GG). Herein the intensity range was 0=negative; 1=low; 2=medium and 3=high and the quantity 0=no positivity; 1=positivity in 0-10%; 2=positivity in 11-50%; 3=positivity in 51-80%; 4=positivity in more than 80%. For few cases of discrepant validation a consensus score was determined. The staining and evaluation was additionally performed on a second TMA giving similar results. The final immunoreactive score (IRS, ranging from 0 to 12) is obtained by multiplication of the intensity score and the quantity score. For ME1 low, moderate and strong positive expression was defined as IRS<3, IRS between 3 and 6, and IRS >6, respectively. For HMGB1 strong and strong positive expression was defined as IRS between 3 and 6, and IRS >6, respectively. Only 5 tumors were completely HMGB1 negative, thus here statistical analysis could only be performed using strong and strong positive expression. ME1 antibody specifity: cells were plated and transfected on glass coverslips in 6-well plates. The coverslips were collected, fixed with paraformaldehyde and immunostained with ME1 antibody as described for the TMA sections.

Electron Microscopy

Cells were fixed (2.3% glutaraldehyde in 50 mM sodium cacodylate, pH 7.2) in situ for 30 min at 4° C., scraped, centrifuged at 200×g for 10 min at 4° C. and stained (2% osmium tetroxide, 5% uranyl acetate). Ultrathin sections from dehydrated and Epon embedded samples were microphotographed with a Zeiss EM-10A electron microscope at 80 kV. Grating replica suited as controls for the magnification indicator.

Enzymatic Assays

Enzymatic activities of respiratory chain complexes, glycolytic proteins and malic enzyme were determined in subcellular fractions as previously described (Kaminski, M.

M. et al. T cell activation is driven by an ADP-dependent glucokinase linking enhanced glycolysis with mitochondrial reactive oxygen species generation. Cell reports 2, 1300-1315 (2012).Bruncko, M. et al. Naphthamidine urokinase plasminogen activator inhibitors with improved pharmacokinetic properties. Bioorganic & medicinal chemistry letters 15, 93-98, (2005)) using a computer-tuneable spectrophotometer (Spectramax Plus Microplate Reader, Molecular Devices; Sunny Vale, Calif., USA) operating in the dual wavelength mode; samples were analyzed in temperature-controlled 96-well plates in a final volume of 300 µl. Activity of ME1 was recorded in presence of increasing amounts of malic acid (0.02, 0.05, 0.1, 0.2, 0.5, 1, 2.5 mM). Vmax and Km were calculated using a Hanes-Woolf plot. In the presence of high substrate levels the Km for malic acid was similar in all three tested cell lines (SW480: 0.32 mM, HCT116: 0.30 mM, HT29: 0.31 mM). Vmax (mU/mg protein) values were 3.38 (SW480, 0.5-5.0 mM malic acid), 5.77 (HCT116, 0.5-5.0 mM malic acid) and 3.68 (HT29, 0.5-5.0 mM malic acid) and 1.68 (SW480, 0.02-0.2 mM malic acid), 3.24 (HCT116, 0.02-0.2 mM malic acid) and 1.89 (HT29, 0.02-0.2 mM malic acid). Two isoforms of ME1, mitochondrial (NAD(P)+dependent) ME3 and mitochondrial (NAD+dependent) ME2, had very low or no detectable activities (data not shown). Dimeric PK M2 is virtually inactive at physiological PEP levels allowing differentiation of both forms by using very high (10 mM) and low (100 µM) amounts of PEP in the enzymatic assay.

Glucose-6-phosphate levels in cells were measured using the Glucose-6-phosphate assay kit (Sigma) according to the manufacturer's protocol.

Metabolic Assays

Lactate derived from the metabolism of $^{13}C_6$-D-glucose or $^{13}C_5$-glutamine was determined by comparing the $CH_3$ group intensities of labeled and non-labeled lactate in NMR. Mitochondrial respiration was measured using an Oroboros 1 oxygraph system. Glycolysis was measured by monitoring the conversion of 5-$^3$H-Glucose to $^3H_2O$. Incorporation of $^{14}C$ into RNA ribose from U-$^{14}C$-labelled glucose was taken as glucose utilization in the pentose phosphate shunt. Enzymatic activities were determined in subcellular fractions as previously described[24].

In Silico HMGB1—PK M2 Protein Docking Studies

The individual HMGB1 Box domains (PDB: 1CKT, 2YRQ) were used rather than the complete HMGB1 structure due to the complexity of accurately accounting for the structural flexibility of the linker region (residues 79-94) between the two domains. Initial structures were taken from the Protein Data Bank (PDB), and X-ray structures were taken preferentially over NMR structures where possible. The PK M2 structure (PDB code: 3BJF), HMGB Box A (PDB code: 1CKT), HMGB Box B (PDB code: 2YRQ, residues 95-163) were used. All calculations used the chain A from 3BJF. For the calculation with FBP present, this residue was saved as a mol2 file in UCSF Chimera, and submitted to the PDB2PQR web server in addition to the modified PDB file. In all other calculations, all ligands were removed from the structures. The PDB2PQR web server was used to prepare all structures for simulation with SDA, using the AMBER force field parameters, and protonation states assigned at pH 7. Each HMGB1 structure, and the PK M2 phosphorylated at Y105, was phosphorylated using the build feature of Chimera. Charges and radii were manually added to the PQR files using the phosphotyrosine parameters as specified in the AMBER parameters database (http://personalpages.manchester.ac.uk/staff/Richard.Bryce/amber/pro/phos2_inf.html). APBS version 1.2.1 was used to solve the linearized Poisson-Boltzmann equation with simple Debye-Hückel boundary conditions, a protein dielectric constant of 1, and a solute dielectric of 78 to calculate the electrostatic potential for each protein on cubic grids of 129 points, with 1 Å grid spacing. The potential was calculated at 50 mM ionic strength, with positive and negative ions with 1.5 Å radius. Dielectric and ion-accessibility coefficients were calculated using the smoothed method (smol option), and the smoothing window was set to 0.3 Å. For the purposes of the effective charge calculations, test charges were placed as per the original SDA calculations, and additionally on the phosphorus and oxygen atoms of the phosphotyrosine residue. The SDA program was used to calculate in excess of 40,000 docked encounter complexes of each of the four HMGB1 models (unphosphorylated Box A, phosphorylated Box A, unphosphorylated Box B, phosphorylated Box B) with PK M2. The SDA calculations included electrostatic interaction, electrostatic desolvation and hydrophobic desolvation terms, with weighting factors 0.5, 1.0 and −0.013 respectively. The protein probe radius was set to 1.77 Å, solvent probe to 1.4 Å, and an exclusion grid spacing of 0.5 Å. Proteins were initially separated by 260 Å, and a simulation was stopped if the center-center distance exceeded 540 Å or the total simulation time exceeded 5,000 ps. The top 5,000 docked complexes, as ranked by favorable interaction energy, were retained for cluster analysis using the hierarchical clustering tool provided with SDA. For each simulation, the docked complexes were clustered to produce 10 clusters for quantitative and visual analysis. All images were prepared using the VMD visualization software.

NMR Analysis of Metabolites

For analysis of $^{13}C$-lactate efflux 1 ml of the cellular supernatant was centrifuged (8,000×g, 10 min, 4° C.) to spin down cellular debris. To 500 µl of the supernatant 10% of $D_2O$ were added respectively and transferred to 5 mm NMR sample tubes. The samples were measured with a Bruker AvanceIII 600 NMR spectrometer, equipped with a cryogenically cooled detection probe (QNP-CryoProbe™).

Parameters for Measurement:

Magnetic Field 14.09 Tesla; sample temperature 295 K; pulse width 4.7 us (corresponding to 30° flip angle); Broadband Composite Pulse Decoupling (Waltz65) during acquisition and relaxation delay, 128K total acquisition data points; acquisition time 1.8 sec; relaxation delay 1.5 sec; 512 transients; total experiment time 30 min.

Processing Parameters:

Zero filling to 256K real data points, exponential multiplication (lb=1.0 Hz); Fourier transformation with backward linear prediction in order to compensate for base line artifacts.

Data Analysis:

The integral of the signal of the $^{13}CH_3$ group of lactate (singlet at δ=20.108 ppm for non labeled lactate and doublet for labeled lactate at δ=20.097 ppm ($^1J(^{13}C^{13}C)$=36.8 Hz) respectively) was taken as the measure of lactate concentration. In order to get reliable quantitative results, the intensities were calibrated with standard samples containing known amounts of labeled and non-labeled lactate. This procedure also compensates errors due to incomplete relaxation of the $^{13}C$ nuclei within the chosen repetition time (3.3 sec) The determination of concentrations was performed by using the "ERETIC" functionality built in the Bruker NMR software (Topspin 3.2, Bruker BioSpin 2012). The concentrations obtained in this way were corrected for the incomplete degree of $^{13}C$ enrichments in $^{13}C_6$ glucose and $^{13}C_5$ glutamine respectively (98%).

Immunoblot Analysis, Subcellular Fractionation, Ultrafiltration

Cells were lysed in lysis buffer P (20 mM Tris-HCl (pH 7.4), 137 mM NaCl, 10% (v/v) glycerine, 1% Triton X-100, 2 mM EDTA, 100 mM phenylmethylsulfonyl fluoride and protease inhibitors (Complete mini from Roche). Lysates were centrifuged at 14,000×g (10 min) at 4° C. Total protein was measured by the Bradford (Bio-Rad) method. Soluble protein was resolved by SDS-PAGE, blotted onto nitrocellulose and incubated with one of the following antibodies: mouse monoclonal anti-β-actin (1:3,000, Sigma-Aldrich), rabbit anti PK M2 (1:1,000, Cell Signaling), rabbit anti-malic enzyme 1 (1:1,000, abcam). Appropriate secondary antibodies (1:3,000, horse-radish peroxidase-conjugated) were from Bio-Rad. Visualization was done by enhanced chemiluminescence technique (GE-Healthcare). Mitochondrial fractions were extracted using the ApoAlert Cell Fractionation Kit (Clontech) as described earlier (Gdynia, G. et al. BLOC1S2 interacts with the HIPPI protein and sensitizes NCH89 glioblastoma cells to apoptosis. Apoptosis: an international journal on programmed cell death 13, 437-447, (2008)).

Ultrafiltration of the PK M2-HMGB1 complex: equimolar amounts of HMGB1 and PKM2 were mixed in a final volume of 300 µl and filtrated (14000 g, 4° C.) to a final volume of 15 µl in an Amicon Ultra 0.5 ml 30k device (Merck-Millipore, Darmstadt, Germany). The retentate was adjusted to the original volume after centrifugation. Then filtrate and retentate were analyzed by Western Blot. For controls HMGB1 and PKM2 were also analyzed alone. Pure HMGB1 (2 µM) suited as a negative control.

Quantitative PCR Analysis

Quantitative PCR analysis was performed as described previously (Fassl, A. et al. Notch1 signaling promotes survival of glioblastoma cells via EGFR-mediated induction of anti-apoptotic Mcl-1. Oncogene 31, 4698-4708, doi: 10.1038/onc.2011.615 (2012)).

Statistical Analysis

We evaluated the association between ME1 or HMGB1 expression and local tumor extent (pT) and lymph node metastasis (pN) for all colorectal samples together as well as for the colon and rectal cancer subgroups using the linear by linear association test (Agresti A. Categorical Data Analysis. John Wiley & Sons. Hoboken, N.J., 2002). Overall survival time was defined as the time from diagnosis until death from any cause. Endpoints for progression-free survival were tumor recurrence, distant metastases or death from any cause, whatever occurred first. For the analysis of CRC (colorectal cancer)-related survival, deaths from unrelated causes were treated as competing events. Multivariate (cause-specific) proportional hazards regression models included ME1 or HMGB1 expression (IRS score), age, sex, grade, pT, pN, pM, tumor site, adjuvant and neoadjuvant chemo- and radiotherapy. The pT stadium is defined by the extent of tumor invasion into the colonic wall: submucosa (pT1), muscularis propria (pT2), subserosa/pericolic fat tissue (pT3), and perforation through peritoneum/invasion into other organs (pT4). The pN stadium is definied by the number of regional lymph node metastasis: metastasis in 1 regional lymph node (pN1a), metastasis in 2 to 3 regional lymph nodes (pN1b), tumor deposit(s) in the subserosa, or in the non-peritonealized pericolic or perirectal soft tissue without regional lymph node metastasis (pN1c), metastasis in 4 or more regional lymph nodes (pN2). The pM0 or pM1 stadium is definied by the absence or the occurrence of distant metastasis, respectively.

Results of laboratory experiments were analyzed using paired t tests. Results were illustrated using means±SD. For all statistical tests a significance level of 5% was used. Significance in figures is shown by asterisks. Statistical analyses were performed using the statistical software environment R, version 2.15.3, and Microsoft Excel 2010 software.

EXAMPLE 7

In a particular preferred embodiment of the invention the reagents needed for the enzyme activity determination are deposited as solids at the bottom and/or wall of the well-plates. Well-plates treated that way allow the addition of the sample in a sample buffer and the photometric measurement of the activity of different enzymes of the samples in the wells of the plate.

Well-plates with the solid reagents deposited to the wall and/or bottom of the wells can be obtained, for example, by dry-freezing (lyophilization), e.g. treatment of the wells of a well plate with a certain amount of a buffer solution with the reagents needed for the determination of enzyme activity in a suited concentration. Under vacuum the wells treated that way can be dried at a low temperature to evaporate the water of the buffer solution. The dried reagents for the determination of enzyme activity of a specific enzyme adhere to the bottom and the wall of the well.

TABLE 2

CLL cells used in this study with sensitivity towards PKM2 modulating drug candidates PM2-tide (inhibitor; 100 µM, 250 M) and DASA (activator; 100 µM) and predicted sensitivity by the anaerobic glycolysis predictor EnFin. Cells were classified sensitive to the drug when less than 60% were viable upon treatment (25,000 - 50,000 CLL cells, CellTiter-Glo ® Luminescent Cell Viability Assay, Promega). * = Highly sensitive leukemia cells responding to 100 µM PM2-tide. $ = Interval of 10 months between blood taking (same patient). ™ = Interval of 3 months between blood taking (same patient). The anaerobic glycolysis predictor values S for the samples were calculated according to eq. 1 as described herein above and were: 14PB0079: 1.30; 14PB0132: 2.33; 13PB0500: 1.97; 13PB0473: 2.03; 13PB0555: 2.04; 13PB0649: 2.15; 13PB0501: 1.51; 14PB0471: 1.22; 14PB0451: 1.68.

| Patient | Sample | Viable cells [PM2-tide] | Viable cells [DASA] | Sensitivity classification based on viable cells | Sensitivity prediction based on EnFin |
| --- | --- | --- | --- | --- | --- |
| P0074 | 14BP0079 | 46%* | 37% | Sensitive | Sensitive |
| P0010$ | 14PB0132 | 75% | 67% | Resistant | Resistant |
| P0641 ™ | 13PB0500 | 100% | 100% | Resistant | Resistant |
| P0645 | 13PB0473 | 91% | 90% | Resistant | Resistant |
| P0369 | 13PB0555 | 100% | 100% | Resistant | Resistant |

TABLE 2-continued

CLL cells used in this study with sensitivity towards PKM2 modulating drug candidates PM2-tide (inhibitor; 100 μM, 250 M) and DASA (activator; 100 μM) and predicted sensitivity by the anaerobic glycolysis predictor EnFin. Cells were classified sensitive to the drug when less than 60% were viable upon treatment (25,000 - 50,000 CLL cells, CellTiter-Glo ® Luminescent Cell Viability Assay, Promega). * = Highly sensitive leukemia cells responding to 100 μM PM2-tide. $ = Interval of 10 months between blood taking (same patient). ™ = Interval of 3 months between blood taking (same patient). The anaerobic glycolysis predictor values S for the samples were calculated according to eq. 1 as described herein above and were: 14PB0079: 1.30; 14PB0132: 2.33; 13PB0500: 1.97; 13PB0473: 2.03; 13PB0555: 2.04; 13PB0649: 2.15; 13PB0501: 1.51; 14PB0471: 1.22; 14PB0451: 1.68.

| | | | | | |
|---|---|---|---|---|---|
| P0641 ™ | 13PB0649 | 93% | 88% | Resistant | Resistant |
| P0010$ | 13PB0501 | 100% | 100% | Resistant | Resistant |
| P0460 | 14PB0471 | 56%* | 72% | Sensitive | Sensitive |
| P0701 | 14PB0451 | 100% | 100% | Resistant | Resistant |

| | Sensitive (no.) | Resistant (no.) | Total (no.) | Correct prediction [%] |
|---|---|---|---|---|
| EnFin Sensitive predicted | 2 | 0 | 2 | 100 |
| EnFin Resistant predicted | 0 | 7 | 7 | 100 |
| Total | 2 | 7 | 9 | |

TABLE 3

PM2-tide (inhibitor; 100 μM, 250 μM) and DASA (activator; 100 μM) response prediction of colorectal cancer and chronic lymphocytic leukemia samples using the anaerobic glycolysis predictor EnFin. CRC: 50 mg of colorectal primary cancer tissue (UICC stage I-IV) were used. CLL: a volume of 500 μl leukemic cells from the buffy coat was used for analysis.

| Tumor type | Total number | Predicted "PM2-tide/ DASA - sensitive" no. (%) | Data set source |
|---|---|---|---|
| CLL | 209 | 42 (20) | EnFin |
| Colorectal Cancer | 26 | 7 (27) | EnFin |

EXAMPLE 8

Non-Phosphorylatable HMGB1

Generation of GInHMGB1

A plasmid encoding a HMGB1 polypeptide with its B-Box domain tyrosine residues replaced by glutamine (SEQ ID NO:12) was transfected into HEK cells (serum-free suspension cell culture, 1,000 ml (app. $2.5 \times 10^6$ cells/ml), then supplemented with Valproic Acid). The cell pellet was homogenized and purified via IMAC and TALON (Clontech) Resins and eluted using imidazole. Eluates were analyzed via SDS-PAGE (Coomassie staining). After pooling of positive eluates the protein was gel filtrated (Superdex) and finally analyzed by SDS-PAGE. The purified Protein was used in the concentrations indicated in FIGS. 7 and 8 in inhibition assays.

MTT-Assay

Assays were performed at three time points (0, 24, 48 hours), and the experiment was repeated four times. At each time point the cell viability was measured using the 3-(4,5-dimethylthiazol-2-yl)-2,5-diphenyl tetrazolium bromide (MTT) assay. The MTT assay was performed as described by Mosmann (Mosmann T. Rapid colorimetric assay for cellular growth and survival: application to proliferation and cytotoxicity assays. *J Immunol Methods.* 1983;65:55-63.). In brief, at each time point, medium was aspirated from the wells and MTT (1 mg/ml) was gently added to each well. The cells were incubated for 3 hours at 37° C. in 5% $CO_2$, after which the MTT was aspirated and acidified isopropanol (0.04 M HCl) added to solubilize the reduced blue formazan crystals. Aliquots were transferred to a 96-well plate and the absorbance measured at a test filter of 590 nm and a reference filter of 630 nm on a 96-well plate reader. In all colon carcinoma cell lines used in the experiment there was a significant decrease in proliferation compared to the untreated control (p<0.05, n=4).

LDH-Assay

Lactate dehydrogenase activity was assayed spectrophotometrically by measuring the oxidation of NADH with pyruvate substrate at 340 nm as described in Bergmeyer and Berndt E. (1974). Results were analyzed using the following equation:

$$\text{Viability} = \frac{U/\text{ml [medium]}}{(U/\text{ml [cells]} + U/\text{ml [medium]})} \times 100$$

In all colon carcinoma cell lines used in the experiment there was a significant release of LDH into the medium compared to the untreated control (p<0.05, n=4). Thus GInHMGB1 can induce cell death in different carcinoma cell lines.

REFERENCES

1 Wang, H. et al. HMG-1 as a late mediator of endotoxin lethality in mice. Science 285, 248-251 (1999).
2 Lotze, M. T. & Tracey, K. J. High-mobility group box 1 protein (HMGB1): nuclear weapon in the immune arsenal. *Nature reviews. Immunology* 5, 331-342, doi: 10.1038/nri1594 (2005).
3 Apetoh, L. et al. Toll-like receptor 4-dependent contribution of the immune system to anticancer chemotherapy and radiotherapy. *Nature medicine* 13, 1050-1059, doi: 10.1038/nm1622 (2007).
4 Saidi, H., Melki, M. T. & Gougeon, M. L. HMGB1-dependent triggering of HIV-1 replication and persistence in dendritic cells as a consequence of NK-DC cross-talk. *PloS one* 3, e3601, doi:10.1371/journal.pone.0003601 (2008).

5 Yang, D. et al. High mobility group box-1 protein induces the migration and activation of human dendritic cells and acts as an alarmin. *Journal of leukocyte biology* 81, 59-66, doi:10.1189/jlb.0306180 (2007).

6 Zetterstrom, C. K. et al. High mobility group box chromosomal protein 1 (HMGB1) is an antibacterial factor produced by the human adenoid. *Pediatric research* 52, 148-154, doi:10.1203/00006450-200208000-00004 (2002).

7 Calogero, S. et al. The lack of chromosomal protein Hmg1 does not disrupt cell growth but causes lethal hypoglycaemia in newborn mice. *Nature genetics* 22, 276-280, doi:10.1038/10338 (1999).

8 Grundtman, C. et al. Effects of HMGB1 on in vitro responses of isolated muscle fibers and functional aspects in skeletal muscles of idiopathic inflammatory myopathies. *The FASEB journal: official publication of the Federation of American Societies for Experimental Biology* 24, 570-578, doi:10.1096/fj.09-144782 (2010).

9 Gdynia, G. et al. Danger signaling protein HMGB1 induces a distinct form of cell death accompanied by formation of giant mitochondria. *Cancer research* 70, 8558-8568, doi:10.1158/0008-5472.CAN-10-0204 (2010).

10 Anastasiou, D. et al. Pyruvate kinase M2 activators promote tetramer formation and suppress tumorigenesis. *Nature chemical biology* 8, 839-847, doi:10.1038/nchembio.1060 (2012).

11 Christofk, H. R., Vander Heiden, M. G., Wu, N., Asara, J. M. & Cantley, L. C. Pyruvate kinase M2 is a phosphotyrosine-binding protein. *Nature* 452, 181-186, doi:10.1038/nature06667 (2008).

12 Hitosugi, T. et al. Tyrosine phosphorylation inhibits PKM2 to promote the Warburg effect and tumor growth. *Science signaling* 2, ra73, doi:10.1126/scisignal.2000431 (2009).

13 Bhat, R. & Rommelaere, J. NK-cell-dependent killing of colon carcinoma cells is mediated by natural cytotoxicity receptors (NCRs) and stimulated by parvovirus infection of target cells. *BMC cancer* 13, 367, doi:10.1186/1471-2407-13-367 (2013).

14 Vander Heiden, M. G., Cantley, L. C. & Thompson, C. B. Understanding the Warburg effect: the metabolic requirements of cell proliferation. *Science* 324, 1029-1033, doi:10.1126/science.1160809 (2009).

15 Ikeda, Y. & Noguchi, T. Allosteric regulation of pyruvate kinase M2 isozyme involves a cysteine residue in the intersubunit contact. *The Journal of biological chemistry* 273, 12227-12233 (1998).

16 Erlandsson Harris, H. & Andersson, U. Mini-review: The nuclear protein HMGB1 as a proinflammatory mediator. *European journal of immunology* 34, 1503-1512, doi:10.1002/eji.200424916 (2004).

17 Youn, J. H. & Shin, J. S. Nucleocytoplasmic shuttling of HMGB1 is regulated by phosphorylation that redirects it toward secretion. *J Immunol* 177, 7889-7897 (2006).

18 Lazzarino, G., Viola, A. R., Mulieri, L., Rotilio, G. & Mavelli, I. Prevention by fructose-1,6-bisphosphate of cardiac oxidative damage induced in mice by subchronic doxorubicin treatment. *Cancer research* 47, 6511-6516 (1987).

19 Sandev, S., Khattar, S. K. & Saini, K. S. Production of active eukaryotic proteins through bacterial expression systems: a review of the existing biotechnology strategies. *Molecular and cellular biochemistry* 307, 249-264, doi:10.1007/s11010-007-9603-6 (2008).

20 Veith, N. et al. Organism-adapted specificity of the allosteric regulation of pyruvate kinase in lactic acid bacteria. *PLoS computational biology* 9, e1003159, doi:10.1371/journal.pcbi.1003159 (2013).

21 Zhdanov, A. V., Waters, A. H., Golubeva, A. V., Dmitriev, R. I. & Papkovsky, D. B. Availability of the key metabolic substrates dictates the respiratory response of cancer cells to the mitochondrial uncoupling. *Biochimica et biophysica acta* 1837, 51-62, doi:10.1016/j.bbabio.2013.07.008 (2014).

22 Ren, J. G., Seth, P., Everett, P., Clish, C. B. & Sukhatme, V. P. Induction of erythroid differentiation in human erythroleukemia cells by depletion of malic enzyme 2. *PloS one* 5, doi:10.1371/journal.pone.0012520 (2010).

23 Tennant, D. A., Duran, R. V. & Gottlieb, E. Targeting metabolic transformation for cancer therapy. *Nature reviews. Cancer* 10, 267-277, doi:10.1038/nrc2817 (2010).

24 Kaminski, M. M. et al. T cell activation is driven by an ADP-dependent glucokinase linking enhanced glycolysis with mitochondrial reactive oxygen species generation. *Cell reports* 2, 1300-1315, doi:10.1016/j.celrep.2012.10.009 (2012).

The invention claimed is:

1. A method of treating inappropriate cellular proliferation in a subject suffering from inappropriate cellular proliferation comprising administering an agent providing HMGB1 or a derivative thereof and a modulator of PKM2 activity selected from the group consisting of DASA, ML265, and P-M2tide, thereby treating inappropriate cellular proliferation.

2. The method of claim 1, wherein treating inappropriate cellular proliferation is treating cancer.

3. The method of claim 2, wherein said cancer is colorectal carcinoma or chronic lymphocytic leukemia (CLL).

4. The method of claim 1, wherein said inappropriate cellular proliferation is resistant to treatment with a modulator of PKM2 activity.

* * * * *